United States Patent [19]
Carini et al.

[11] Patent Number: 5,354,867
[45] Date of Patent: Oct. 11, 1994

[54] ANGIOTENSIN II RECEPTOR BLOCKING IMIDAZOLES

[75] Inventors: David J. Carini, Wilmington; John Jonas V. Duncia, Newark; Pancras C. Wong, Wilmington, all of Del.

[73] Assignee: E. I. Du Pont de Nemours and Company, Wilmington, Del.

[21] Appl. No.: 47,883

[22] Filed: Apr. 15, 1993

Related U.S. Application Data

[63] Continuation of Ser. No. 545,240, Jun. 27, 1990, abandoned, which is a continuation-in-part of Ser. No. 373,755, Jun. 30, 1989, abandoned, which is a continuation-in-part of Ser. No. 279,194, Dec. 6, 1988, Pat. No. 5,138,069.

[51] Int. Cl.$^5$ ............... C07D 233/90; C07D 401/12; C07D 403/06; A61K 31/415; A61K 31/495

[52] U.S. Cl. .................. 548/252; 544/238; 544/330; 544/370; 546/278; 548/253; 548/200; 548/235; 548/312.4; 548/312.7; 548/100; 548/315.1; 548/314.7; 548/341.5; 548/343.1; 548/346.1

[58] Field of Search ......... 548/341.5, 253, 252, 548/340.1; 546/278; 514/381, 399, 400

[56] References Cited

U.S. PATENT DOCUMENTS

| | | | |
|---|---|---|---|
| 3,772,315 | 11/1973 | Regel et al. | 548/341.5 |
| 4,207,324 | 6/1980 | Matsumura et al. | 424/273 R |
| 4,226,878 | 10/1980 | Izuka et al. | 424/273 R |
| 4,328,349 | 5/1982 | Grayboyes et al. | 548/343 |
| 4,340,598 | 7/1982 | Furukawa et al. | 424/273 R |
| 4,347,364 | 8/1982 | Walser et al. | 546/256 |
| 4,347,365 | 8/1982 | Walser et al. | 546/256 |
| 4,355,040 | 10/1982 | Furukawa et al. | 424/273 R |
| 4,379,927 | 4/1983 | Vorbruggen et al. | 544/139 |
| 4,448,781 | 5/1984 | Cross et al. | 424/269 |
| 4,463,011 | 7/1984 | Ogata et al. | 424/273 R |
| 4,532,231 | 7/1985 | Frazee | 548/342 |
| 4,568,686 | 2/1986 | Karjacainen et al. | 514/396 |
| 4,632,930 | 12/1986 | Carini et al. | 548/235 |
| 4,689,182 | 8/1987 | Rafferty et al. | 548/341.5 |
| 4,755,518 | 7/1988 | Rafferty et al. | 514/269 |
| 4,808,607 | 2/1989 | Wareing | 514/400 |
| 4,880,804 | 11/1989 | Carini et al. | 514/381 |
| 5,043,349 | 8/1991 | Carini et al. | 514/427 |
| 5,045,558 | 9/1991 | Strehlke et al. | 548/336 |
| 5,081,127 | 1/1992 | Carini et al. | 514/359 |
| 5,093,346 | 3/1992 | Carini et al. | 514/381 |
| 5,138,069 | 8/1992 | Carini et al. | 548/253 |
| 5,153,197 | 10/1992 | Carini et al. | 514/255 |
| 5,189,048 | 2/1993 | Carini et al. | 514/359 |

FOREIGN PATENT DOCUMENTS 0080163 1/1992 Australia ............... 548/341.5

(List continued on next page.)

OTHER PUBLICATIONS

Wong et al. II, Abstract No. 30 *Hypertension*, p. 340, vol. 12, No. 3, Sep. 1988 for High Blood Pressure Council Mtg., San Francisco, Calif., Sep. 28–Oct. 1, 1988 "X-6803 Methyl 2-N-Butyl-1-(4-(2-Carboxybenzamido)Benzyl)-4-Chloroimidazole-5-Acetate, Sodium Salt): A Novel Nonpeptide Angiotensin II Receptor Antagonist".

(List continued on next page.)

*Primary Examiner*—Floyd D. Higel

[57] ABSTRACT

Substituted imidazoles such as

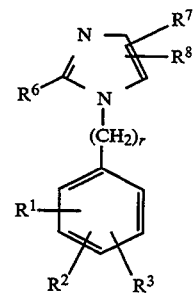

are useful as angiotensin II blockers. These compounds have activity in treating hypertension and congestive heart failure.

5 Claims, No Drawings

FOREIGN PATENT DOCUMENTS

| | | | |
|---|---|---|---|
| 0090978 | 10/1983 | European Pat. Off. | 548/341.5 |
| 0103647 | 3/1984 | European Pat. Off. | 548/341.5 |
| 125033A | 11/1984 | European Pat. Off. | 548/341.5 |
| 0125783 | 11/1984 | European Pat. Off. | 548/341.5 |
| 0146228 | 6/1985 | European Pat. Off. | 548/341.5 |
| 0245637 | 11/1987 | European Pat. Off. | 548/341.5 |
| 0253310 | 1/1988 | European Pat. Off. | 548/341.5 |
| 0324377 | 7/1989 | European Pat. Off. | 548/341.5 |
| 3426081 | 1/1986 | Fed. Rep. of Germany | 548/341.5 |
| 3426195 | 1/1986 | Fed. Rep. of Germany | 548/341.5 |
| 57-98270 | 6/1982 | Japan | 548/341.5 |
| 93-00341 | 1/1993 | PCT Int'l Appl. | 548/341.5 |

OTHER PUBLICATIONS

Chiu et al., Abstract No. 118.11, *The Pharmacologist*, vol. 30, p. A165, 1988, for ASPET meeting, Montreal, Canada, Oct. 9–13, 1988: "Nonpeptide Angiotensin II (AII) Receptor Antagonists: Structure Function Studies".

Wong et al., III, "Nonpeptide Angiotensin II Receptor Antagonists. I. Pharmacologic Characterization of 2–n–Butyl–4–Chloro–1(2–Ch–orobenzyl) imidazole–5–Acetic Acid, Sodium Salt (S–8307), " *J. Pharmacology and Experimental Therapeutics* vol. 247, No. 1, pp. 1–7 (1988).

Chiu et al., "Non-peptide angiotensin II Receptor Antagonists. II. Pharmacology of S–8308," *European Journal of Pharmacology*, vol. 157, pp. 13–21 (1988).

Dzau et al., *N. Eng. J. Med.* 310:347, 1984.

Lindgren et al, *Eur. J. Pharmacol.* 135:383, 1987.

Zatz et al., *Kidney International,* vol. 31, Suppl. 20, pp. S–123–S129 (1987).

Wong et al., Life Sciences, vol. 27, pp. 1291–1297 (1980).

Schmidt et al., J. *Cardiovascular Pharmacology*, vol. 8, pp. S100–S5105 (1986).

Torii H., Takeda Kenkyushoho, 41, No. 3/4, 180–191, (1982).

Pals et al., *Circ. Research*, vol. 29, pp. 673–681 (1971).

Streeten et al., *Handbook of Hypertension*, vol. 5, pp. 246–247, (1984).

Keeton T. K. et al., *Pharmacol. Rev.,* vol. 31, pp. 81–227, (1981).

Weinberger M. H. et al., *Medical Clinics N. America,* vol. 71, No. 5 (1987), pp. 979–991.

Dunn, M. J., *Hospital Practice*, vol. 19, pp. 99–113, (1984).

Satoh et al., *Circ. Res.,* 36/37 (Suppl. I):I-89 to I-96, (1975).

Blasingham et al., *Am. J. Physiol.,* vol. 239, F 360, (1980).

Wong et al., *J. Pharmacol. Exp. Therm.* vo. 219, pp. 104–109, (1980).

Burger, A. Medicinal Chemistry, 2nd Ed, (1960), pp. 565–571, 578–581, 600–601.

ANGIOTENSIN II RECEPTOR BLOCKING IMIDAZOLES

RELATED APPLICATION

This is a continuation of application Ser. No. 07/545,240, filed Jun. 27, 1990, now abandoned which is a continuation-in-part of U.S. Ser. No. 07/373,755, filed Jun. 30, 1989 now abandoned, which is also a continuation-in-part of U.S. application Ser. No. 07/279,194, filed Dec. 6, 1988, now U.S. Pat. No. 5,138,069 which issued to Carini et al. on Aug. 11, 1992, which discloses and claims substituted imidazoles which are angiotensin II (AII) blockers and their use, alone or in combination with other drugs, to treat hypertension and congestive heart failure.

BACKGROUND OF THE INVENTION

Field of the Invention

This invention relates to novel substituted imidazoles, and processes for their preparation. The invention also relates to pharmaceutical compositions containing the novel imidazoles and pharmaceutical methods using them, alone and in conjunction with other drugs, especially diuretics and non-steroidal anti-inflammatory drugs (NSAID's).

The compounds of this invention inhibit the action of the hormone angiotensin II (AII) and are useful therefore in alleviating angiotensin induced hypertension. The enzyme renin acts on a blood plasma $\alpha_2$-globulin, angiotensinogen, to produce angiotensin I, which is then converted by angiotensin converting-enzyme to AII. The latter substance is a powerful vasopressor agent which has been implicated as a causative agent for producing high blood pressure in various mammalian species, such as the rat, dog, and man. The compounds of this invention inhibit the action of AII at its receptors on target cells and thus prevent the increase in blood pressure produced by this hormone-receptor interaction. By administering a compound of this invention to a species of mammal with hypertension due to AII, the blood pressure is reduced. The compounds of this invention are also useful for the treatment of congestive heart failure. Administration of a compound of this invention with a diuretic such as furosemide or hydrochlorothiazide, either as a stepwise combined therapy (diuretic first) or as a physical mixture, enhances the antihypertensive effect of the compound. Administration of a compound of this invention with a non-steroidal anti-inflammatory drug (NSAID) can prevent renal failure which sometimes results from administration of a NSAID.

European Published Application 0 253 310. published Jan. 20, 1988, discloses that certain substituted imidazoles block the AII receptor and are useful therefore in alleviating angiotensin induced hypertension as well as in treating congestive heart failure. The imidazoles disclosed have the formula:

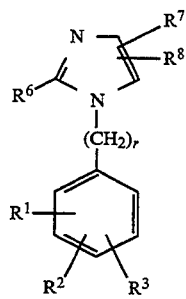

The imidazoles of the present invention differ from those of EPA 0 253 310 in the substituents $R^7$ and $R^8$ at positions 4 and 5 of the imidazole ring. In EPA 0 253 310, $R^7$ and $R^8$ are defined as follows:

$R^7$ is H, F, Cl, Br, I, $NO_2$, $CF_3$ or CN;

$R^8$ is H, CN, alkyl of 1 to 10 carbon atoms, alkenyl of 3 to 10 carbon atoms, or the same groups substituted with F: phenylalkenyl wherein the aliphatic portion is 2 to 6 carbon atoms; $-(CH_2)_m$-imidazol-1-yl; $-(CH_2)_m$-1,2,3-triazolyl optionally substituted with one or two groups selected from $CO_2CH_3$ or alkyl of 1 to 4 carbon atoms; $-(CH_2)_m$-tetrazolyl;

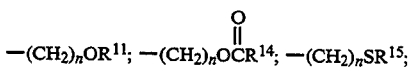

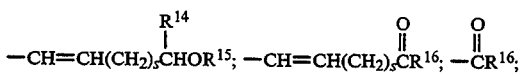

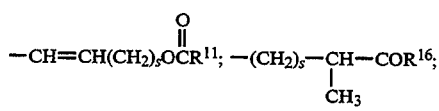

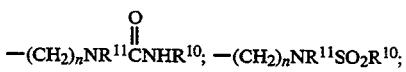

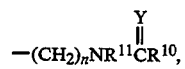

etc., where $R^{10}$, $R^{11}$, $R^{14}$, $R^{15}$, $R^{16}$, and Y are as defined below for the present invention.

Pals et al., *Circulation Research*, 29, 673 (1971) describe the introduction of a sarcosine residue in position 1 and alanine in position 8 of the endogenous vasoconstrictor hormone AII to yield an (octa)peptide that blocks the effects of AII on the blood pressure of pithed rats. This analog, [Sar$^1$, Ala$^8$] AII, initially called "P-113" and subsequently "Saralasin", was found to be one of the most potent competitive antagonists of the actions of AII, although, like most of the so-called peptide-AII-antagonists, it also possesses agonistic actions of its own. Saralasin has been demonstrated to lower arterial pressure in mammals and man when the (elevated) pressure is dependent on circulating AII (Pals et al., *Circulation Research*, 29, 673 (1971); Streeten and Anderson, Handbook of Hypertension, Vol. 5, Clinical Pharmacology of Antihypertensive Drugs, A. E. Doyle (Editor), Elsevier Science Publishers B.V., p. 246 (1984)). However, due to its agonistic character, saralasin generally elicits pressor effects when the pressure is not sustained by AII. Being a peptide, the pharmacological effects to saralasin are relatively short-lasting and are only manifest after parenteral administration, oral doses being ineffective. Although the therapeutic uses of peptide AII-blockers, like saralasin, are severely limited due to their oral ineffectiveness and short duration of action, their major utility is as a pharmaceutical standard.

Some known non-peptide antihypertensive agents act by inhibiting an enzyme, called angiotensin converting enzyme (ACE), which is responsible for conversion of angiotensin I to AII. Such agents are thus referred to as ACE inhibitors, or converting enzyme inhibitors (CEI's). Captopril and enalapril are commercially available CEI's. Based on experimental and clinical evidence, about 40% of hypertensive patients are non-responsive to treatment with CEI's. But when a diuretic such as furosemide or hydrochlorothiazide is given together with a CEI, the blood pressure of the majority of hypertensive patients is effectively normalized. Diuretic treatment converts the non-renin dependent state in regulating blood pressure to a renin-dependent state. Although the imidazoles of this invention act by a different mechanism, i.e., by blocking the AII receptor rather than by inhibiting the angiotensin converting enzyme, both mechanisms involve interference with the renin-angiotensin cascade. A combination of the CEI enalapril maleate and the diuretic hydrochlorothiazide is commercially available under the trademark Vaseretic ® from Merck & Co. Publications which relate to the use of diuretics with CEI's to treat hypertension, in either a diuretic-first, stepwise approach or in physical combination, include Keeton, T. K. and Campbell, W. B., Pharmacol. Rev., 31:81 (1981) and Weinberger, M. H., Medical Clinics N. America, 71:979 (1987). Diuretics have also been administered in combination with saralasin to enhance the antihypertensive effect.

Non-steroidal anti-inflammatory drugs (NSAID's) have been reported to induce renal failure in patients with renal underperfusion and high plasma level of AII. (Dunn, M. J., Hospital Practice, 19:99, 1984). Administration of an AII blocking compound of this invention in combination with an NSAID (either stepwise or in physical combination) can prevent such renal failure. Saralasin has been shown to inhibit the renal vasoconstrictor effect of indomethacin and meclofenamate in dogs (Satoh et al., Circ. Res. 36/37 (Suppl. I):I-89, 1975; Blasingham et al., Am. J. Physiol. 239:F360, 1980). The CEI captopril has been demonstrated to reverse the renal vasoconstrictor effect of indomethacin in dogs with non-hypotensive hemorrhage. (Wong et al., J. Pharmacol. Exp. Ther. 219:104, 1980).

SUMMARY OF THE INVENTION

According to the present invention there are provided novel compounds of formula (I) which have angiotensin II-antagonizing properties and are useful as antihypertensives.

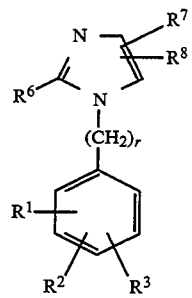
(I)

wherein
$R^1$ is

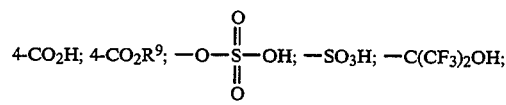

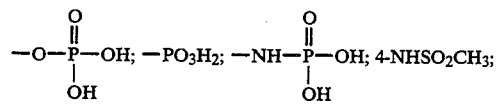

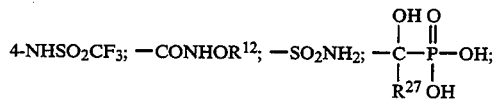

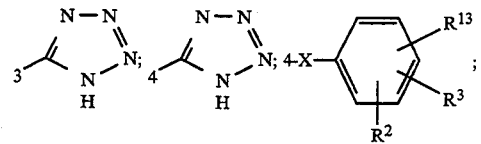

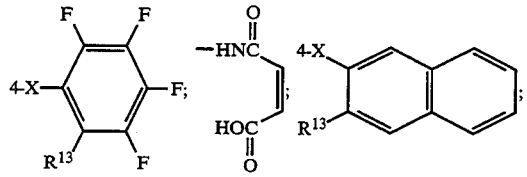

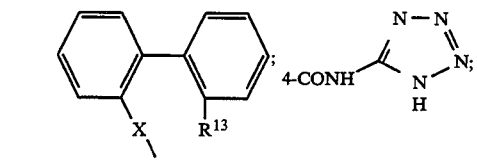

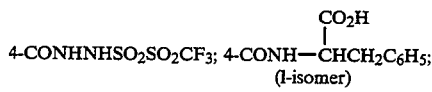

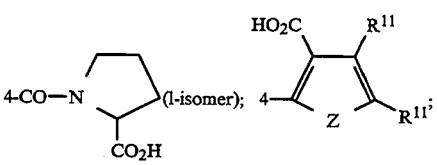

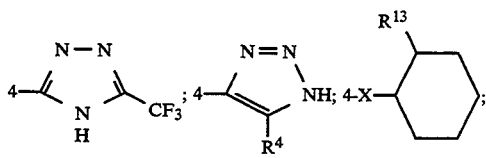

-continued

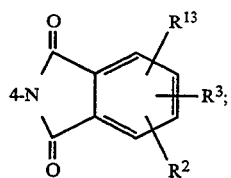

or

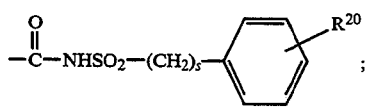

$R^2$ is H; Cl; Br; I; F; $NO_2$; CN; alkyl of 1 to 4 carbon atoms; acyloxy of 1 to 4 carbon atoms; alkoxy of 1 to 4 carbon atoms; $CO_2H$; $CO_2R^9$; $NHSO_2CH_3$; $NHSO_2CF_3$; $CONHOR^{12}$; $SO_2NH_2$;

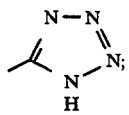

aryl; or furyl;

$R^3$ is H; Cl, Br, I or F; alkyl of 1 to 4 carbon atoms or alkoxy of 1 to 4 carbon atoms;

$R^4$ is CN, $NO_2$ or $CO_2R^{11}$;

$R^5$ is H, alkyl of 1 to 6 carbon atoms, cycloalkyl of 3 to 6 carbon atoms alkenyl or alkynyl of 2 to 4 carbon atoms;

$R^6$ is alkyl of 2 to 10 carbon atoms, alkenyl or alkynyl of 3 to 10 carbon atoms or the same groups substituted with F or $CO_2R^{14}$; cycloalkyl of 3 to 8 carbon atoms, cycloalkylalkyl of 4 to 10 carbon atoms; cycloalkylalkenyl or cycloalkylalkynyl of 5 to 10 carbon atoms; $(CH_2)_sZ(CH_2)_mR^5$ optionally substituted with F or $CO_2R^{14}$; benzyl or benzyl substituted on the phenyl ring with 1 or 2 halogens, alkoxy of 1 to 4 carbon atoms, alkyl of 1 to 4 carbon atoms or nitro;

$R^7$ is vinyl; cycloalkylidenyl; alkynyl of 2–10 carbon atoms; phenylalkynyl where the alkynyl portion is 2–6 carbon atoms; heteroaryl selected from 2- and 3-thienyl, 2- and 3-furyl, 2-, 3-, and 4-pyridyl, 2-pyrazinyl, 2-, 4-, and 5-pyrimidinyl, 3- and 4-pyridazinyl, 2-, 4-and 5-thiazolyl, 2-, 4-, and 5-selenazolyl, and 2-, 4-, and 5-oxazolyl, 2-or 3-pyrrolyl, 3-, 4- or 5-pyrazolyl, 2-, 4- or 5-imidazolyl; o-, m- or p-biphenylyl; o-, m- or p-phenoxyphenyl; 2-oxazolinyl; 2-thiazolinyl; substituted phenylalkynyl, heteroaryl, biphenylyl or phenoxyphenyl as defined above substituted with 1 or 2 substituents selected from halogen, hydroxy, mercapto, alkoxy of 1–5 carbon atoms, alkyl of 1–5 carbon atoms, $NO_2$, —CN, —$CF_3$, —$COR^{16}$, —$CH_2OR^{17}$, —$NHCOR^{17}$, —$CONR^{18}R^{19}$, $S(O)_rR^{17}$, and $SO_2NR^{18}R^{19}$; pyrrolyl, pyrazolyl or imidazolyl as defined above substituted on ring nitrogen with alkyl of 1–5 carbon atoms, phenyl or benzyl; or substituted alkyl, alkenyl, or alkynyl of 1 to 10 carbon atoms substituted with a substituted or unsubstituted heteroaryl, biphenylyl or phenoxyphenyl group as defined above; —$S(O)_r$-heteroaryl, —$S$-$(O)_r$-biphenylyl, —$S(O)_r$-phenoxyphenyl, —S-tetrazole, —$S$-$(O)_rR^{17}$, —$NR^{18}R^{19}$, —$NR^{18}$-heteroaryl, —$NR^{18}$-phenyl, —$NR^{18}$-biphenylyl, —$NR^{18}$-phenoxyphenyl, —N-phthalimido, —NH—$SO_2$-phenoxyphenyl, —NH—$SO_2$-heteroaryl, —NH—$SO_2$-biphenylyl, —NH—$SO_2$-$R^{17}$, and —S—(C=O)—$R^{17}$, N-imidazolyl, N-1,2,3-triazolyl, N-1,2,4-triazolyl, where heteroaryl is a heterocycle defined in the scope of $R^7$ and where the phenyl group in $R^{17}$ of —S—$(O)_rR^{17}$, the N-imidazolyl, N-1,2,3-triazolyl, and N-1,2,4-triazolyls may be substituted with one or two substituents as described above for heteroaryl;

$R^8$ is

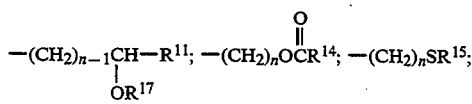

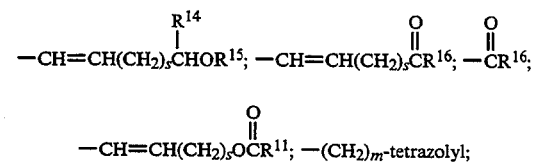

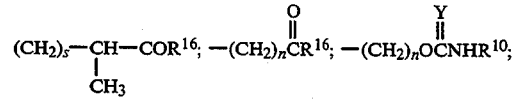

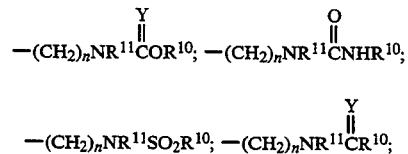

$R^9$ is

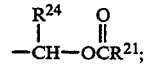

$R^{10}$ is alkyl of 1 to 6 carbon atoms or perfluoroalkyl of 1 to 6 carbon atoms, 1-adamantyl, 1-naphthyl, 1-(1-naphthyl)ethyl, or $(CH_2)_pC_6H_5$;

$R^{11}$ is H, alkyl of 1 to 6 carbon atoms, cycloalkyl of 3 to 6 carbon atoms, phenyl or benzyl;

$R^{12}$ is H, methyl or benzyl;

$R^{13}$ is —$CO_2H$; —$CO_2R^9$; —$CH_2CO_2H$, —$CH_2CO_2R^9$;

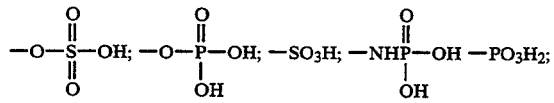

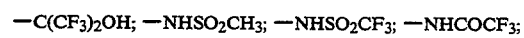

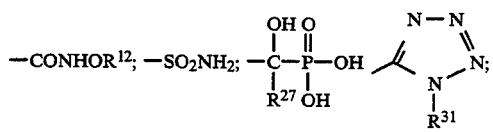

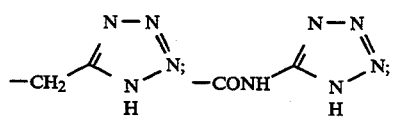

-continued

—CONHNHSO$_2$CF$_3$; 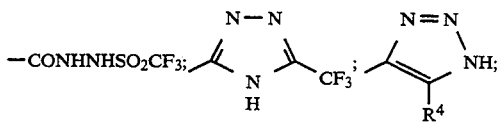

or

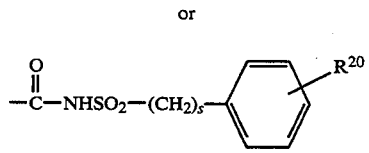

R$^{14}$ is H, alkyl or perfluoroalkyl of 1 to 8 carbon atoms, cycloalkyl of 3 to 6 carbon atoms, phenyl or benzyl;

R$^{15}$ is H, alkyl of 1 to 6 carbon atoms, cycloalkyl of 3 to 6 carbon atoms, phenyl, benzyl, acyl of 1 to 4 carbon atoms, phenacyl;

R$^{16}$ is H, alkyl of 1 to 6 carbon atoms, cycloalkyl of 3 to 6 carbon atoms (CH$_2$)$_p$C$_6$H$_5$, OR$^{17}$, or NR$^{18}$R$^{19}$;

R$^{17}$ is H, alkyl of 1 to 6 carbon atoms, cycloalkyl of 3 to 6 carbon atoms, phenyl or benzyl;

R$^{18}$ and R$^{19}$ Independently are H, alkyl of 1 to 4 carbon atoms, phenyl, benzyl, α-methylbenzyl, or taken together with the nitrogen form a ring of the formula

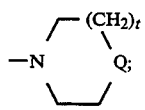

Q is NR$^{20}$, O or CH$_2$;
R$^{20}$ is H, alkyl of 1-4 carbon atoms, or phenyl;
R$^{21}$ is alkyl of 1 to 6 carbon atoms, —NR$^{22}$R$^{23}$, or

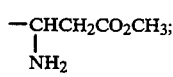

R$^{22}$ and R$^{23}$ independently are H, alkyl of 1 to 6 carbon atoms, benzyl, or are taken together as (CH$_2$)$_u$ where u is 3-6;

R$^{24}$ is H, CH$_3$ or —C$_6$H$_5$;
R$^{25}$ is NR$^{27}$R$^{28}$, OR$^{28}$, NHCONH$_2$, NHCSNH$_2$,

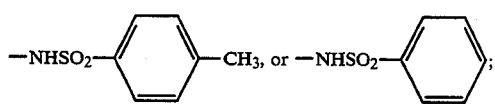

R$^{26}$ is hydrogen, alkyl with from 1 to 6 carbon atoms, benzyl, or allyl;

R$^{27}$ and R$^{28}$ are independently hydrogen, alkyl with from 1 to 5 carbon atoms, or phenyl;

R$^{29}$ and R$^{30}$ are independently alkyl of 1-4 carbon atoms or taken together are —(CH$_2$)$_q$—;

R$^{31}$ is H, alkyl of 1 to 4 carbon atoms, —CH$_2$CH=CH$_2$ or —CH$_2$C$_6$H$_4$R$^{32}$;

R$^{32}$ is H, NO$_2$, NH$_2$, OH or OCH$_3$;

X is a carbon-carbon single bond, —CO—, —CH$_2$—, —O—, —S—, —NH—,

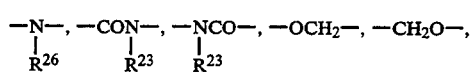

-continued

—SCH$_2$—, —CH$_2$S—, —NHC(R$^{27}$)(R$^{28}$), —NR$^{23}$SO$_2$—, —SO$_2$NR$^{23}$—, —C(R$^{27}$)(R$^{28}$)NH—, —CH=CH—, —CF=CF—, —CH=CF—, —CF=CH—, —CH$_2$CH$_2$—,

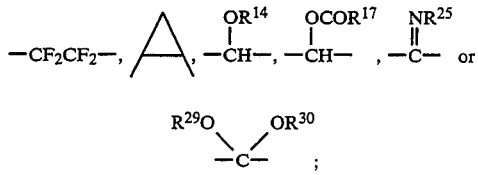

Y is O or S;
Z is O, NR$^{11}$, or S;
m is 1 to 5;
n is 1 to 10;
p is 0 to 3;
q is 2 to 3;
r is 0 to 2;
s is 0 to 5;
t is 0 or 1;

and pharmaceutically acceptable salts of these compounds;

provided that:
(1) the R$^1$ group is not in the ortho position;
(2) when R$^1$ is

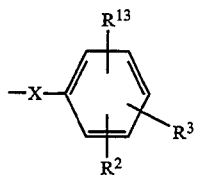

X is a single bond, and R$^{13}$ is CO$_2$H, or

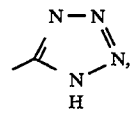

then R$^{13}$ must be in the ortho or meta position; or when R$^1$ and X are as above and R$^{13}$ is NHSO$_2$CF$_3$ or NHSO$_2$CH$_3$, R$^{13}$ must be ortho;

(3) when R$^1$ is

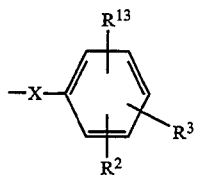

and X is other than a single bond, then R$^{13}$ must be ortho except when X=NR$^{23}$CO and R$^{13}$ is NHSO$_2$CF$_3$ or NHSO$_2$CH$_3$, then R$^{13}$ must be ortho or meta;

(4) when R$^1$ is 4-CO$_2$H or a salt thereof, R$^6$ cannot be S-alkyl;

(5) when R$^1$ is 4-CO$_2$H or a salt thereof, the substituent on the 4-position of the imidazole cannot be CH$_2$OH, CH$_2$OCOCH$_3$, or CH$_2$CO$_2$H;

(6) when R$^1$ is

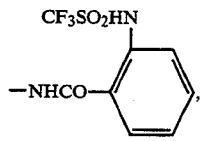

$R^6$ is not methoxybenzyl;

(7) the $R^6$ group is not

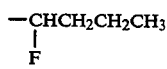

or $CH_2OH$;

Preferred for their antihypertensive activity are novel compounds having the formula:

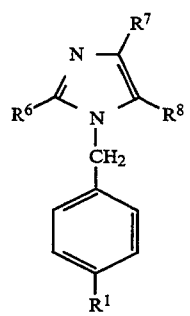

(II)

wherein $R^1$ is $-CO_2H$; $-NHSO_2CF_3$;

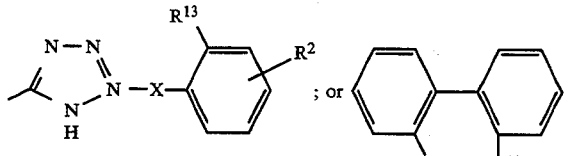

$R^6$ is alkyl of 3 to 10 carbon atoms, alkenyl of 3 to 10 carbon atoms, alkynyl of 3 to 10 carbon atoms, cycloalkyl of 3 to 8 carbon atoms, benzyl substituted on the phenyl ring with tip to two groups selected from alkoxy of 1 to 4 carbon atoms, halogen, alkyl of 1 to 4 carbon atoms, and nitro;

$R^8$ is $-(CH_2)_m$-tetrazolyl, $-(CH_2)_nOR^{11}$;

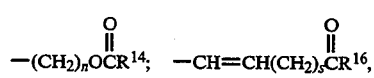

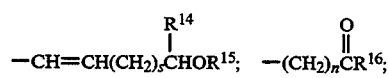

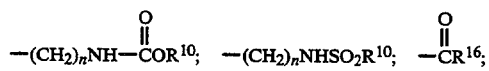

$R^{13}$ is $-CO_2H$, $-CO_2R^9$, $NHSO_2CF_3$; $SO_3H$; or

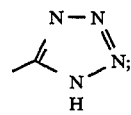

$R^{16}$ is H, alkyl of 1 to 5 carbon atoms, $OR^{17}$, or $NR^{18}R^{19}$;

X is carbon-carbon single bond, $-CO-$,

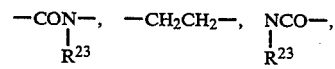

$-OCH_2-$, $-CH_2O-$, $-SCH_2-$, $-CH_2S-$, $-NHCH_2-$, $-CH_2NH-$ or $-CH=CH-$; and pharmaceutically acceptable salts of these compounds.

More preferred are compounds of the preferred scope where:

$R^2$ is H, alkyl of 1 to 4 carbon atoms, halogen, or alkoxy of 1 to 4 carbon atoms;

$R^6$ is alkyl, alkenyl or alkynyl of 3 to 7 carbon atoms;

$R^7$ is heteroaryl selected from 2- and 3-thenyl, 2- and 3-furyl, 2-, 3-, and 4-pyridyl, or p-biphenylyl,

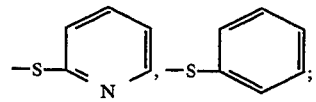

$R^8$ is $-(CH_2)_mOR^{11}$;

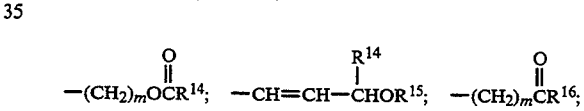

$-(CH_2)_mNHSO_2R^{10}$; or $-COR^{16}$;

$R^{10}$ is $CH_3$, alkyl of 1 to 6 carbon atoms or phenyl;

$R^{11}$ is H, or alkyl of 1 to 4 carbon atoms;

$R^{13}$ is $CO_2H$; $CO_2CH_2OCOC(CH_3)_3$; $NHSO_2CF_3$ or

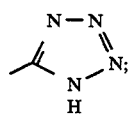

$R^{14}$ is H, or alkyl of 1 to 4 carbon atoms;

$R^{15}$ is H, alkyl of 1 to 4 carbon atoms, or acyl of 1 to 4 carbon atoms;

$R^{16}$ is H, alkyl of 1 to 5 carbon atoms; $OR^{17}$; or

-N(morpholino);

m is 1 to 5;

X=single bond, $-O-$; $-CO-$; $-NHCO-$; or $-OCH_2-$; and pharmaceutically acceptable salts.

Note that throughout the text when an alkyl substituent is mentioned, the normal alkyl structure is meant (i.e., butyl is n-butyl) unless otherwise specified.

Pharmaceutically suitable salts include both the metallic (inorganic) salts and organic salts; a list of which is given in *Remington's Pharmaceutical Sciences*, 17th Edition, pg. 1418 (1985). It is well known to one skilled in the art that an appropriate salt form is chosen based on physical and chemical stability, flowability, hydroscopicity and solubility. Preferred salts of this invention for the reasons cited above include potassium, sodium, calcium and ammonium salts.

Also within the scope of this invention are pharmaceutical compositions comprising a suitable pharmaceutical carrier and a compound of Formula (I), and methods of using the compounds of Formula (I) to treat hypertension and congestive heart failure. The pharmaceutical compositions can optionally contain one or more other therapeutic agents, such as a diuretic or a non-steroidal antiinflammatory drug. Also within the scope of this invention is a method of preventing renal failure resulting from administration of a non-steroidal antiinflammatory drug (NSAID) which comprises administering a compound of Formula (I) in stepwise or physical combination with the NSAID. The compounds of this invention can also be used as diagnostic agents to test the renin angiotensin system.

It should be noted in the foregoing structural formula, when a radical can be a substituent in more than one previously defined radical, that first radical can be selected independently in each previously defined radical. For example, $R^1$, $R^2$ and $R^3$ can each be CONHOR$^{12}$. $R^{12}$ need not be the same substituent in each of $R^1$, $R^2$ and $R^3$ but can be selected independently for each of them.

DETAILED DESCRIPTION

Synthesis

The novel compounds of Formula (I) may be prepared using the reactions and techniques described in this section. The reactions are performed in a solvent appropriate to the reagents and materials employed and suitable for the transformation being effected. It is understood by those skilled in the art of organic synthesis that the functionality present on the imidazole and other portions of the molecule must be consistent with the chemical transformations proposed. This will frequently necessitate judgment as to the order of synthetic steps, protecting groups required, deprotection conditions, and activation of a benzylic position to enable attachment to nitrogen on the imidazole nucleus. Throughout the following section, not all compounds of Formula (I) falling into a given class may necessarily be prepared by all methods described for that class. Substituents on the starting materials may be incompatible with some of the reaction conditions required in some of the methods described. Such restrictions to the substituents which are compatible with the reaction conditions will be readily apparent to one skilled in the art and alternative methods described must then be used.

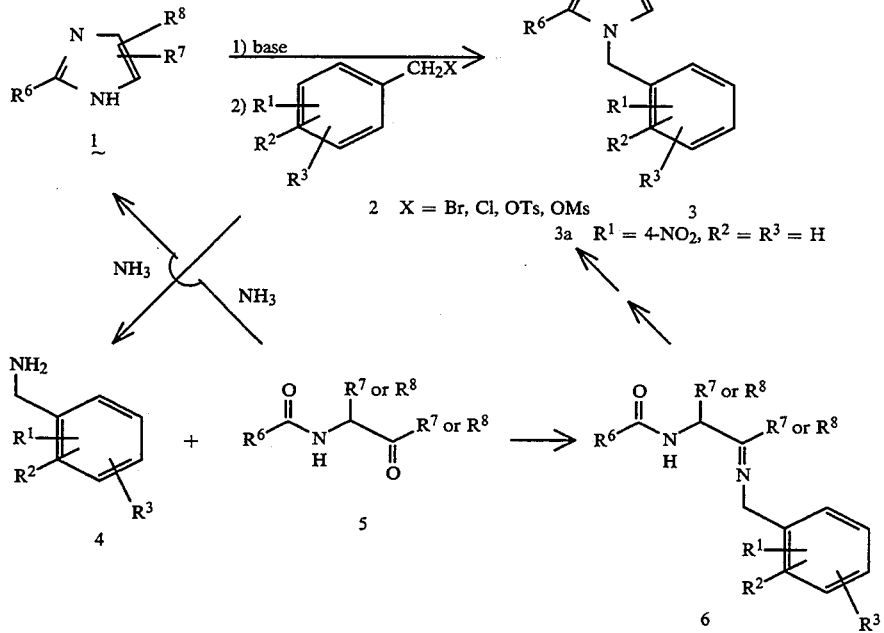

Scheme 1 a)

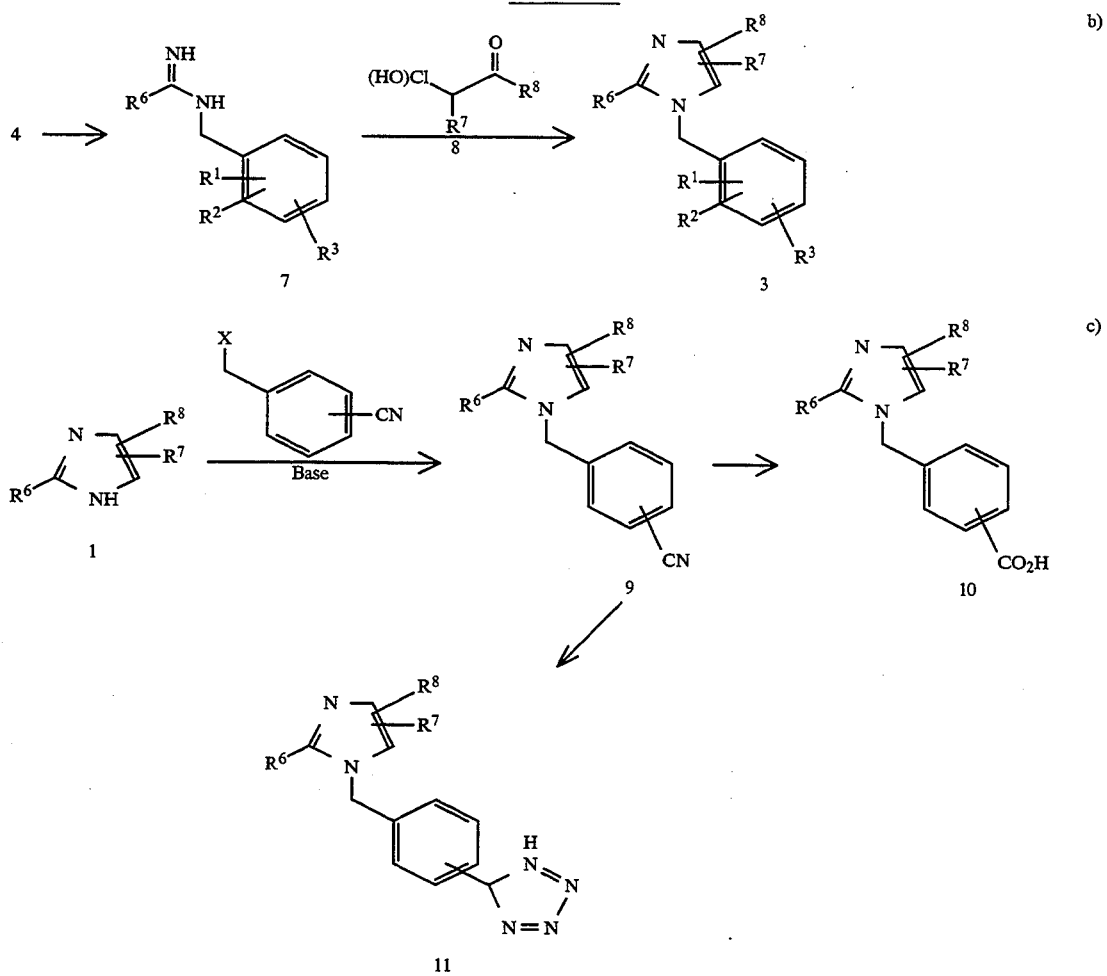

Generally, compounds of Formula (3) can be prepared by direct alkylation onto imidazole (1), with an appropriately protected benzyl halide, tosylate or mesylate (2) in the presence of base, as shown in path a). Preferably, the metallic imidazolide salt is prepared by reacting imidazole (1) with a proton acceptor such as MH where M is lithium, sodium or potassium in a solvent such as dimethylformamide (DMF) or by reacting it with a metal alkoxide of formula MOR where R is methyl, ethyl, t-butyl or the like in an alcohol solvent such as ethanol or t-butanol, or a dipolar aprotic solvent such as dimethylformamide. The imidazole salt Is dissolved in an inert aprotic solvent such as DMF, and treated with an appropriate alkylating agent (2). Alternatively, imidazole (1) can be alkylated with a benzyl halide (2, where X=Br, Cl) in the presence of a base such as sodium carbonate, potassium carbonate, triethylamine or pyridine. The reaction is run in an inert solvent such as DMF or DMSO at 20° C. to the reflux temperature of the solvent for 1–10 hours.

For example, the 4-nitrobenzyl intermediate (3a, wherein $R^1$4-$NO_2$, $R^2=R^3=H$) may be obtained by direct alkylation onto imidazole (1) with a 4-nitrobenzyl halide, tosylate or mesylate in the presence of base.

As $R^7$ and $R^8$ are different, mixtures of two regioisomer alkylation products (3b, and 3c) are obtained in which $R^7$ and $R^8$ are interchanged. When $R^8$ is CHO the alkylation is such that the benzyl group becomes attached to the adjacent nitrogen preferentially. These isomers possess distinct physical and biological properties and can usually be separated and isolated by conventional separation techniques such as chromatography and/or crystallization.

In all series examined, the more rapidly eluted isomer of a given pair has greater biological potency than the less rapidly eluted isomer.

Alternatively, any properly functionalized benzyl amine derivative (4) may be converted to imine (6) by treatment with an acylamino ketone (5) in the presence of an inert solvent such as benzene, toluene, or the like, and a catalytic amount of p-toluene-sulfonic acid or molecular sieves, N. Engel, and W. Steglich, *Liebigs Ann. Chem.*, 1916, (1978), or in the presence of alumina, F. Texier-Boulet, *Synthesis*, 679 (1985). The resulting imine (6) can be cyclized to the N-benzyl imidazole (3) with phosphorus pentachloride ($PCl_5$), phosphorus oxychloride ($POCl_3$) or triphenylphosphine ($PPh_3$) in dichloroethane in the presence of a base such as triethylamine, N. Engel and W. Steglich, *Liebigs Ann. Chem.*, 1916, (1978).

Acylamino ketone (5) is readily obtainable from amino acids via the Dakin-West reaction, H. D. Dakin, R. West, *J. Biol. Chem.*, 78, 95 and 745 (1928), and various modifications thereof, W. Steglich, G. Hofle, *Angew. Chem. Int. Ed. Engl.*, 8, 981 (1969); G. Hofle, W. Steglich, H. Vorbruggen, *Agnew. Chem. Int. Ed. Engl.*, 17, 569 (1978); W. Steglich, G. Hofle, *Ber.*, 102, 883 (1969), or by selective reduction of acyl cyanides, A. Pfaltz, S. Anwar, *Tet. Lett.* 2977 (1984) or from α-halo α-tosyl or α-mesyl ketones via the appropriate substitution reactions that one skilled in the art will readily recognize.

The functionalized benzylamines (4) may be made from the corresponding benzyl halide, tosylate or mesylate (2) via displacement with a nitrogen nucleophile, a procedure familiar to one skilled in the art. This displacement may be achieved using azide ion, ammonia, or phthalimide anion, etc., in a neutral solvent such as dimethylformamide, dimethylsulfoxide etc., or under phase transfer conditions. The benzyl halide (2) may be made by a variety of benzylic halogenation methods familiar to one skilled in the art, for example benzylic bromination of toluene derivatives with N-bromosuccinimide in an inert solvent such as carbon tetrachloride in the presence of a radical initiator such as benzoyl peroxide at temperatures up to reflux conditions.

A wide variety of toluene derivatives may be made from simple electrophilic substitution reactions on an aromatic ring. This includes nitration, sulfonation, phosphorylation, Friedel-Crafts alkylation, Friedel-Crafts acylation, halogenation, and other similar reactions known to one skilled in the art, G. A. Olah, "Friedel-Crafts and Related Reactions," Vol. 1-5, Interscience, New York, (1965).

Another way to synthesize functionalized benzyl halides is via chloromethylation of the corresponding aromatic precursor. Thus, the appropriately substituted benzene ring may be chloromethylated with formaldehyde and hydrochloric acid (HCl) for example with or without an inert solvent such as chloroform, carbon tetrachloride, light petroleum ether or acetic acid. A Lewis acid such as zinc chloride ($ZnCl_2$) or a mineral acid such as phosphoric acid may also be added as a catalyst or condensing agent, R. C. Fuson, C. H. McKeever, *Org. Reactions*, 1, 63 (1942).

Alternatively, N-benzylimidazoles (3) can also be prepared as shown in path b) by forming an $R^6$ substituted amidine (7) from an appropriately substituted benzylamine (4) which is in turn reacted with an α-haloketone, α-hydroxyketone (8), α-haloaldehyde, or α-hydroxyaldehyde, F. Kunckell, *Ber.*, 34, 637 (1901).

As shown in path a), imidazole (1) may be alkylated by a variety of benzyl derivatives. These include compounds with latent acid functionalities such as o, m, and p-cyanobenzylhalides, mesylates or tosylates as shown in path c). Nitriles of formula (9) may be hydrolyzed to carboxylic acids of formula (10) by treatment with strong acid or alkali. Preferably, treatment with a 1:1 (v/v) mixture of concentrated aqueous hydrochloric acid/glacial acetic acid at reflux temperatures for 2-96 hours or by treatment with 1N sodium hydroxide in an alcohol solvent such as ethanol or ethylene glycol for 2-96 hours at temperatures from 20° C. to reflux can be used. If another nitrile group is present it will also be hydrolyzed. The nitrile functionality can also be hydrolyzed in two steps by first stirring in sulfuric acid to form the amide followed by hydrolysis with sodium hydroxide or a mineral acid to give the carboxylic acid (10).

The nitriles (9) can be converted into the corresponding tetrazole derivative (11) by a variety of methods using hydrazoic acid. For example, the nitrile can be heated with sodium azide and ammonium chloride in DMF at temperatures between 30° C. and reflux for 1-10 days, J. P. Hurwitz and A. J. Tomson, *J. Org. Chem.*, 26, 3392 (1961). Preferably, the tetrazole is prepared by the 1,3-dipolar cycloaddition of trialkyltin or triaryltin azides to the appropriately substituted nitrile as described in detail by Scheme 15.

The starting imidazole compounds (1) are readily available by any of a number of standard methods. For example, acylaminoketone (5) can be cyclized with ammonia or equivalents thereof, D. Davidson, et al., *J. Org. Chem.*, 2, 319 (1937) to the corresponding imidazole as shown in Scheme 1. The corresponding oxazole can also be converted to imidazole (1) by action of ammonia or amines in general, H. Bredoreck, et al., *Ber.*, 88, 1351 (1955); J. W. Cornforth and R. H. Cornforth, *J. Chem Soc.*, 96, (1947).

Several alternative routes to imidazoles (1) are illustrated in Scheme 2. As shown in Scheme 2 equation a), reaction of the appropriate $R^6$ substituted imidate esters (12) with an appropriately substituted α-hydroxy- or α-haloketone or aldehyde (8) in ammonia leads to imidazoles of formula (1), P. Dziuron, and W. Schunack, *Archiv. Pharmaz.*, 307 and 470 (1974).

The starting imidazole compounds (1) wherein $R^7$ and $R^8$ are both hydrogen can be prepared as shown in equation b) by reaction of the appropriate $R^6$-substituted imidate ester (12) with α-aminoacetaldehyde dimethyl acetal (13), M. R. Grimmett, *Adv. Heterocyclic Chem.*, 12, 103 (1970).

As shown In equation c), imidazole (15; wherein $R^7$=hydrogen and $R^8$=$CH_2OH$) can be prepared by treatment of the imidate ester (12) with 1,3-dihydroxyacetone (14) in ammonia by the procedure described in *Archive der Pharmazie*, 307, 470 (1974). Halogenation of imidazole (15) or any imidazole wherein $R^7$ or $R^8$ is hydrogen is preferably accomplished by reaction with one to two equivalents of N-halosuccinimide in a polar solvent such as dioxane or 2-methoxyethanol at a temperature of 40°-100° C. for 1-10 hours. Reaction of the halogenated imidazole (16) with a benzylhalide (2) in the manner described in Scheme 1 affords the corresponding N-benzylimidazole (17); wherein $R^7$ is halogen and $R^8$ is $CH_2OH$). This procedure is described in U.S. Pat. No. 4,355,040. Alternatively, imidazole (17) can be prepared by the procedure described in U.S. Pat. No. 4,207,324.

Compounds of formula (17) can also be prepared by treatment of the starting imidazole compound (1) wherein $R^7$ and $R^8$ are both hydrogen, with the appropriate benzyl halide followed by functionalization of $R^7$ and $R^8$ by treatment with formaldehyde as described in E. F. Godefroi, et al., *Recueil*, 91, 1383 (1972) followed by halogenation as was described above.

As shown in equation d) the imidazoles (1) can also be prepared by reaction of $R^6$ substituted amidines (18) with an α-hydroxy- or α-haloketone or aldehyde (8) as described by F. Kunckel, *Ber.*, 34, 637, (1901).

Compounds of Formula (1) wherein $R^8$=$CH_2OH$ can be prepared as shown in equation e). The imidazoles (1) were prepared as described in L. A. Reiter, *J. Org. Chem.*, 52, 2714 (1987). Hydroxymethylation of (1) as described by U. Kempe, et al. in U.S. Pat. No. 4,278,801 provides the hydroxymethylimidazoles (1a).

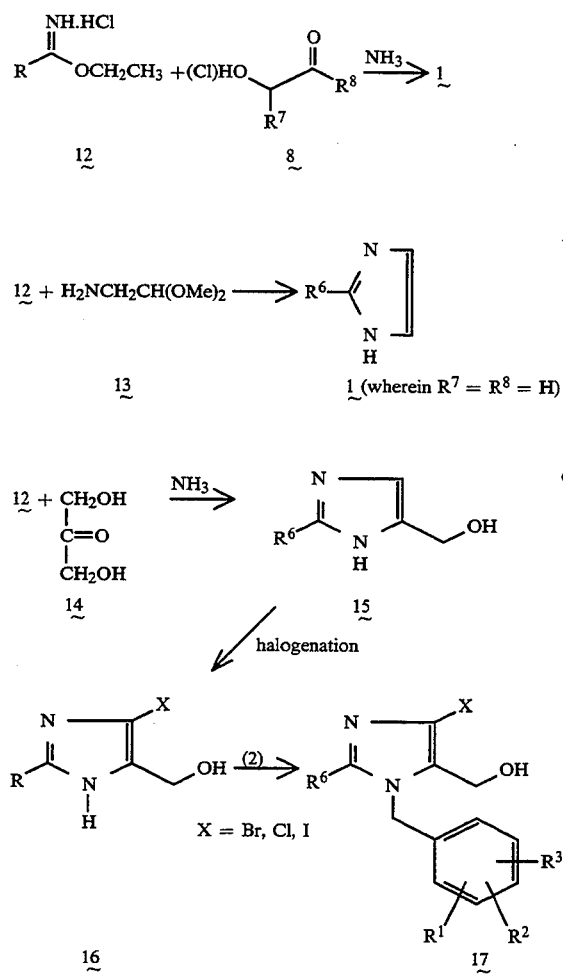
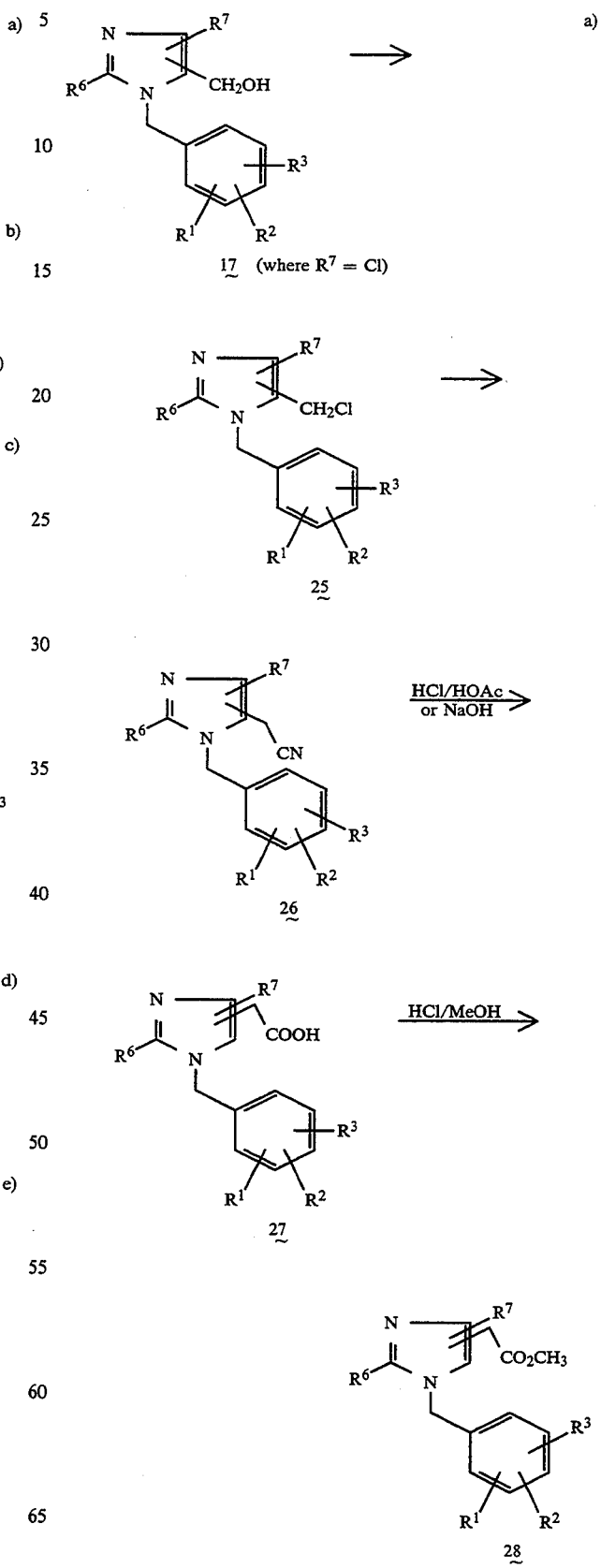

-continued
Scheme 3

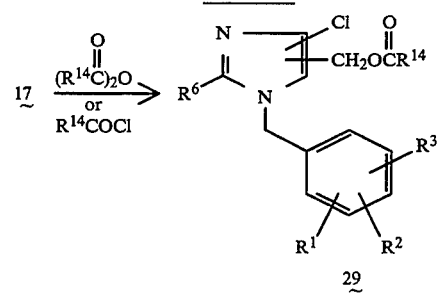

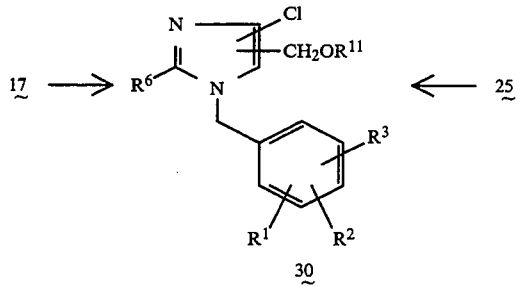

As shown in Scheme 3, path a) for benzylimidazoles (17) where $R^8$=$CH_2OH$, the hydroxymethyl groups may be easily converted to the corresponding halide, mesylate or tosylate by a variety of methods familiar to one skilled in the art. Preferably, the alcohol (17) is converted to the chloride (25) with thionyl chloride in an inert solvent at temperatures of 20° C. to the reflux temperature of the solvent.

Chloride (25) may be displaced by a variety of nucleophiles by nucleophilic displacement reaction procedures familiar to one skilled in the art. For example, excess sodium cyanide in DMSO may be used to form cyanomethyl derivatives (26) at temperatures of 20° C. to 100° C.

Nitrile (26) may be hydrolyzed to an acetic acid derivative (27), by a variety of methods. These methods include methods described previously for the hydrolysis of nitriles of formula (9). Examples of desired acids and bases for this hydrolysis include mineral acids such as sulfuric acid, hydrochloric acid, and mixtures of either of the above with 30-50% acetic acid (when solubility is a problem), and alkali metal hydroxides such as sodium hydroxide or potassium hydroxide. The hydrolysis reaction proceeds under heating at temperatures ranging from 50°-160° C. for 2-48 hours. Carboxylic acid (27) may be esterified by a variety of methods without affecting other parts of the molecule. Preferably, (27) is refluxed in a hydrochloric acid/methanol solution for 2-48 hours to give ester (28).

Ester (28) may be hydrolyzed to carboxylic acid (27), for instance, after $R^1$, $R^2$ and $R^3$ have been elaborated. Various methods, acidic or basic, may be used. For example, compound (28) is stirred with 0.5N potassium hydroxide in methanol, or if base soluble, it is stirred in 1.0N sodium hydroxide for 1-48 h at 20° C. to reflux temperatures.

Hydroxymethyl derivative (17) may be acylated to give (29) by a variety of procedures. As shown in path b) acylation can be achieved with 1-3 equivalents of an acyl halide or an anhydride in a solvent such as diethyl ether, tetrahydrofuran, methylene chloride or the like in the presence of a base such as pyridine or triethylamine. Alternatively (17) may be acylated by reaction with a carboxylic acid and dicyclohexylcarbodiimide (DCC) in the presence of a catalytic amount of 4-(N,N-dimethylamino)pyridine (DMAP) via the procedure described by A. Hassner, Tet. Lett., 46, 4475 (1978). Treatment of (17) with a solution of carboxylic acid anhydride in pyridine optionally with a catalytic amount of DMAP at temperatures of 20°-100° C. for 2-48 hours is the preferred method.

The ether (30) can be prepared from the alcohol (17) as shown in path c) by methods such as treatment of (17) in a solvent such as dimethylformamide or dimethylsulfoxide with potassium t-butoxide, sodium hydride, or the like followed by treatment with $R^{11}L$ at 25° C. for 1-20 hours, where L is a halogen, tosylate or mesylate.

Alternatively, treatment of (17) with 1-5 equivalents of thionyl chloride in chloroform for 2-6 hours at 25° C. followed by treatment of the intermediate (25) with 1-3 equivalents of $MOR^{11}$, where M is sodium or potassium, for 2-10 hours at 25° C. either in $R^{11}OH$ as solvent or in a polar solvent such as dimethylformamide or the like will also yield ether (30).

The ether (30) can also be prepared for example by heating (17) for 3-15 hours at 60°-160° C. in $R^{11}OH$ containing an inorganic acid such as a hydrochloric acid or sulfuric acid.

N-arylimidazoles of formula I (compounds wherein r=o) can be prepared by the following methods, it being understood by one skilled in the art that certain manipulations, protecting and deprotecting steps, and other synthetic procedures disclosed above may be necessary to produce compounds with the desired combinations of $R^6$, $R^7$, $R^8$ and $R^{13}$.

As shown in Scheme 4, equation a) the reaction of aniline derivative (34) with imidate ester (12) to form the substituted amidine (35) provides material which can be cyclized with dihydroxyacetone to form structure (36). Subsequent elaboration into (I) provides the N-arylimidazole compounds of the invention.

Alternatively as shown by equation b) the Marckwald procedure, described by Marckwald et al., Ber., 22, 568, 1353 (1889); Ber., 25, 2354 (1892) can form a 2-mercaptoimidazole (38) from aniline derivative (34) via isothiocyanate (37). Desulfurization of (38) with dilute nitric acid followed by anion formation at the 2-position of the imidazole (39) and reaction with $R^6X$ where X is Cl, Br, I, allows the formation of (40) which can be subsequently elaborated to I.

A variation of Marckwald's process as shown in equation c) using an α-aminoketone (41) and isothiocyanate (37) can also be employed, see Norris and McKee, J. Amer. Chem. Soc., 77, 1056 (1955) can also be employed. Intermediate (42) can be converted to (I) by known sequences. The general procedure of Carboni et al., J. Amer. Chem. Soc., 89, 2626 (1967) (illustrated by equation d)) can also be used to prepare N-aryl substituted imidazoles from appropriate haloaromatic compounds (43; X=F, Cl, Br) and imidazoles (1):

5,354,867
Scheme 4
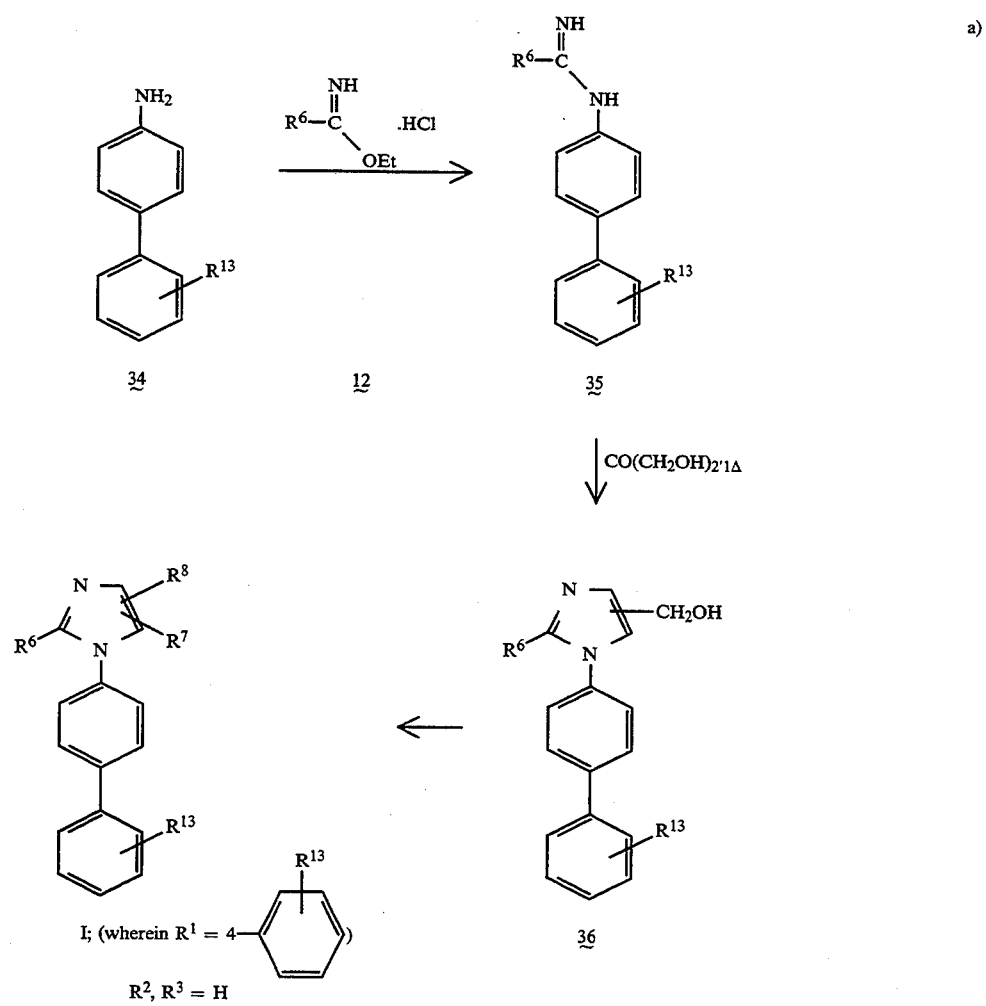
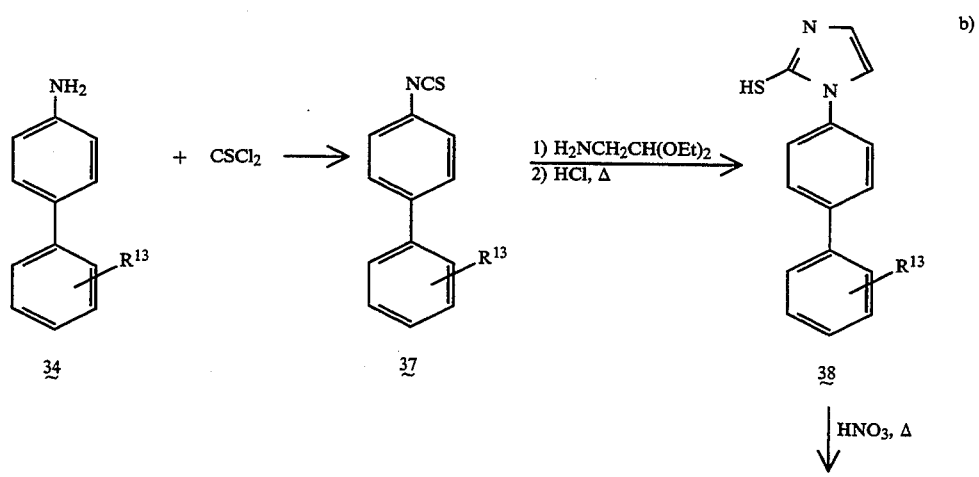

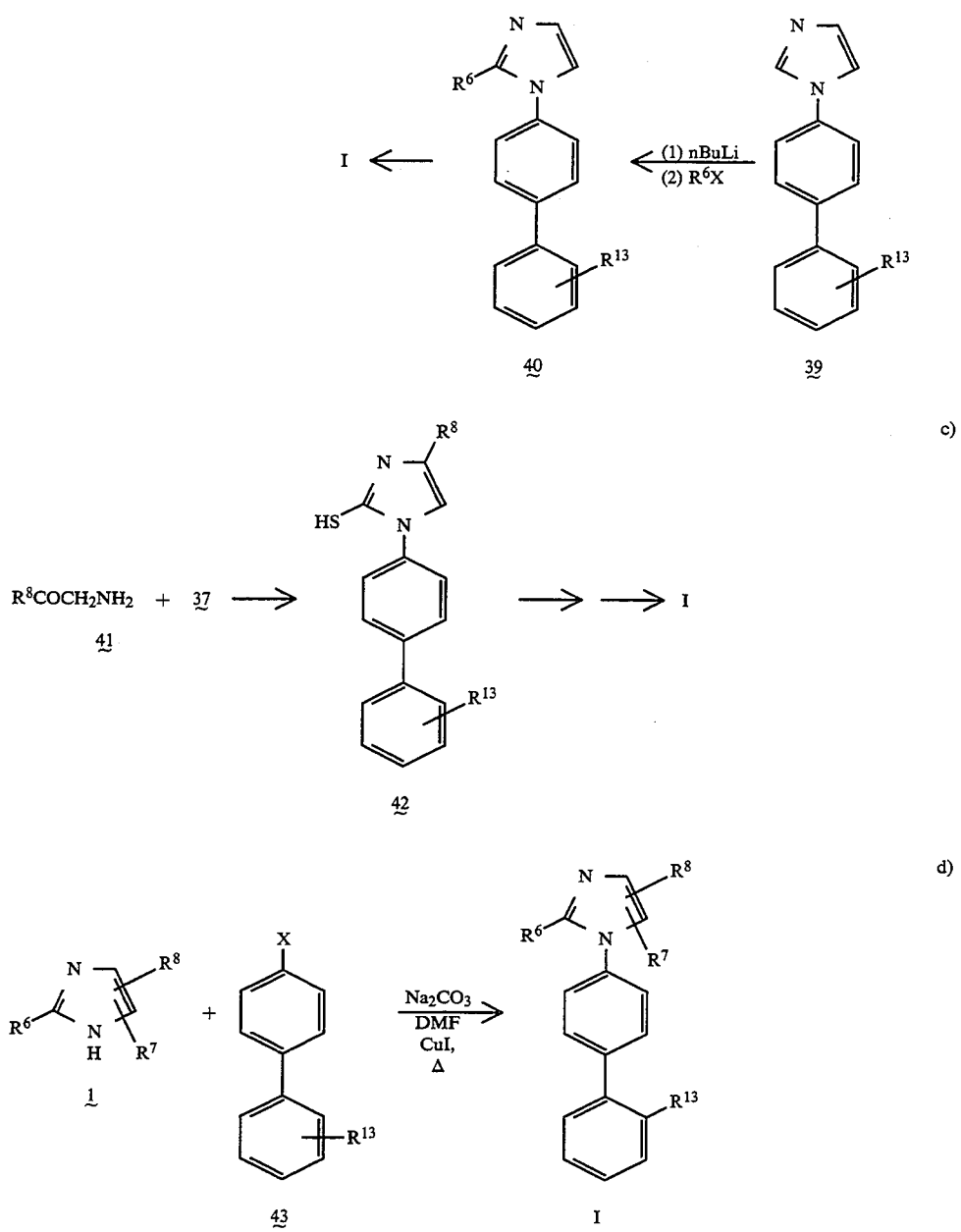
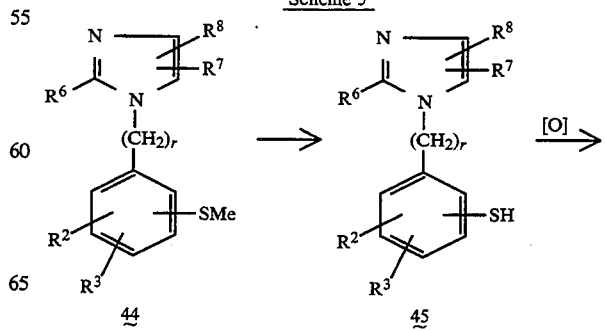
In various synthetic routes $R^1$, $R^2$ and $R^3$ do not necessarily remain the same from the starting compound to the final products, but are often manipulated through known reactions in the intermediate steps as shown in Schemes 5-22. All of the transformations shown in Schemes 5-10 and 12 can also be carried out on the terminal aromatic ring (i.e., biphenyl ring).

-continued
Scheme 5

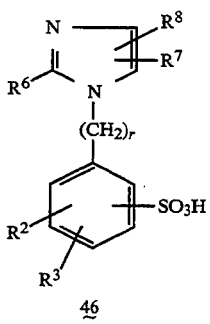

As shown in Scheme 5, compounds where $R^1$ is a sulfonic acid group may be prepared by oxidation of the corresponding thiol (45). Thus, an N-benzylimidazole derivative bearing a thiol group may be converted into a sulfonic acid (46) by the action of hydrogen peroxide, peroxyacids such as metachloroperoxybenzoic acid, potassium permanganate or by a variety of other oxidizing agents, E. E. Reid, *Organic Chemistry of Bivalent Sulfur*, 1, Chemical Publishing Co., New York, 120–121 (1958).

Aromatic hydroxy or thiol groups are obtained from deprotection of the corresponding alkyl ether or thioethers. Thus, for example, a methyl ether or a methyl thioether derivative (44) of an N-benzylimidazole containing one or more aromatic rings may be converted into the free phenol or thiophenol (45) by the action of boron tribromide methyl sulfide, P. G. Willard and C. F. Fryhle, *Tet. Lett.*, 21, 3731 (1980); trimethylsilyl iodide, M. E. Jung and M. A. Lyster, *J. Org. Chem.*, 42, 3761 (1977); KSEt and derivatives thereof, G. I. Feutrill, R. N. Mirrington, *Tet. Lett.*, 1327, (1970), and a variety of other reagents.

Alternatively, N-benzylimidazoles may be sulfonated by stirring with $H_2SO_4$ at a variety of different concentrations or with other sulfonating agents such as chlorosulfonic acid or sulfur trioxide with or without complexing agents such as dioxane or pyridine at temperatures from 0° to 200° C. with or without solvent, K. LeRoi Nelson in *Friedel-Crafts and Related Reactions*, III part 2, G. A. Olah, ed., Interscience Publ., 1355 (1964).

The synthesis of compounds where $R^1$ is a sulfate, phosphate or phosphonic acid are depicted in Scheme 6:

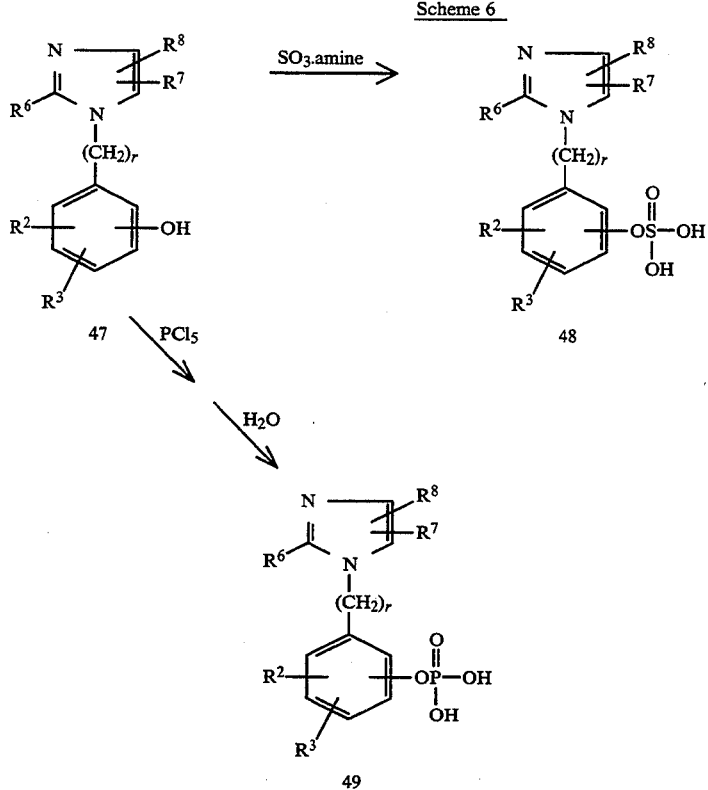

-continued
Scheme 6
b)
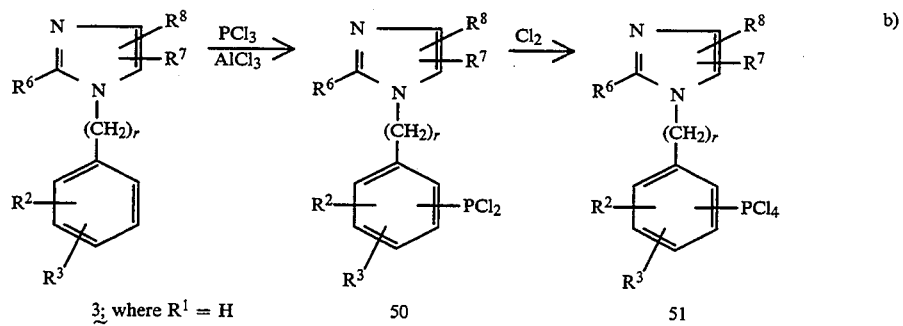
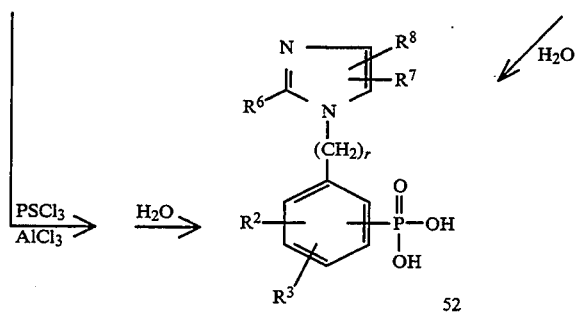
c)
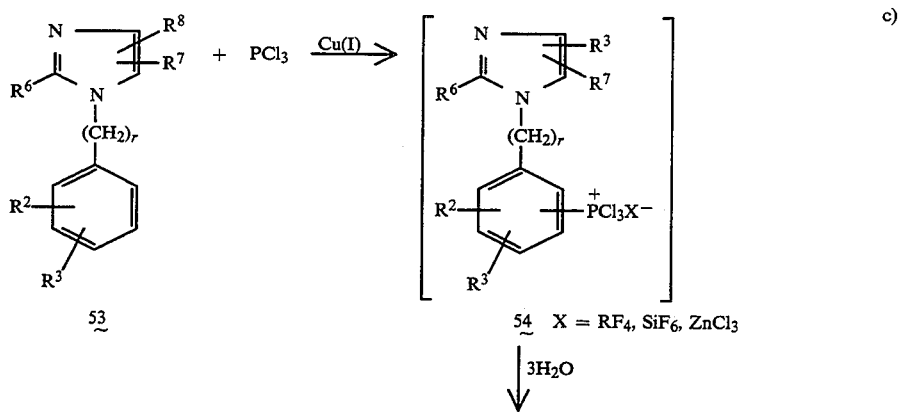
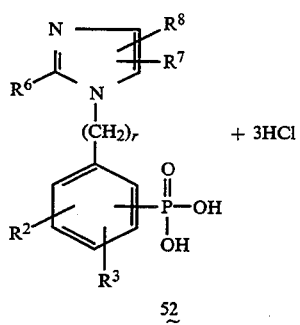

Scheme 6

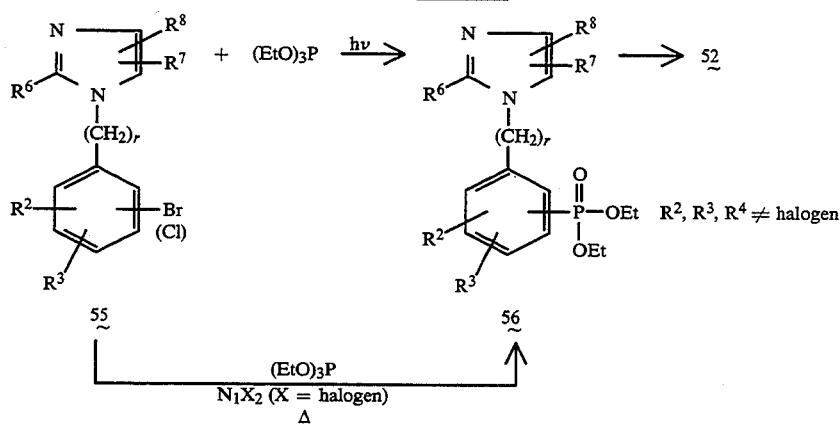

N-Benzylimidazoles containing a phenolic hydroxyl group (47) may be readily converted into the corresponding sulfate (48) or phosphate (49). As shown in equation a), reaction of the phenol with a sulfur trioxide-amine complex will give the corresponding sulfate (48), E. E. Gilbert, *Sulfonation and Related Reactions*, Interscience, New York, chapter 6 (1965). Reaction of the phenol (47) with phosphorus pentachloride followed by hydrolysis will give the corresponding phosphate (49), G. M. Kosolapoff, *Organophosphorus Compounds*, John Wiley, New York, 235 (1950).

As shown in equation b) N-benzylimidazoles may be converted into the corresponding phosphonic acids by reaction with phosphorus trichloride ($PCl_3$) and aluminum chloride ($AlCl_3$) in an inert solvent for 0.5–96 hours from temperatures of 25° C. to the reflux temperatures of the solvent. Appropriate workup followed by reaction with chlorine ($Cl_2$) and subsequent hydrolysis of the tetrachloride (51) gives the phosphonic acid derivative (52), G. M. Kosolapoff in *Org. Reactions*, 6, R. Adams, editor, John Wiley and Sons, New York, 297 (1951). Another more direct route involves reaction of the N-benzylimidazole with $PSCl_3$ and $AlCl_3$ followed by hydrolysis, R. S. Edmunson in *Comprehensive Organic Chemistry*, Vol. 2, D. Barton and W. D. Ollis editors, Pergamon Press, New York, 1285 (1979).

Alternatively, equation c) illustrates that aryl phosphonic acids (52) may be formed from reaction of the corresponding diazonium salt (53) with $PCl_3$ in the presence of Cu(I) followed by hydrolysis with water (ibid, p. 1286).

As shown in equation d), the aryl halides (55) may be photolyzed in the presence of phosphite esters to give phosphonate esters (56), R. Kluger, J. L. W. Chan, *J. Am. Chem. Soc.*, 95, 2362, (1973). These same aryl halides also react with phosphite esters in the presence of nickel or palladium salts to give phosphonate esters, P. Tavs, *Chem. Ber.*, 103, 2428 (1970), which can be subsequently converted to phosphonic acids (52) by procedures known to one skilled in the art.

N-Benzylimidazoles containing an aldehyde or ketone (57) may be reacted with a phosphorus trihalide followed by water hydrolysis to give α-hydroxyphosphonic acid derivatives, G. M. Kosolapoff, op. cit., 304, as shown in Scheme 7.

Scheme 7

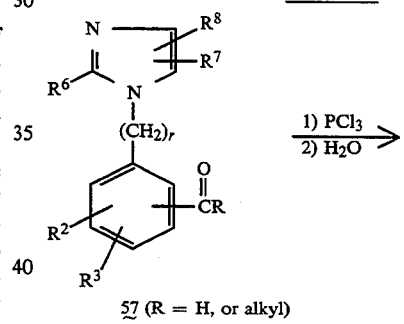

57 (R = H, or alkyl)

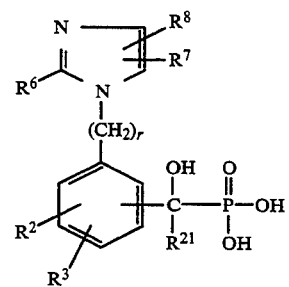

58

Compounds where $R^1$ is —$CONHOR^{12}$ may be prepared as shown in Scheme 8, by the treatment of a carboxylic acid (10) with 1–4 equivalents of thionyl chloride for 1–10 hours. This reaction can be run without solvent or in a nonreactive solvent such as benzene or chloroform at temperatures of 25°–65° C. The intermediate acid chloride is then treated with 2–10 equivalents of the appropriate amine derivative, $H_2N$—$OR^{12}$, for 2–18 hours at temperatures of 25°–80° C. in a polar aprotic solvent such as tetrahydrofuran or dimethylsulfoxide to give the hydroxamic acid (59).

Scheme 8

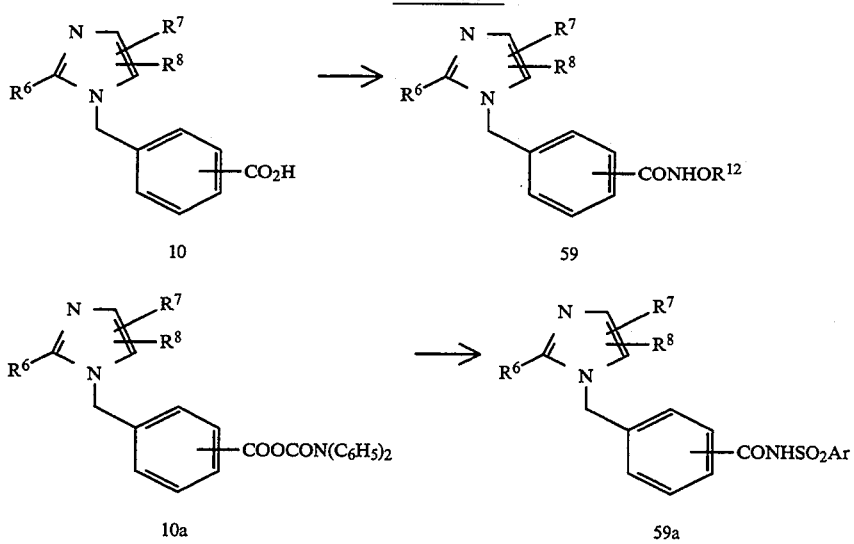

Alternatively, the carboxylic acid (10) can be converted to the hydroxamic acid (59) according to the procedure in J. Med. Chem., 28, 1158 (1985) by employing dicyclohexylcarbodiimide, 1-hydroxybenzotriazole, and H$_2$NOR$^{12}$ or according to the procedure described in Synthesis, 929 (1985) employing the Vilsmeier reagent and H$_2$NOR$^{12}$.

Compounds where R$^1$ is —CONHSO$_2$Ar (59a, Ar=-phenyl, o-tolyl, etc.) may be produced by treatment of the intermediate acid chlorides from the preparation of the hydroxamic acids (59), with ArSO$_2$NHNa. Alternatively, these acylsulfonamides (59a) can be prepared from the carboxylic acids (10) through the corresponding N,N-diphenylcarbamoyl anhydrides (10a) as described by F. J. Brown, et al. in Eur. Pat. Appl. EP 199543 (see Scheme 8).

Scheme 9

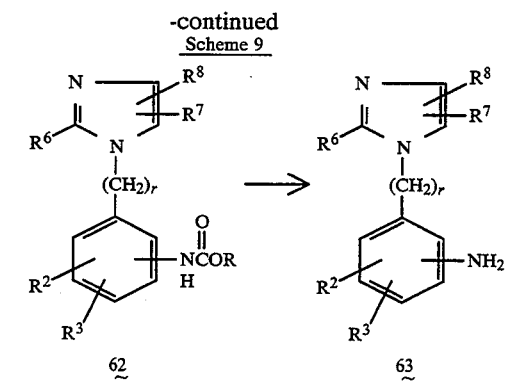

Aniline intermediates (63) are disclosed in U.S. Pat. No. 4,355,040 and may be obtained from the corresponding nitro compound precursor by reduction. A variety of reduction procedures may be used such as iron/acetic acid, D. C. Owsley, J. J. Bloomfield, Synthesis, 118, (1977), stannous chloride, F. D. Bellamy, Tet. Lett., 839, (1984) or careful hydrogenation over a metal catalyst such as palladium.

As shown in Scheme 9, aniline intermediates of N-benzylimidazoles may also be prepared from the corresponding carboxylic acid (10) or acid chloride via a Curtius rearrangement of an intermediate acyl azide (60). More modern methods include using diphenylphosphoryl azide as a source of azide, T. Shioiri, K. Ninomiya, S. Yamada, J. Am. Chem. Soc., 94, 6203 (1972), and trapping the intermediate isocyanate (61) produced by the Curtius rearrangement with 2-trimethylsilylethanol and cleaving the resultant carbamate (62) with fluoride to liberate the amine (63), T. L. Capson and C. D. Poulter, Tet. Lett., 25, 3515 (1984). Classical procedures familiar to one skilled in the art may also be employed.

Compounds where R$^1$ is —SO$_2$NH$_2$ may be made as shown in Scheme 10:

Scheme 10

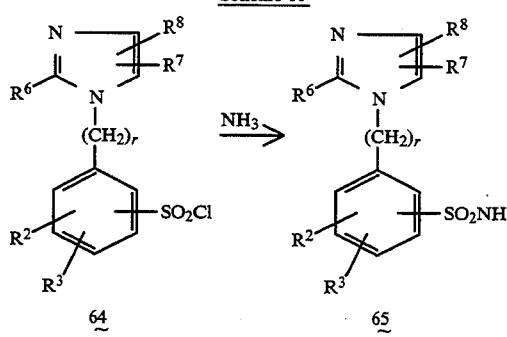

Sulfonamide compounds (65) may be made by reacting an arylsulfonyl chloride (64) with ammonia, or its equivalent. Unsubstituted arylsulfonamides are made by reaction with ammonia in aqueous solution or in an inert organic solvent, F. H. Bergheim and W. Braker, *J. Am. Chem. Soc.*, 65, 1459 (1944), or with dry powdered ammonium carbonate, E. H. Huntress and J. S. Autenrieth, *J. Am. Chem. Soc.*, 63, 3446 (1941); E. H. Huntress and F. H. Carten, *J. Am. Chem. Soc.*, 62, 511 (1940).

The sulfonyl chloride precursor may be prepared by chlorosulfonation with chlorosulfonic acid on the aromatic ring directly, E. H. Huntress and F. H. Carten, ibid.; E. E. Gilbert, op., cit., 84, or by reacting the corresponding aromatic diazonium chloride salt (53) with sulfur dioxide in the presence of a copper catalyst, H. Meerwein, et al., *J. Prakt. Chem.*, [ii], 152, 251 (1939), or by reacting the aromatic sulfonic acid (46) with $PCl_5$ or $POCl_3$, C. M. Suter, *The Organic Chemistry of Sulfur*, John Wiley, 459 (1948).

Linked ester compounds of formula (I) where $R^1$ is

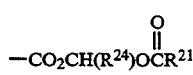

$$-CO_2CH(R^{24})OCR^{21}$$
$$\phantom{-CO_2CH(R^{24})}\overset{O}{\|}$$

can be made by procedures well known in penicillin and cephalosporin chemistry. The purpose is to provide materials which are more lipophilic and which will be useful orally by rapid transit from the gut into the bloodstream, and which will then cleave at a sufficiently rapid rate to provide therapeutically useful concentrations of the active carboxylic acid form. The following review articles and references cited therein discuss this concept and the chemistry involved in preparing such compounds V. J. Stella, et al., *Drugs*, 29, 455–473 (1985); H. Ferres, *Drugs of Today*. 19 (9), 499–538 (1983); A. A. Sirkula, *Ann. Repts. Med. Chem.*, 10, 306–315 (1975).

Experimental procedures which are applicable to the preparation of chemically stable linked esters are illustrated by equations a–e of Scheme 11.

Scheme 11

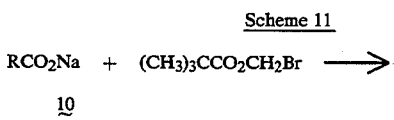

$$RCO_2Na + (CH_3)_3CCO_2CH_2Br \longrightarrow$$
10

$$RCO_2CH_2OCOC(CH_3)_3$$
66

G. Francheschi et al., *J. Antibiotics*, 36, (7), 938–941 (1983).

-continued
Scheme 11

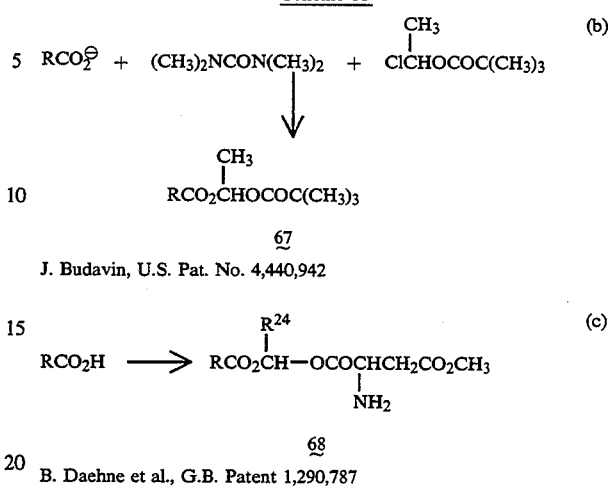

(b)

$$RCO_2^\ominus + (CH_3)_2NCON(CH_3)_2 + \underset{\underset{CH_3}{|}}{ClCHOCOC(CH_3)_3}$$

$$\downarrow$$

$$RCO_2\underset{\underset{CH_3}{|}}{CHOCOC(CH_3)_3}$$
67

J. Budavin, U.S. Pat. No. 4,440,942

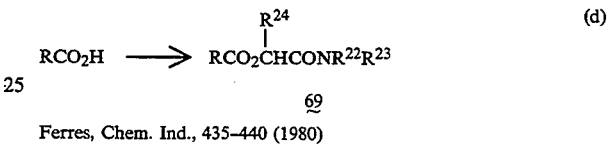

(c)

$$RCO_2H \longrightarrow RCO_2\underset{\underset{R^{24}}{|}}{CH}-OCOCHCH_2CO_2CH_3$$
$$\phantom{RCO_2H \longrightarrow RCO_2CH-OCOCH}\underset{NH_2}{|}$$
68

B. Daehne et al., G.B. Patent 1,290,787

(d)

$$RCO_2H \longrightarrow RCO_2\underset{\underset{R^{24}}{|}}{CH}CONR^{22}R^{23}$$
69

Ferres, *Chem. Ind.*, 435–440 (1980)

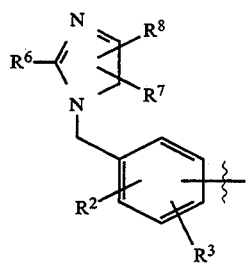

(e)

$$R-CO_2H \longrightarrow$$

70

Clayton et al., *Antimicrob. Agents Chemotherapy*, 5, (6), 670–671 (1974)

In equations a–e: R=

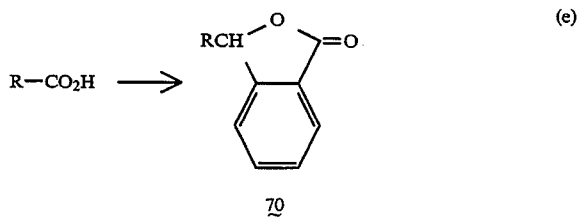

Compounds of Formula I where $R^1$ is $-C(CF_3)_2OH$ may be prepared as shown in Scheme 12.

Scheme 12

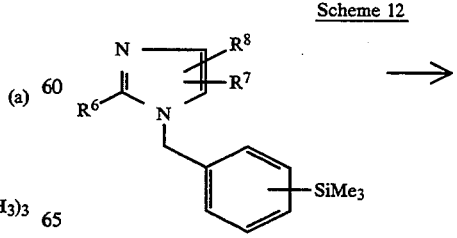

71

-continued
Scheme 12

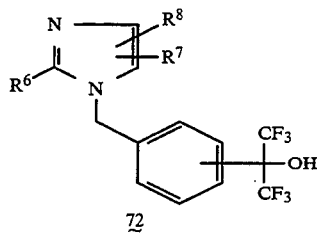

Hexafluoroisopropanol compounds (72) may be prepared by treatment of arylsilane (71) with 1–5 equivalents of hexafluoroacetone in a solvent such as methylene chloride at temperatures ranging from about −50° to 25° C. for a period of 2–10 hours. The requisite arylsilane (71) can be prepared using methods known to one skilled in the art such as the procedures described in Chapter 10 of Butterworth's "Silicon in Organic Chemistry".

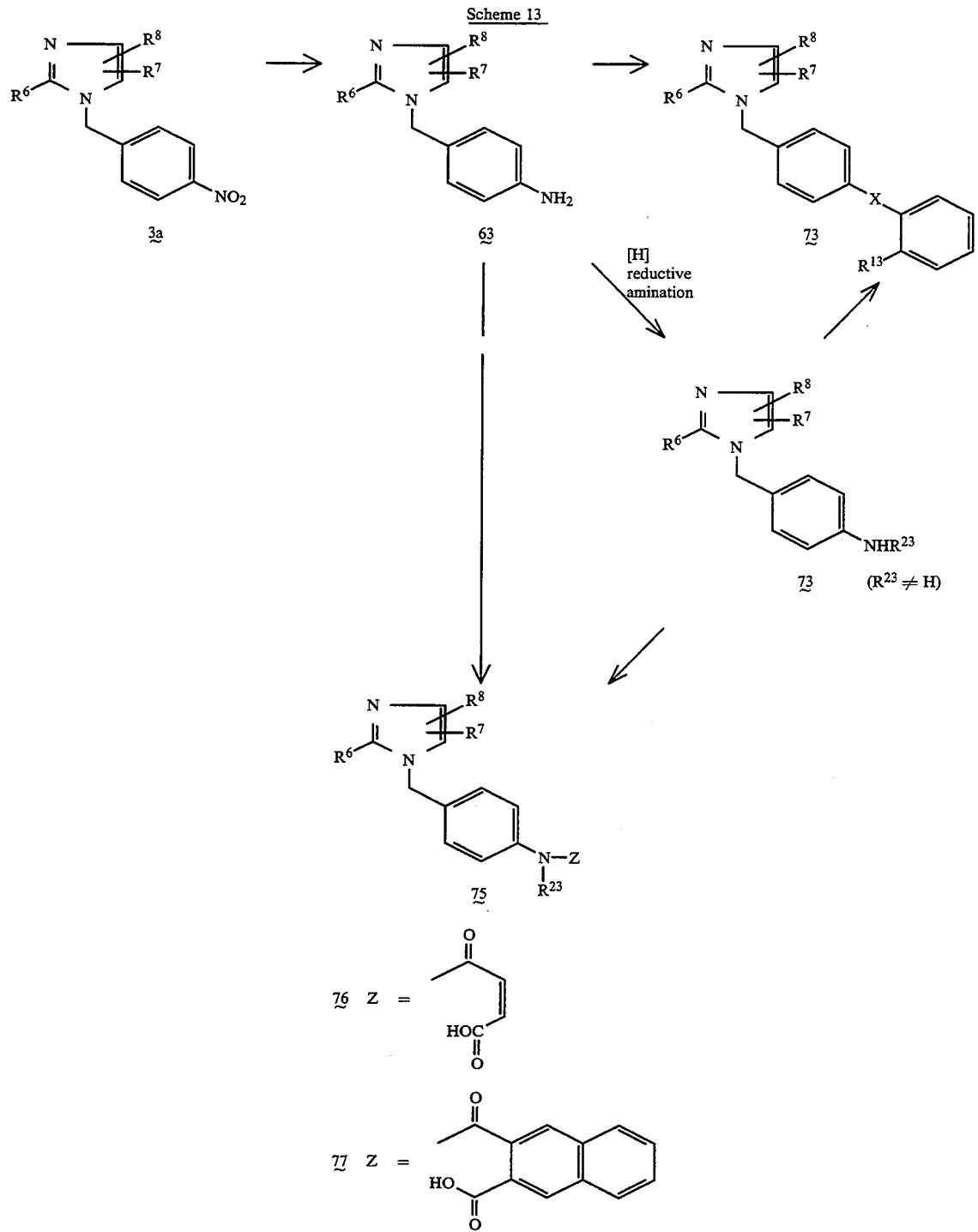

-continued
Scheme 13

78 Z = 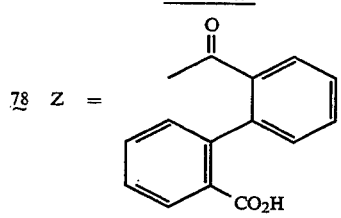

As shown in Scheme 13, compound (73) in which X=—NHCO and $R^{13}$=—COOH may be easily prepared, for example, by reacting aniline precursor (63) with a phthalic anhydride derivative tn an appropriate solvent such as benzene, chloroform, ethyl acetate, etc. Often the carboxylic acid product will precipitate from solution with the reactants remaining behind, M. L. Sherrill, F. L. Schaeffer, E. P. Shoyer, *J. Am. Chem. Soc.*, 50, 474 (1928).

When $R^{13}$=NHSO$_2$CH$_3$, NHSO$_2$CF$_3$ or tetrazolyl (or a variety of other carboxylic acid equivalents), compound (73) may be obtained by reacting aniline (63) with the requisite acid chloride by either a Schotten-Baumann procedure, or simply stirring in a solvent such as methylene chloride tn the presence of a base such as sodium bicarbonate, pyridine, or triethylamine.

Likewise, aniline (63) may be coupled with an appropriate carboxylic acid via a variety of amide or peptide bond forming reactions such as DCC coupling, azide coupling, mixed anhydride synthesis, or any other coupling procedure familiar to one skilled in the art.

Aniline derivatives (63) will undergo reductive amination with aldehydes and ketones to form secondary amines (74). Thus the aniline is first stirred with the carbonyl compound in the presence of a dehydration catalyst such as molecular sieves or p-toluenesulfonic acid. Afterwards the resultant imine is reduced to the amine with a borohydride reducing agent such as sodium cyanoborohydride or sodium borohydride. Standard catalytic hydrogenation reagents such as hydrogen and palladium/carbon can also be employed.

Alternatively, aniline (63) may be monoalkylated by reaction with ethyl formate followed by reduction with, for example, lithium aluminum hydride to produce the N-methyl derivative (74). Anilines (74) may in turn be reacted with carboxylic acid anhydrides and acid chlorides or carboxylic acids by any of the coupling procedures described previously to yield (73) where X=—N(CH$_3$)CO—.

Aniline (63) or (74) or other intermediate anilines where the amino group may be located on another aromatic ring for example, also react with other anhydrides to make amide-carboxylic acid derivatives of formula (75). Thus, for example, maleic anhydride, 2,3-naphthalenedicarboxylic acid anhydride, and diphenic anhydride are reacted in a similar fashion to phthalic anhydride with aniline (63) or (74) to yield carboxylic acids (76), (77), and (78), respectively.

Phthalimide derivatives of aniline (63) may be made by a variety of methods, preferably by stirring aniline (63) with phthalic anhydride in acetic acid at a temperature between 20° C. and reflux, G. Wanag, A. Veinbergs, *Ber.*, 75, 1558 (1942), or by stirring (63) with phthaloyl chloride, a base such as triethylamine, and an inert solvent.

Aniline (63) may be converted into its trifluoromethanesulfonamide derivative or its trifluoroacetamido derivative preferably by reacting it with triflic anhydride or trifluoroacetic anhydride and a base such as triethylamine in an inert solvent such as methylene chloride at −78° C. followed by warming to room temperature.

Compounds of structure (I) where X is a carbon-carbon linkage which are depicted as (80) can be made as shown in Scheme 14.

Scheme 14

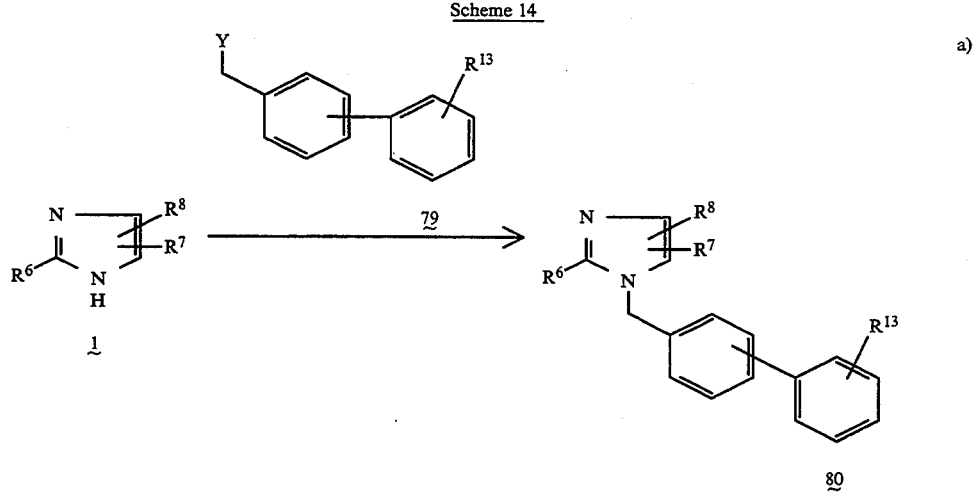

Y = Cl, Br, OTs, OMe

-continued
Scheme 14
b)
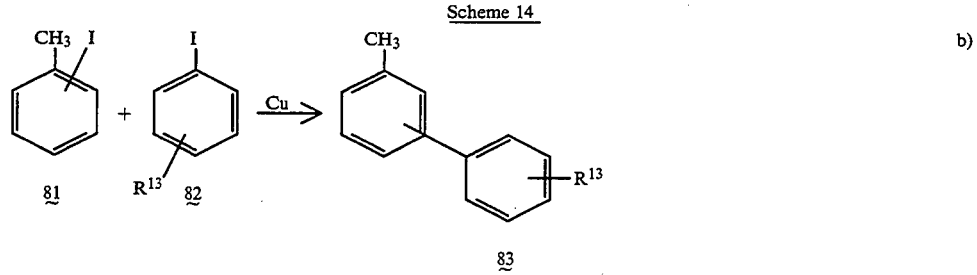
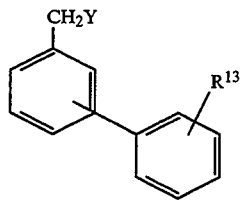
Y = Br, Cl
c)
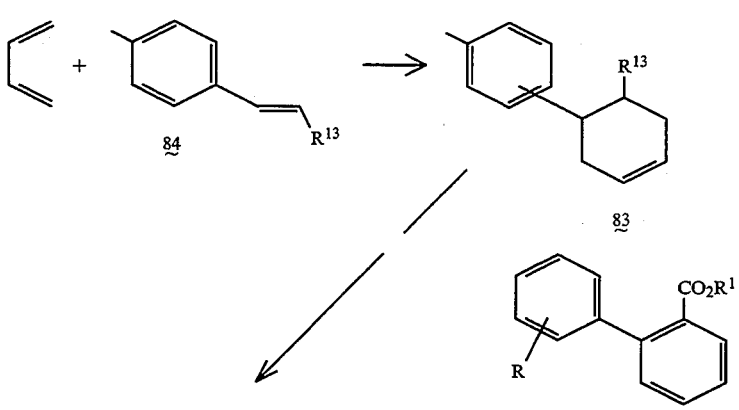
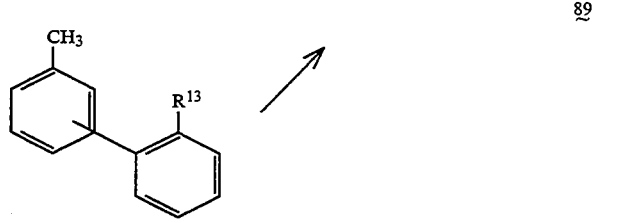
$R^1$ = CH$_3$Et, t-Bu, etc.
d)
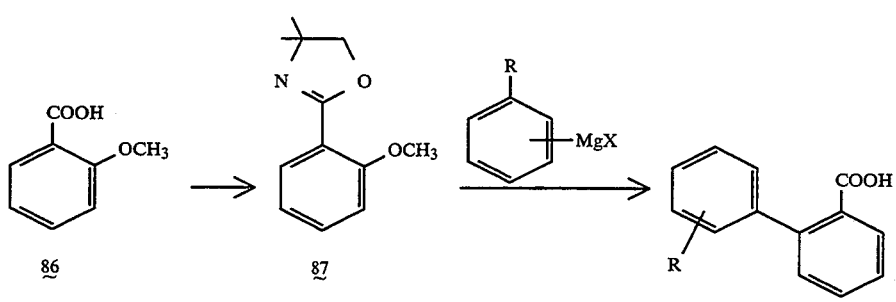

-continued
Scheme 14

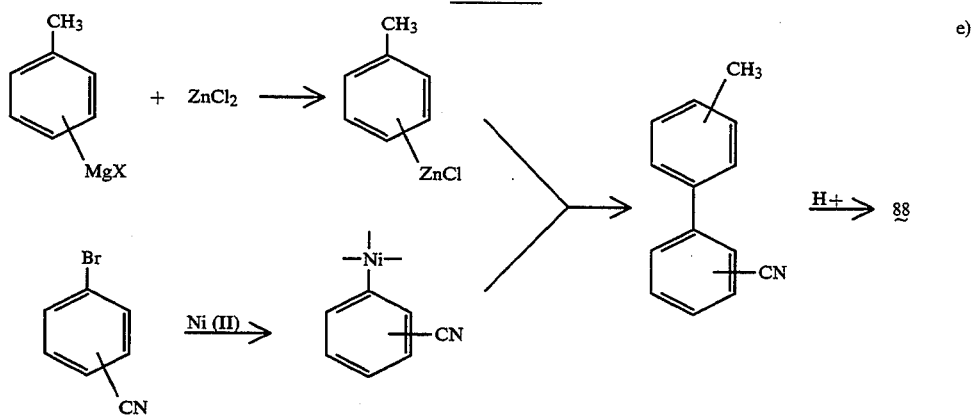

Equation a) illustrates that the biphenyl compounds (80) can be prepared by alkylation of imidazole (1) with the appropriate halomethylbiphenyl compound (79) by the general procedure described in Scheme 1.

The requisite halomethylbiphenyl intermediates (79) are prepared by Ullman Coupling of (81) and (82) as described in "Organic Reactions", 2, 6 (1944) to provide intermediates (83), which are in turn halogenated. Halogenation can be accomplished by refluxing (83) in an inert solvent such as carbon tetrachloride for 1–6 hours in the presence of a N-halosuccinimide and an initiator such as azobisisobutyronitrile (equation b).

As shown in equation c), derivatives of intermediate (83) in which $R^{13}$ is at the 2' position (83a) can also be prepared by the method described in J. Org. Chem., 41, 1320 (1976), that is Diels-Alder addition of a 1,3-butadiene to a styrene (84) followed by aromatization of intermediate (85).

Alternatively, the substituted biphenyl precursors (83; where $R^{13}$=COOH) and their esters (89) can be prepared as illustrated in equation d), which involves oxazoline compounds as key intermediates, A. I. Meyers and E. D. Mihelich, J. Am. Chem. Soc., 97, 7383 (1975).

Further, as shown in Equation e), nickel-catalyzed cross-coupling of an arylzinc halide with a halobenzonitrile yields a biphenylnitrile which can in turn be hydrolyzed by standard methods to afford acid 88.

The substituted biphenyl tetrazoles (83; where $R^{13}=$

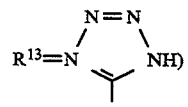

can be prepared from the nitrile precursors ($R^{13}$=CN) by the methods described in Scheme 1, equation c) and Scheme 15, equation c).

However, a preferred method for preparing tetrazoles is described in Scheme 15, equations a) and b). Compounds (90) may be prepared by the 1,3-dipolar cycloaddition of trialkyltin or triphenyltin azides to the appropriately substituted nitrile (83) as in equation a). Alkyl is defined as normal alkyl of 1–6 carbon atoms and cyclohexyl. An example of this technique is described by S. Kozima, et al., J. Organometallic Chemistry, 337 (1971). The required trialkyl or triaryltin azides are made from the requisite commercial trialkyl or triaryl tin chloride and sodium azide. The trialkyl or triaryltin group is removed via acidic or basic hydrolysis and the tetrazole can be protected with the trityl group by reaction with trityl chloride and triethylamine to give (91). Bromination as previously described herein with N-bromosuccinimide and dibenzoylperoxide affords compound (92). Alkylation of (1) with the appropriately substituted benzyl halide using conditions previously described followed by deprotection of the trityl group via hydrolysis affords (80; $R^{13}$=tetrazole). Other protecting groups such as p-nitrobenzyl and 1-ethoxyethyl can be used instead of the trityl group to protect the tetrazole moiety. These groups as well as the trityl group can be introduced and removed by procedures described in Greene, Protective Groups in Organic Synthesis, Wiley-Interscience, (1980).

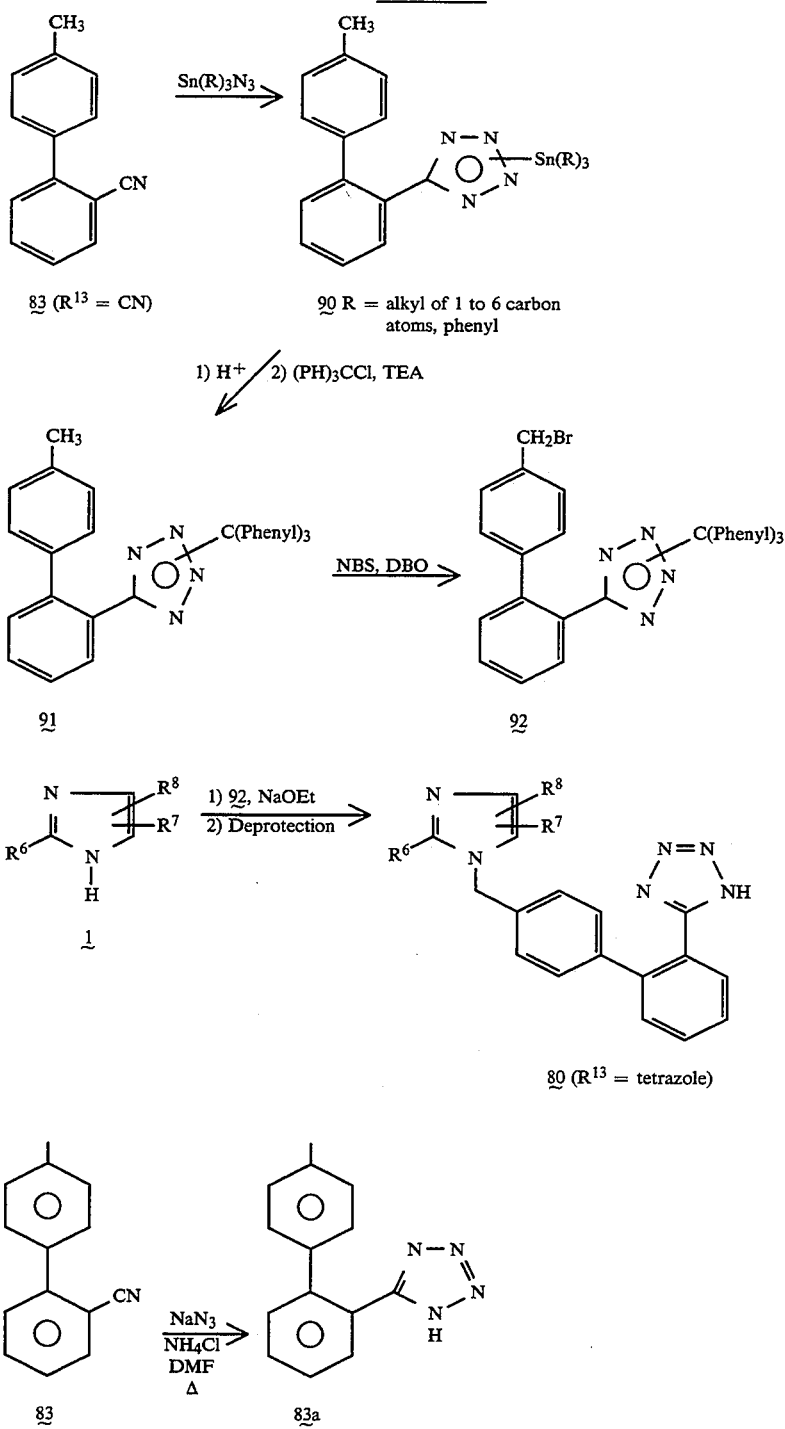
Compounds of structure 93-95 where X is an —O—, —S—, or
—N—
|
R[26]
linkage can be prepared as shown in Scheme 16 by alkylation of imidazole (1) with the appropriate benzyl halide (96).

Scheme 16

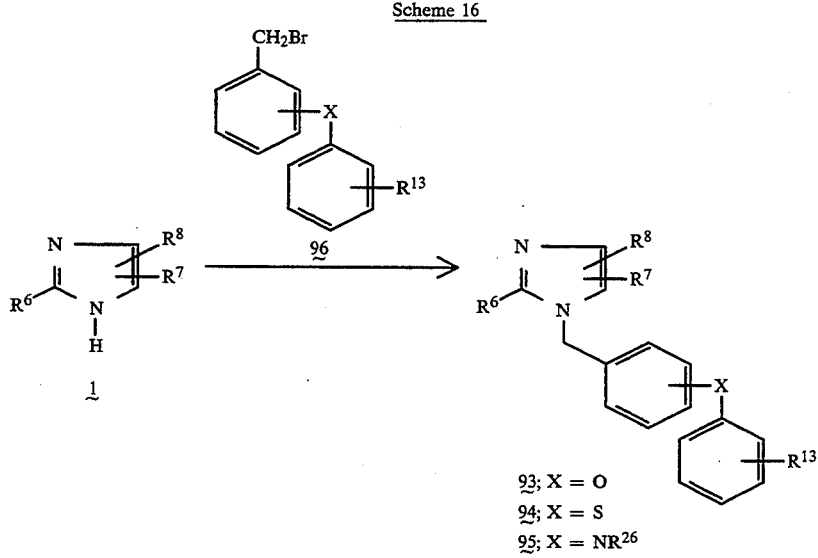

a)

93; X = O
94; X = S
95; X = NR²⁶

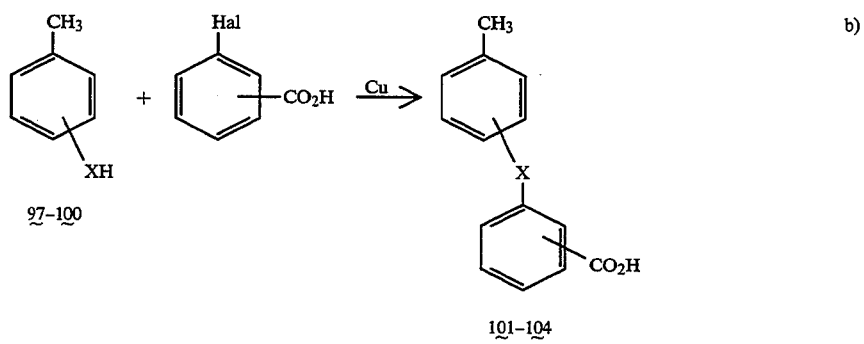

b)

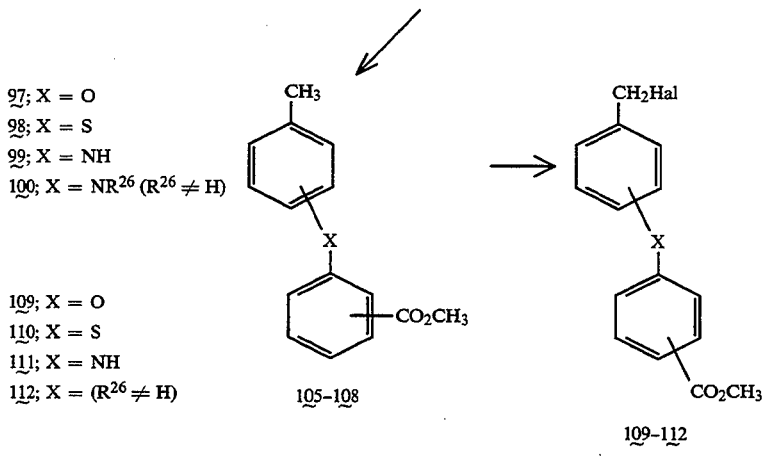

97; X = O
98; X = S
99; X = NH
100; X = NR²⁶ (R²⁶ ≠ H)

109; X = O
110; X = S
111; X = NH
112; X = (R²⁶ ≠ H)

The halomethyldiphenyl ether (109) employed as an alkylating agent in the present invention is prepared as shown in equation b). An Ullman ether condensation of the phenol (97) and a halobenzoic acid as described in Russian Chemical Reviews, 43, 679 (1974) provides the intermediate acid (101). The conversion of (101) into (109) is accomplished by esterification with diazomethane to afford (105) followed by halogenation employing the procedure used in the preparation of (79). The diphenylsulfide (110) and the diphenylamine (111) can be prepared from the appropriate thiophenol (98) or aniline (99) by this procedure.

The tertiary diphenylamine (112) can be prepared from the secondary aniline (100) by the above procedure. Alternatively (107) can be alkylated by one of the following procedures: 1) direct alkylation of (107) with $R^{26}L$ where L is a leaving group such as a halogen or tosylate employing phase-transfer conditions and ultrasound as described in Tetrahedron Letters, 24, 5907 (1983), 2) treatment of (107) with 1–1.5 equivalents of an appropriate aldehyde and 0.5–5.0 equivalents of sodium cyanoborohydride in a solvent such as methanol at 25° C. at a pH of 3–6 for 1–24 hours, or 3) reductive amination of (107) employing an appropriate carboxylic acid and sodium borohydride as described in J. Am. Chem. Soc., 96, 7812 (1974). The tertiary amine (108) is then halogenated by the procedure previously described to give (112).

Scheme 17

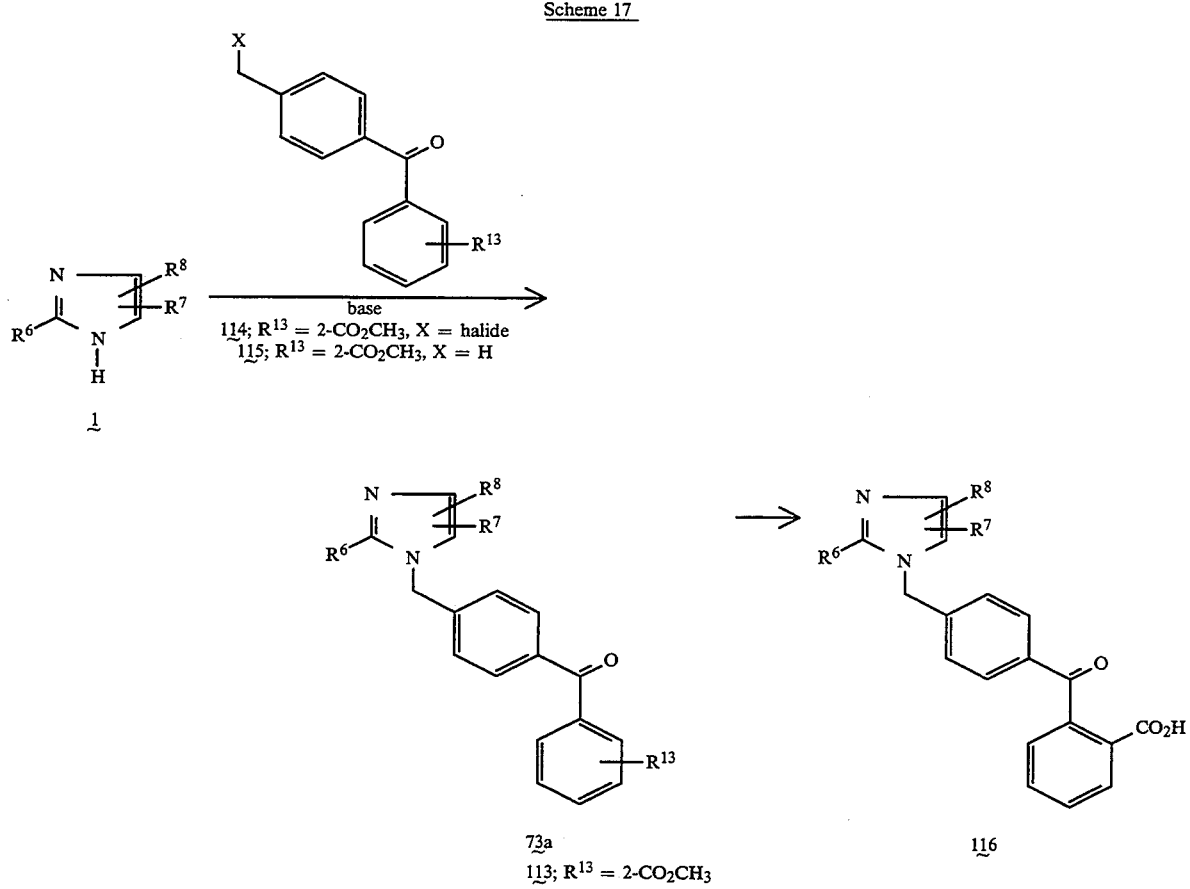

Compounds of structure (73) where X is —CO— are prepared as shown in Scheme 17 by alkylation of imidazole (1) with the requisite benzoylbenzyl halides. For example, esters (113) where $R^{13}$ is 2—$CO_2CH_3$ are prepared by alkylation of imidazole (1) with carbomethoxybenzoyl benzyl halide (114). Ester (113) may be hydrolyzed to the corresponding carboxylic acid (116) by a variety of methods including hydrolysis with a base such as sodium hydroxide or potassium hydroxide in an alcoholic aqueous solvent such as methanol/$H_2O$ at a temperature from 20° C. to the reflux temperature of the solvent.

Carboalkoxybenzoylbenzyl halides (114) are prepared by benzylic halogenation of the corresponding toluoylbenzene precursor by a variety of methods previously described herein. For example, methyl 2-(4-methylbenzoyl)benzoate (115) can be refluxed for 2–48 hours with N-bromosuccinimide, benzoyl peroxide and carbon tetrachloride to effect benzylic bromination.

Scheme 18

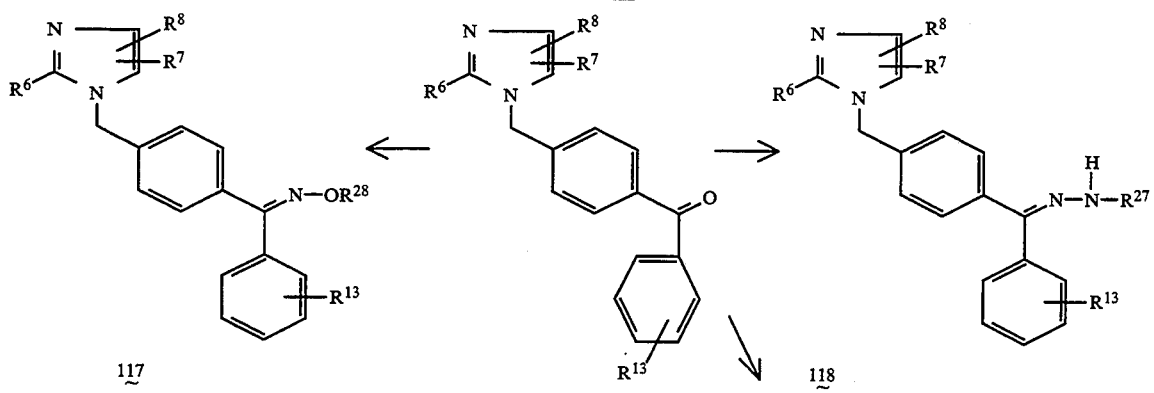

-continued

Scheme 18

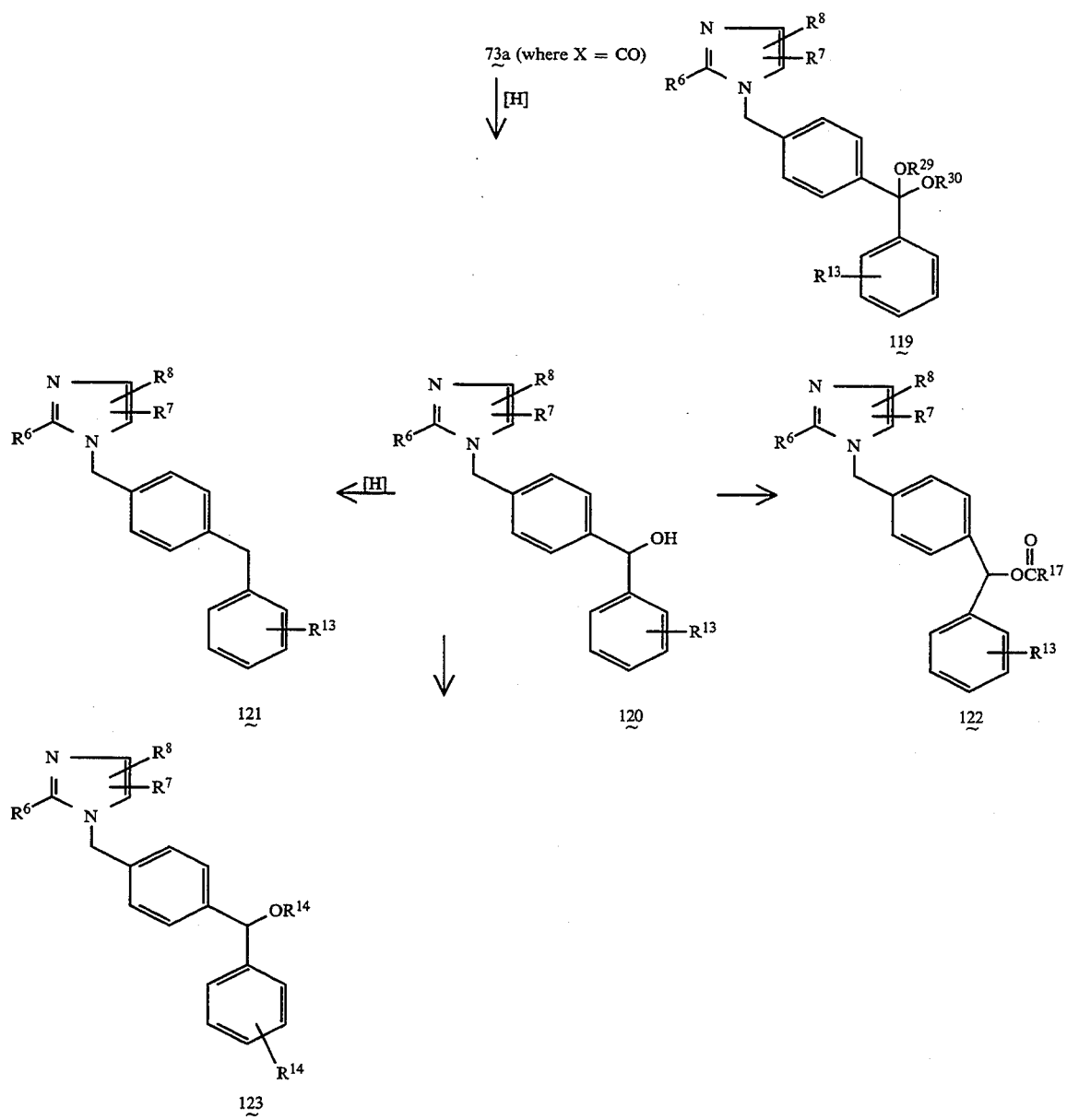

As shown in Scheme 18 the tolnoyl ketones (73; where X=CO) may be further transformed into a variety of ketone derivatives including compounds where X is

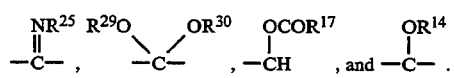

Reaction of ketone (73a) with a hydroxylamine or an appropriately substituted hydrazine will give the requisite oximes (117) and hydrazones (118). Reaction with alcohols in the presence of an acidic catalyst with removal of water will give ketals (119). Reduction, with lithium aluminum hydride, a metal borohydride, zinc/acetic acid or catalytic hydrogenation will give the corresponding alcohol (120) or fully reduced methylene compound (121). These alcohols may be acylated by a variety of anhydrides or acid halides in the presence of a base with or without solvent to give the corresponding esters (122). The alcohols (120) may be converted into their corresponding ethers (123) by reaction of the metal alkoxide with an alkyl halide, mesylate or tosylate in the appropriate solvent or by treatment with a mineral acid in an alcoholic solvent, or by reaction of the alcohol with diazomethane as described in G. Hilgetag and A. Martini, "Preparative Organic Chemistry", John Wiley, New York 355-368 (1972).

Compounds of formula (I) where X is —OCH$_2$—, —SCH$_2$—, and —NHCH$_2$— are prepared as shown in Scheme 19.

Scheme 19

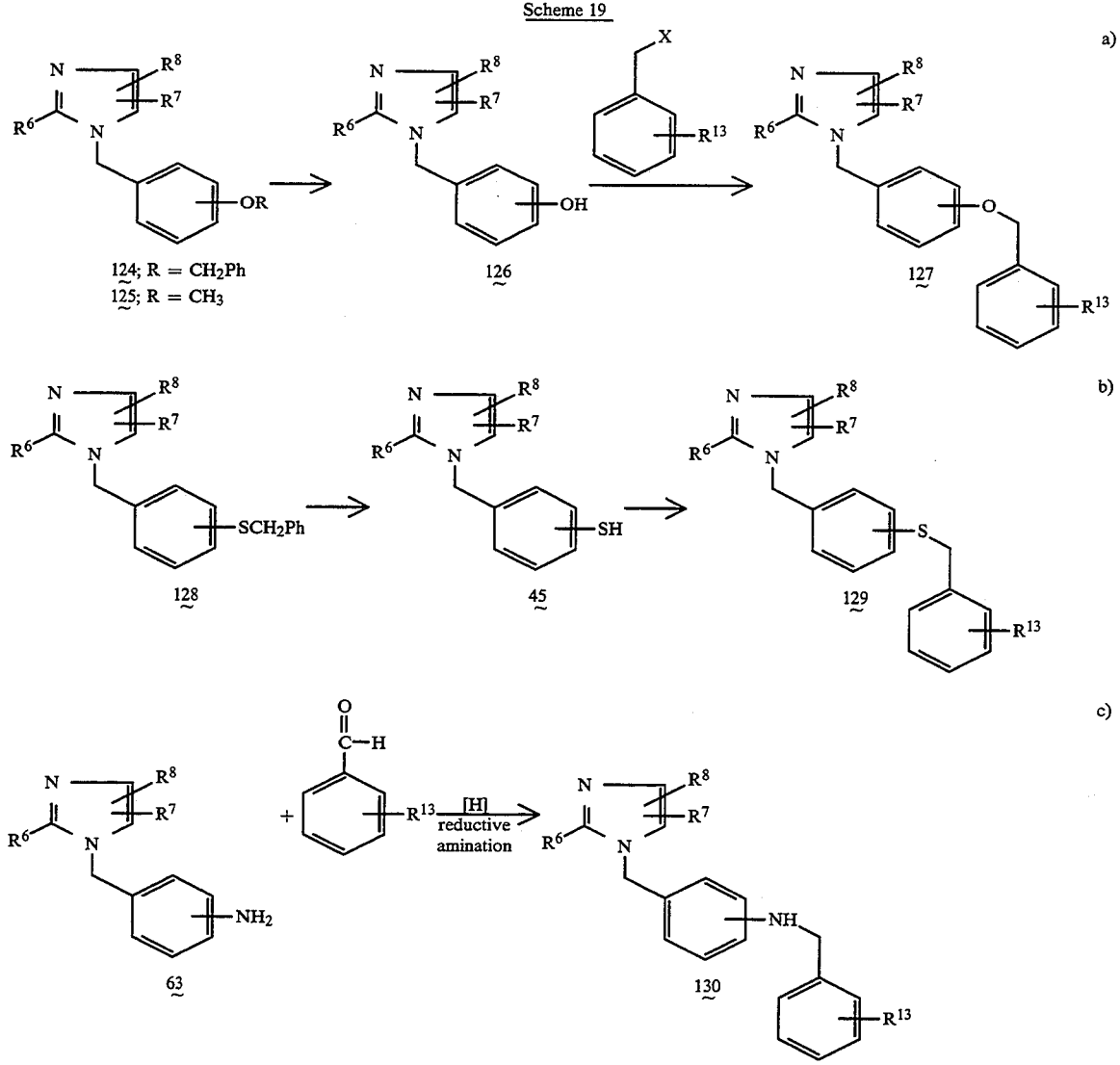

As illustrated in Scheme 19, equation a, hydrolysis of benzyl ether (124) or methyl ether (125) affords hydroxy compound (126) which can be alkylated with the appropriate benzyl halide to give (127). In the case of the methyl ethers (125), the hydrolysis step can be effected by heating the ether at temperatures of 50°–150° C. for 1–10 hours in 20–60% hydrobromic acid, or heating at 50°–90° C. in acetonitrile with 1–5 equivalents of trimethylsilyl iodide for 10–50 hours followed by treatment with water. Hydrolysis can also be carried out by treatment with 1–2 equivalents of boron tribromide in methylene chloride at 10°–30° C. for 1–10 hours followed by treatment with water, or by treatment with an acid such as aluminum chloride and 3–30 equivalents of a sulfur-containing compound such as thiophenol, ethanedithiol, or dimethyl disulfide in methylene chloride at 0°–30° C. for 1–20 hours followed by treatment with water. For compound (124), hydrolysis can be accomplished by refluxing in trifluoroacetic acid for 0.2–1 hours or by catalytic hydrogenolysis in the presence of a suitable catalyst such as 10% palladium on carbon. Deprotonation of (126) with a base, such as sodium methoxide, sodium hydride or the like in a solvent such as dimethylformamide or dimethylsulfoxide at room temperature followed by alkylation with an appropriate benzyl halide at 25° C. for 2–20 hours affords ethers of formula (127), as shown in equation a.

The sulfide (129) can be prepared from the thiophenol (45) by the procedure described above to prepare the ether (127) from the phenol (126). The thiophenol (45) can be prepared for example by treatment of the benzylsulfide (128) with sodium in liquid ammonia.

The amine (130) can be prepared as shown in equation c, from the aniline (63), itself available from reduction of the corresponding p-nitro compound (3a) which has previously been described. The reductive amination can be carried out by the same procedure as described in Scheme 13 for the preparation of compound (74).

Compounds of Formula (I) where the X linkage is —CH=CH—, —CH$_2$CH$_2$— and

A are prepared as shown in Scheme 20.

Scheme 20

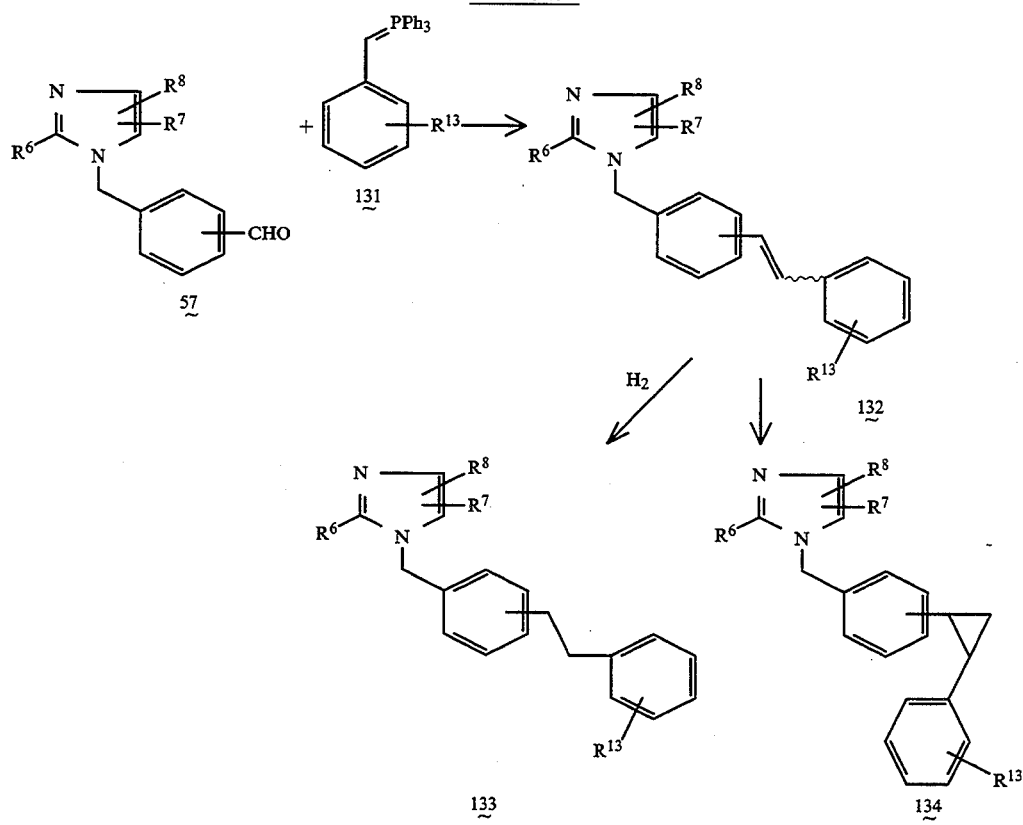

The cis or trans stilbene (132) can be obtained by employing a Wittig reaction between the aldehyde (57) and the phosphorane (131).

The stilbene (132) can readily be converted to the saturated derivative (133) for example by catalytic hydrogenation employing a heterogeneous catalyst such as palladium/carbon or platinum/carbon or alternatively with a homogeneous catalyst such as tristriphenylphosphine rhodium chloride. The reduction is performed in a solvent such as benzene, tetrahydrofuran or ethanol at 25° C. under 1-3 atmospheres of hydrogen for 1-24 hours.

The cyclopropane (134) can be prepared by treating the stilbene (132) with the Simmons-Smith reagent as described in *J. Am. Chem. Soc.*, 81, 4256 (1959), or by treating (132) with methylene diiodide and copper powder as described in *J. Am. Chem. Soc.*, 101, 2139 (1979), or by treatment with the iron-containing methylene-transfer reagent described in *J. Am. Chem. Soc.*, 101, 6473 (1979).

The preparation of compounds of formula (I) where X is —CF$_2$CH$_2$—, —CF=CH—, —CH=CF—, —CF=CF— and —CF$_2$CF$_2$— are depicted in Scheme 21.

Scheme 21

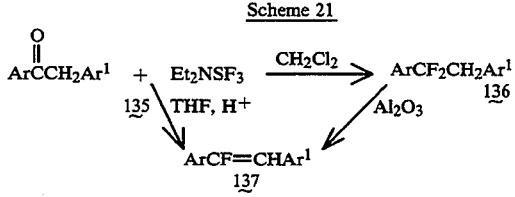

-continued
Scheme 21

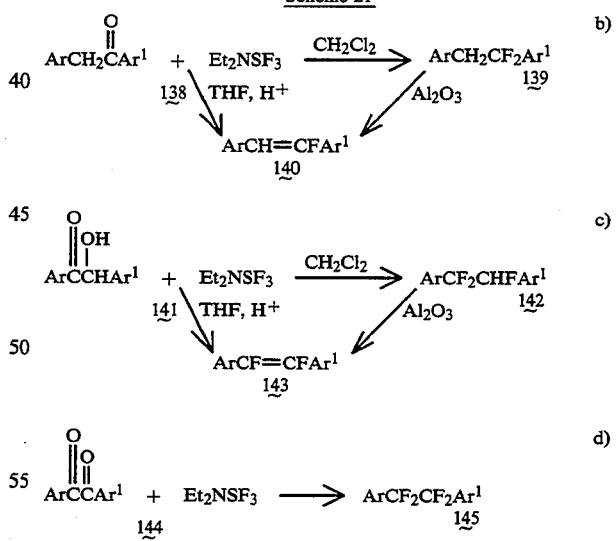

Vinylene fluorides (137) and (140) can be prepared by reaction of SF$_4$ or Et$_2$NSF$_3$ (DAST) with the appropriate ketone (135) or (138) in which Ar bears a methyl group convertible to a benzylic halide suitable for attachment to an imidazole nitrogen, and Ar' bears a cyano, nitro, ester, or other suitable group which can be subsequently converted to CO$_2$H, NHSO$_2$CF$_3$, etc. The initially formed difluoroethylene (136) and (139) can be formed in a non-polar solvent such as methylene chloride and subsequently converted to the vinylene fluoride by means of alumina, or converted directly into the unsaturated fluoride by running the reaction in a polar solvent such as tetrahydrofuran, diglyme or N-methylpyrrolidone in the presence of mineral acid. [Equations a and b]. Experimental details of such procedures are found in D. R. Strobach and G. A. Boswell, *J. Org. Chem.*, 36, 818 (1971); G. A. Boswell, U.S. Pat. No. 3,413,321 (1968) and U.S. Pat. No. 4,212,515 (1980).

As shown in equation c) an appropriate benzoin (141) may be similarly converted to the corresponding 1,2-difluorostilbene (143). Likewise as shown in equation d) an appropriate benzil (144) can be converted to a tetrafluorodiarylethylene (145) using DAST or $SF_4$. Experimental details are described in M. E. Christy. et al., *J. Med. Chem.*, 20, (3), 421–430, (1977).

Compounds of formula 1 where X=

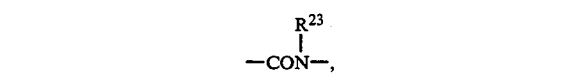

—$CH_2O$—, —$CH_2S$—, —$CH_2NH$—, can be made as shown in Scheme 22.

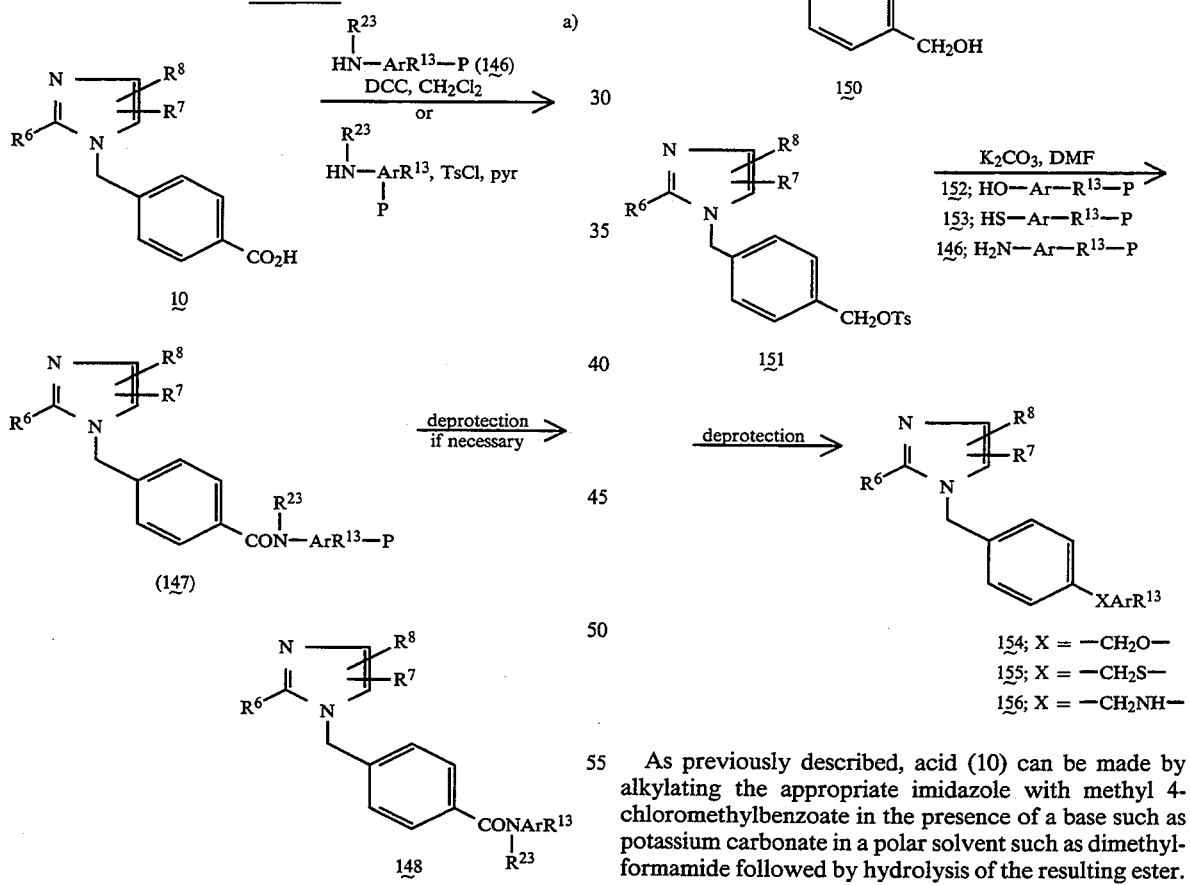

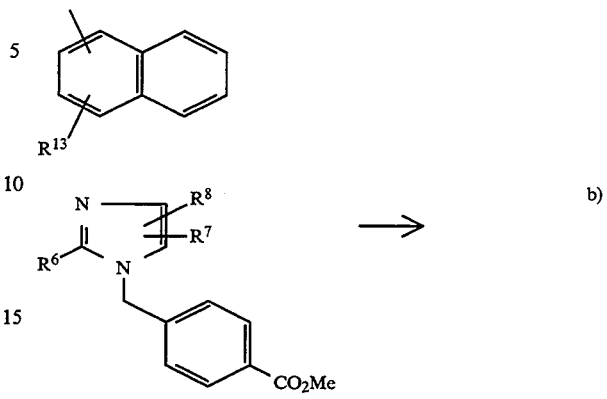

P = protecting group (if necessary)

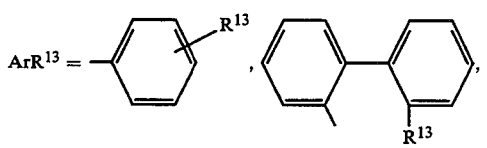

As previously described, acid (10) can be made by alkylating the appropriate imidazole with methyl 4-chloromethylbenzoate in the presence of a base such as potassium carbonate in a polar solvent such as dimethylformamide followed by hydrolysis of the resulting ester. Compound (10) can be converted to (148) by reaction with the requisite amine (146) ($R^{13}$ may need to be protected and subsequently deprotected) and dicyclohexyl carbodiimide (DCC) in methylene chloride [J. R. Beek, et al., *J. Am. Chem. Soc*, 90, 4706 (1968)] or by reaction with tosyl chloride in pyridine [J. H. Brewster and C. J. Ciotti, Jr., *J. Am. Chem. Soc.*, 77, 6214 (1955)]. Yet another process involves conversion of carboxylic acid (10) to its acid chloride with, for example, thionyl chloride followed by reaction with the amine in aqueous base (Schotten-Baumann conditions) or in an organic solvent in the presence of an acid scavenger such as NaHCO$_3$, pyridine or triethylamine, or by other procedures known to form an amide bond between an aromatic acid and an amine.

The compounds where X=—CH$_2$O—, —CH$_2$S—, and —CH$_2$NH$_2$— can be made as shown in pathway b. The ester (149) is reduced with a reducing agent such as lithium aluminum hydride in an inert solvent to form the alcohol (150) which can then be reacted with tosyl chloride in pyridine to form tosylate (151), which is in turn reacted in the presence of base with a corresponding phenol (152) thiophenol (153), or aniline (146; where R$^{23}$=H) to form compounds (154), (155) or (156). Again this may require that R$^{13}$ be protected with a suitable protecting group, however modifications necessary because of specific functional groups are understood to be incorporated by one skilled in the art of organic synthesis.

Alternatively, the alcohol (150) can be converted to the corresponding halide with SOCl$_2$, (COCl)$_2$, etc, and the resulting halide can then be reacted with a phenol, thiophenol or aniline in the presence of base to form the desired compound, where X is —CH$_2$O—, —CH$_2$S—, —CH$_2$NH— respectively.

Scheme 23

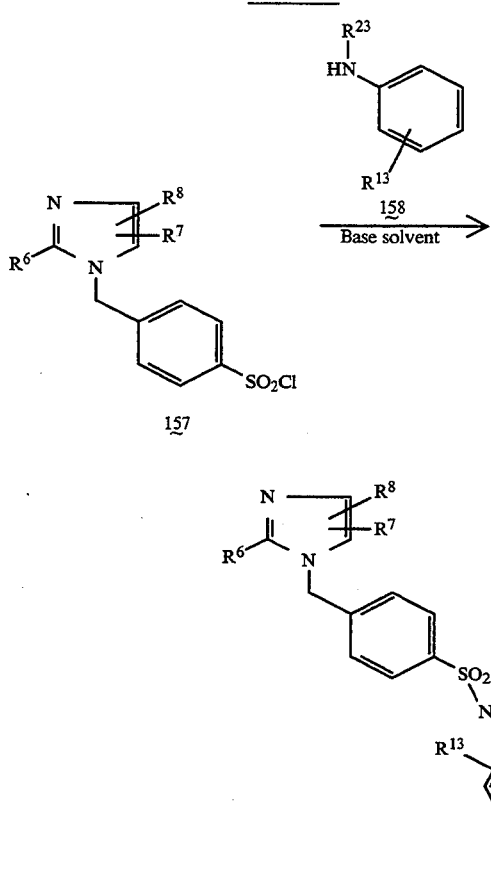

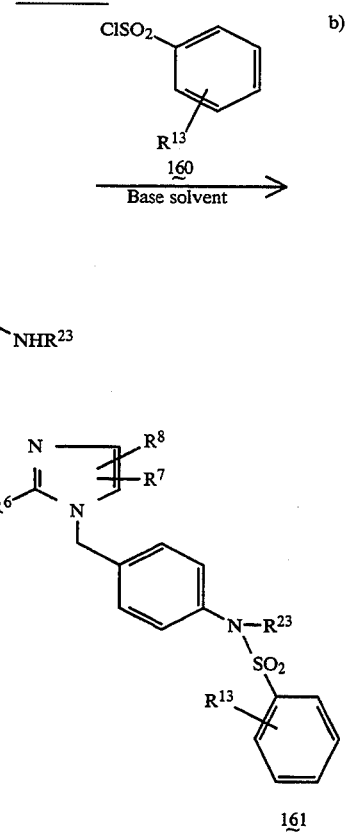

Compounds of Formula (I) where X=—SO$_2$NR$^{23}$— and —NR$^{23}$SO$_2$— may be prepared as shown in Scheme 23. As shown in equation a, sulfonylchloride derivative (157) can be reacted with aniline derivative (158) in a solvent in the presence of an acid scavenger such as sodium bicarbonate, triethylamine or pyridine or under Schotten-Baumann like conditions to give (159). Sulfonylchloride derivative (157) can be obtained by sulfonation of the corresponding benzyl derivative as described earlier, followed by reaction with PCl$_5$ or POCl$_3$. Likewise, aniline (74) may be reacted in the same manner as described above with sulfonylchloride derivative (160) to give (161).

Scheme 24 shows the preparation of furan analogs of the biphenyl compounds (80). Thus, α-ketoester (162), W. Wierenga and H. I. Skulnick, J. Org. Chem., 44, 310 (1979), or the corresponding nitrile (E=CN) can be easily alkylated via standard procedures already mentioned by an alkyl bromide derivative to give (163). The alkene moiety of (163) can be subsequently cleaved by oxidation, for example, with osmium tetroxide, Fieser and Fieser V.1 p. 812 (Lemieux-Johnson oxidation) to yield dicarbonyl-containing compound (164). Cyclization in mineral acids, acidic ion-exchange resin, POCl$_3$/pyridine, or trifluoroacetic anhydride with a catalytic amount of trifluoroacetic acid yields furan (165; Z=O). Reaction of (164) with P$_4$S$_{10}$, for example, will yield the corresponding thiophene (165; Z=S). Reaction of (164) with an amine in refluxing benzene, with azeotropic removal of water or by using molecular sieves to absorb the water will yield the corresponding pyrrole (65; Z=NR$^{11}$). Compounds (166) may be prepared from (165) by standard procedures already described.

Scheme 24

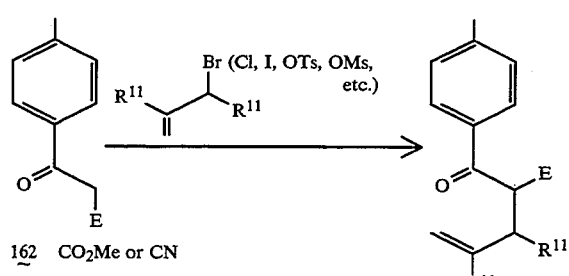

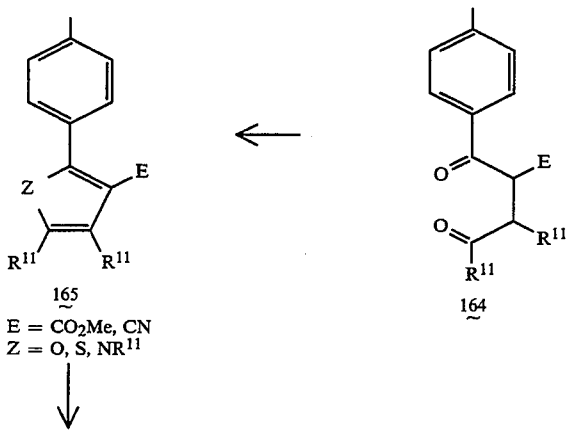

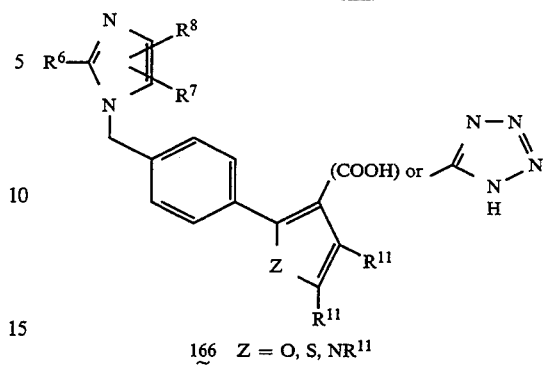

Compounds wherein a methylene group is inserted between the terminal aromatic ring and the acidic functionality may be prepared as shown in Scheme 25, equation a). Thus reduction of ester (167) with, for example, lithium aluminum hydride, gives alcohol (168). Conversion of (168) to the chloride (169) via thionyl chloride followed by reaction with cyanide anion as previously described yields nitrile (170). Compound (170) may be hydrolyzed to carboxylic acid (171) by methods already described or reacted with a hydrazoic acid equivalent to produce tetrazole (172).

Compounds wherein $R^{13}$ is a trifluoromethylsulfonyl hydrazide acidic functional group were prepared by the procedure described in equation b). That is, conversion of ester (167) to the hydrazide (173) by standard hydrazinolysis followed by reaction with triflic anhydride affords hydrazides (174).

Scheme 25

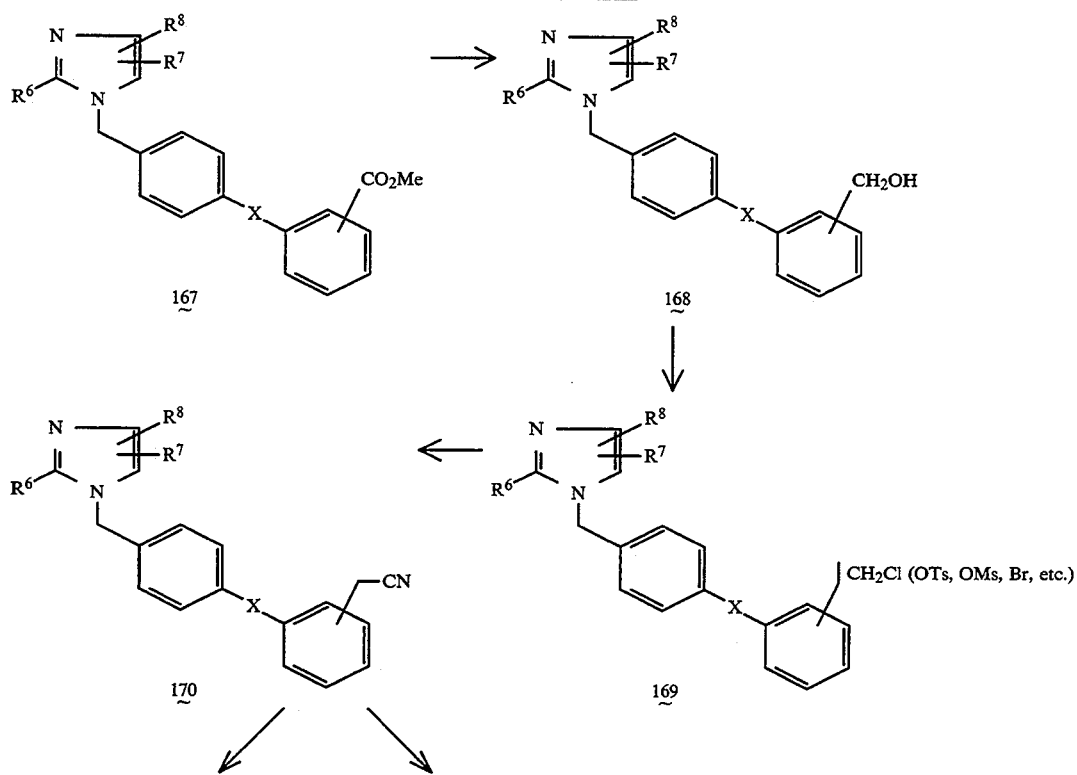

a)

Scheme 25 -continued

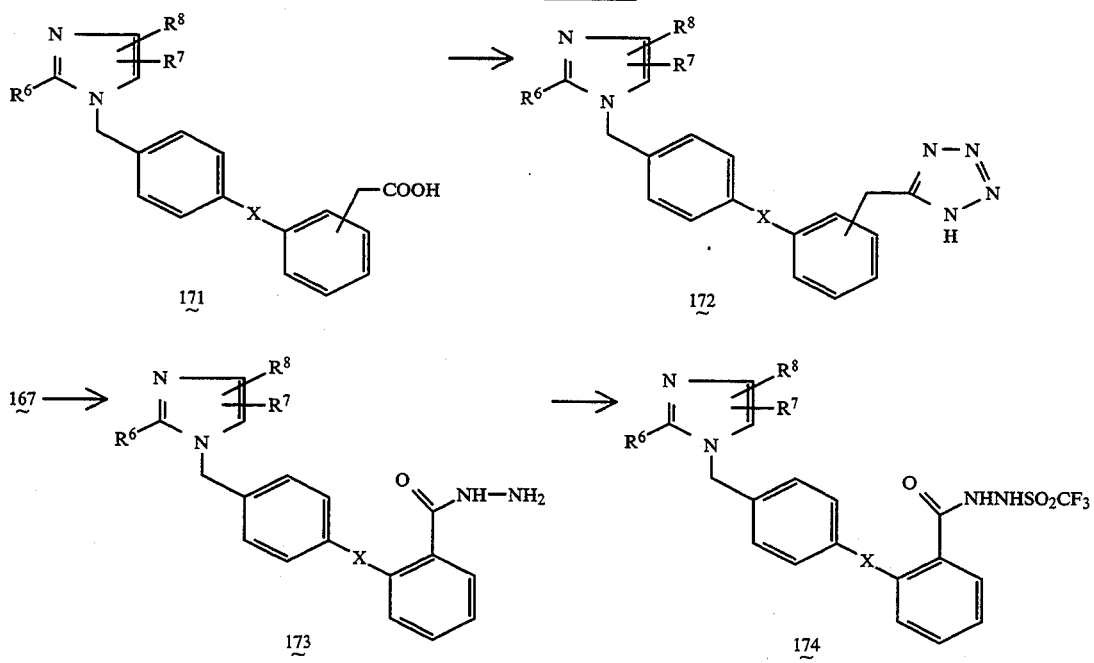

The syntheses of compounds wherein $R^{13}$ is substituted and unsubstituted 1,2,3-triazoles are described in Scheme 26. Thus reduction of ester (175) with a reducing agent such as lithium aluminum hydride or diisobutylaluminum hydride gives alcohol (176). Oxidation with $MnO_2$ or pyridinium chlorochromate converts (176) into aldehyde (177). Nitroethylene derivative (178) is prepared by condensation of aldehyde (177) with nitromethane in the presence of a catalyst, R. M. Letcher and M. P. Sammes, J. Chem. Ed., 62, 262 (1985). Reaction of (178) with sodium azide produces the 1,2,3-triazole (179), (N. S. Zefirov. et al., J. Chem. Soc. Chem. Comm., 1001 (1971)) which may be transformed via procedures already described into product (180).

Aldehyde (177) can also be converted into substituted 1,2,3-triazoles (183) via the sulfone (181), G. Beck. D. Gunther Chem. Ber., 106, 2758 (1973), followed by reaction with sodium azide to give the 1,2,3-triazole (182). Subsequent standard manipulations lead to 1,2,3-triazoles (183) where E=CN and $CO_2R^{11}$. The nitrotriazole (183; E=$NO_2$) may be synthesized from the unprotected triazole (179; P=H) via nitration, R. Huttel. et al., Chem. Ber., 88, 1586 (1955), C. L. Habraken and P. Cohen-Fernandes J. Chem. Soc., 37 (1972), or from bromonitroethylene derivative (184), G. Kh. Khisamutdinov. et al., Zh. Org. Khim., 11, 2445 (1975), by reaction with sodium azide.

A variety of protecting groups may be used in the manipulation of the above triazoles, amongst which is the trityl group. This group may be easily attached by reaction of the triazole with triphenylmethyl bromide or chloride in an inert solvent such as methylene chloride in the presence of an acid scavenger such as triethyl amine. The trityl group may be later removed by stirring or refluxing in an acidic medium such as trifluoroacetic acid/water, HCl in methylene chloride, or acetic acid/water. The trityl group may also be hydrogenolyzed using a noble metal catalyst such as palladium and hydrogen.

Scheme 26

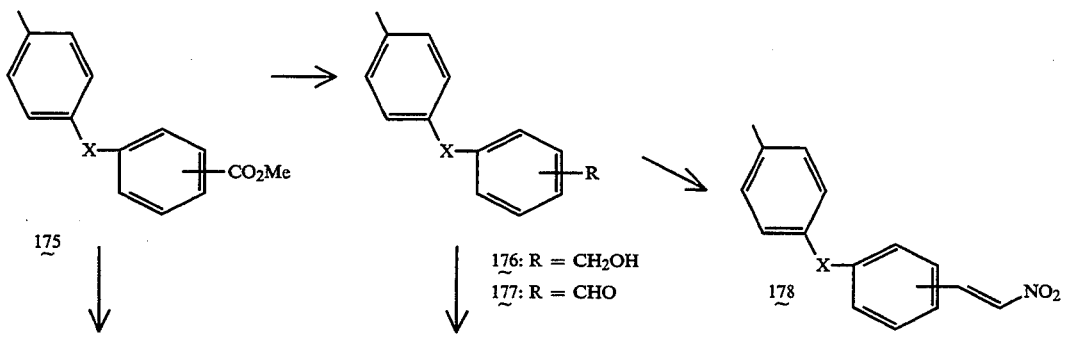

-continued
Scheme 26

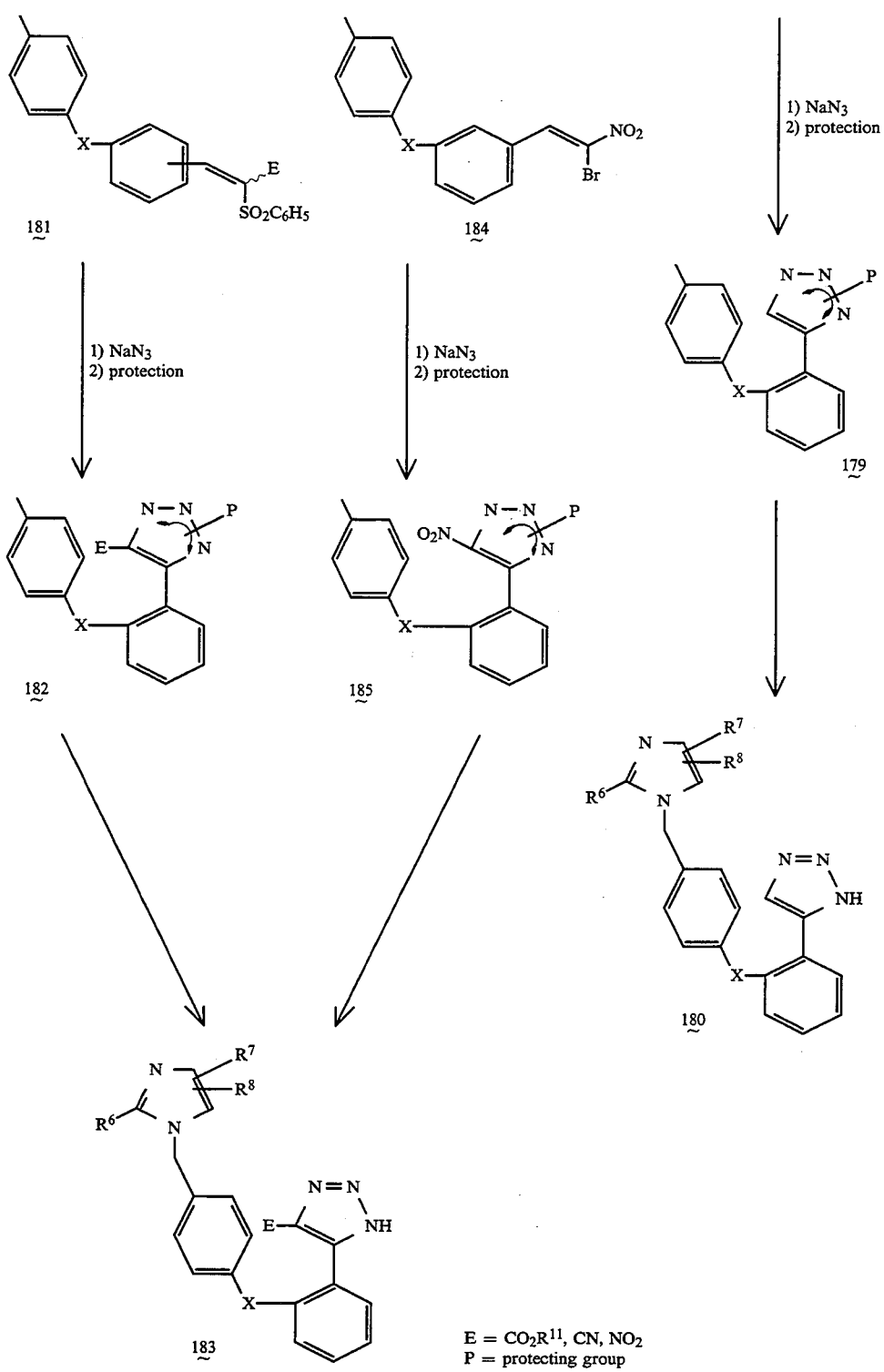

E = CO$_2$R$^{11}$, CN, NO$_2$
P = protecting group

The synthesis of trtifluoromethyl-1,2,4-triazoles (190) is depicted in Scheme 27. Acid chloride (186) is converted to amide (187) using standard procedures familiar to one skilled in the art. A preferred protecting group is the 2-propionitrile group (P=CH$_2$CH$_2$CN). Thus (187; P=CH$_2$CH$_2$CN) can be synthesized from (186) and β-aminopropionitrile under Schotten-Baumann like conditions, using aqueous base in an organic solvent to help solubilize (186) and (187). Amide (187) is converted to amidrazone (188) by reaction with PCl$_5$ or phosgene to make an iminoyl chloride which then in turn is reacted with excess hydrazine. Amidrazone (188) is cyclized to the trifluoromethyl-1,2,4-triazole (189) with trifluoroacetic anhydride and then converted to 190 via bromination, alkylation and deprotection as previously described.

Scheme 27

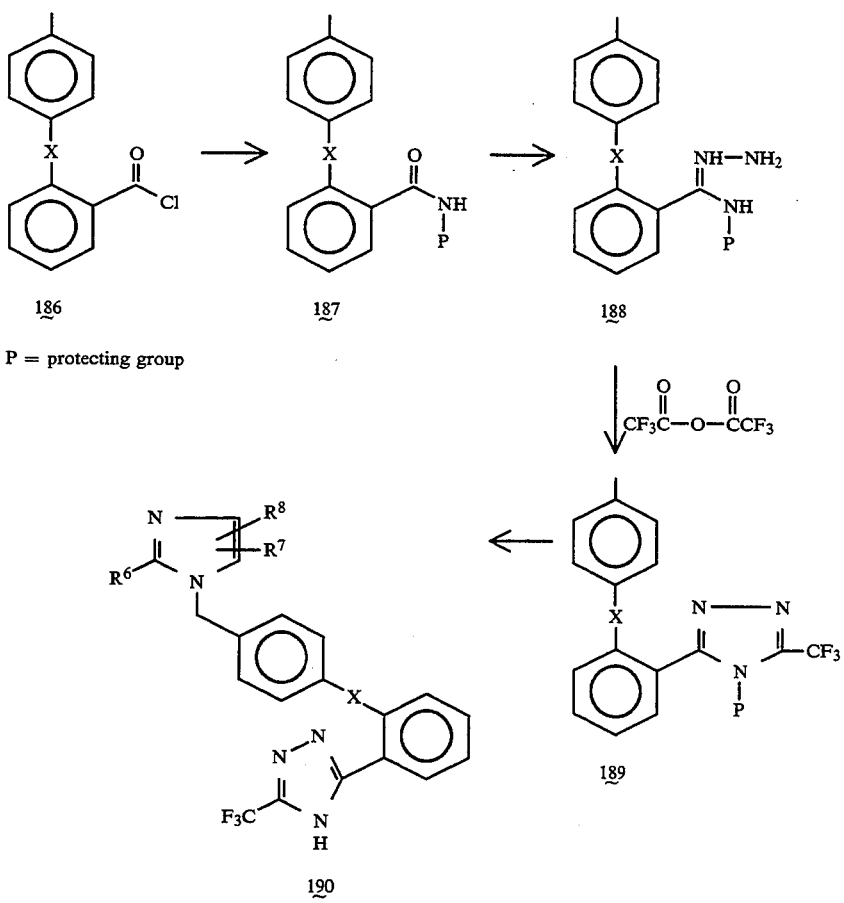

P = protecting group

Pertinent R⁶ groups may be variously introduced by many procedures including those described in Scheme 28 which describes imidazole construction.

The R⁶ groups so introduced may stand unchanged or may be further elaborated if appropriately functionalized, according to methods familiar to those skilled in the art such as are illustrated in Scheme 28.

Scheme 28

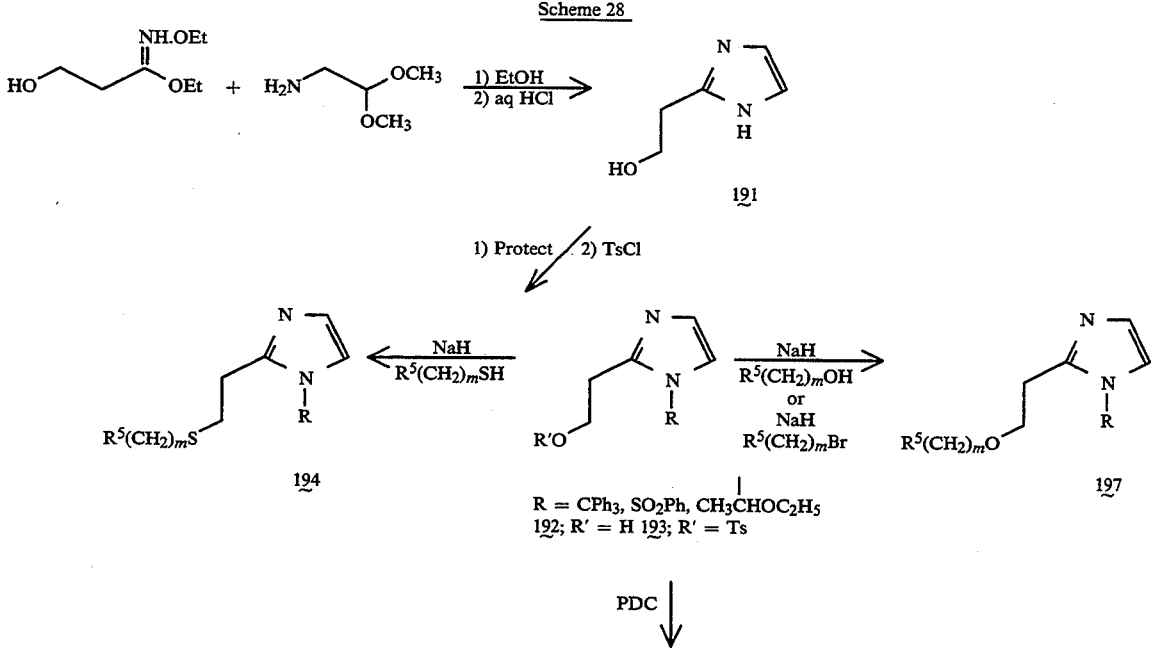

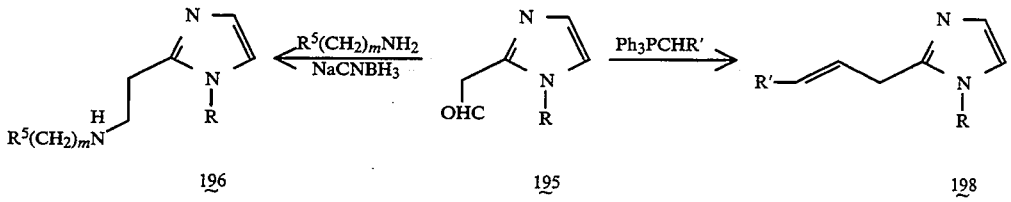

The 2-alkenylimidazoles (201) can be prepared by bromination of the 2-alkylimidazoles (199) followed by and sodium periodate to afford aldeldydes (202) followed by Wittig reaction.

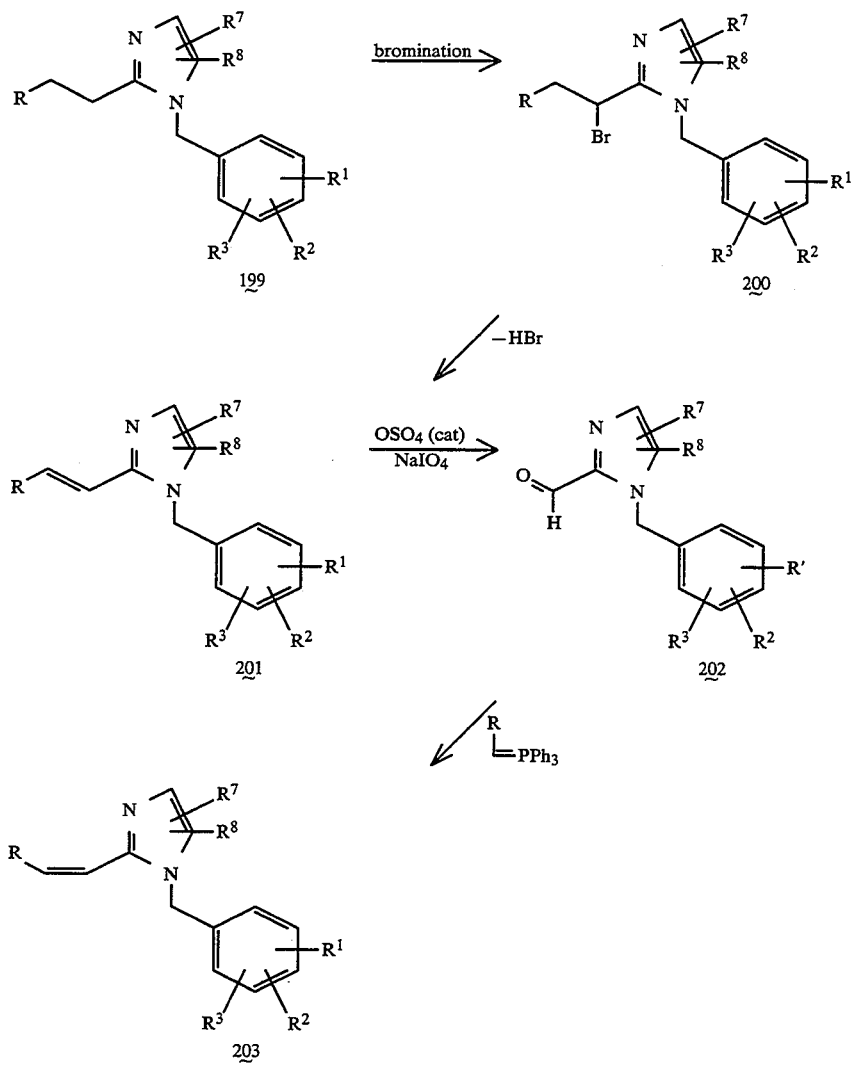

R = aklyl, cycloalkyl elimination of hydrogen bromide. The bromination is preferably accomplished by UV-irradiation for 1–4 hours of imidazole (199) and N-bromosuccinimide, in an inert solvent, such as carbon tetrachloride at 25° C. Treatment of the intermediate bromide (200) with a base, such as DBU, triethylamine, or potassium t-butoxide, affords the trans 2-alkenylimidazoles (201). Cis alkenyl derivatives (203) are prepared from the trans alkenyl compounds by treatment with osmium tetroxide Alternatively, $R^6$ groups may be introduced by metallation of a protected imidazole or protected 2-methylimidazole followed by addition of an appropriate electrophile as illustrated in Scheme 30, equations a) and b). The products (alcohols, esters, halides, aldehydes, alkyls) are suitable for further elaboration by methods familiar to those skilled in the art. Metallation of imidazoles is described in K. L. Kirk, *J. Org. Chem.*, 43, 4381 (1978); R. J. Sundberg, *J. Het. Chem.*, 14, 517

(1977); J. V. Hay et al., *J. Org. Chem.*, 38, 4379 (1973); B. Iddon, *Heterocycles*, 23, 417 (1985).

Condensation of 2-methylimidazole and appropriate electrophiles (equation b) with catalytic acid or base as described in A. R. Katritzky (Ed.), "Comprehensive Heterocyclic Chemistry", Vol. 5, p. 431, Pergamon Press, N.Y., 1984 affords products wherein $R_6$ is alkenyl which are suitable for further elaboration.

Scheme 30

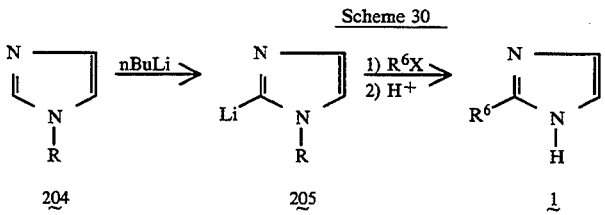

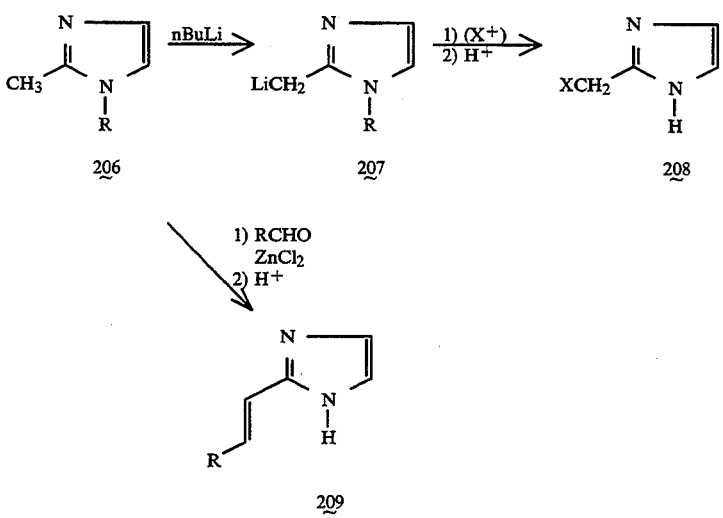

Various 2-substituted imidazoles can be prepared by reaction of a protected 2-trimethylsilylimidazole with a suitable electrophile by the method described by F. H. Pinkerton and S. F. Thames, *J. Het. Chem.*, 9, 67 (1972), which can be further elaborated as desired. Alternatively, $R^6$ may also be introduced by nickel catalyzed cross-coupling of Grignard reagents with 2-(methylthio)imidazoles (Scheme 31) as described by E. Wenkert and T. W. Ferreira, *J. Chem. Soc., Chem. Commun.*, 840, (1982); E. Wenkert et al., *J. Chem. Soc., Chem. Commun.*, 637, (1979); and H. Sugimura and H. Takei, *Bull. Chem. Soc. Japan*, 58, 664 (1985). The 2-(methylthio)imidazoles can be produced by the procedure described in German Patent No 2,618,370 and the references cited therein.

Scheme 31

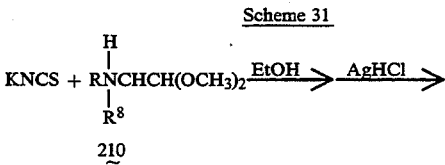

-continued
Scheme 31

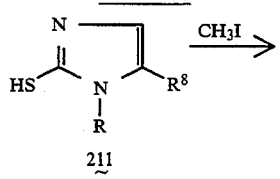

a)

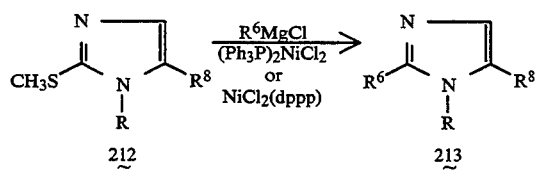

As shown in Schemes 32-36, elaboration of $R^8$ can be accomplished by some of the procedures described in Schemes 3 and 28, by chain extension reactions familiar to those skilled in the art, or by degradation reactions such as conversion of an ester to an acid or an alkene to an aldehyde.

Specifically, the hydroxymethyl group can be activated for the displacement reaction by reacting with thionyl chloride, $PCl_5$ or with carbon tetrachloride/triphenylphosphine to form a corresponding chloro derivative. By a similar reaction bromo and iodo derivatives can be obtained. The hydroxymethyl group can also be activated by forming the corresponding p-toluenesulfonate, methanesulfonate and trifluoromethane sulfonate derivatives.

Scheme 32

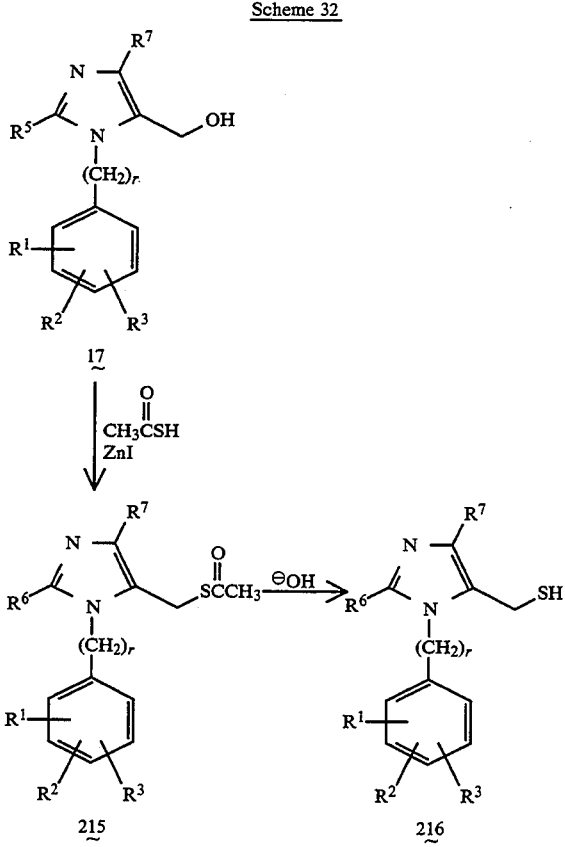

As shown in Scheme 32, the hydroxyl group can be converted to thiolacetic acid derivative (215), J. Y. Gauthier, Tet. Lett., 15 (1986), and to thiol derivative (216) by subsequent hydrolysis.

The hydroxymethyl group on compound (17) can be readily oxidized to an aldehyde group by means of manganese dioxide or ceric ammonium nitrate. The aldehyde group will undergo chain extension reactions such as the Wittig and Wittig-Horner reactions and enter into typical carbon-carbon bond forming reactions with Grignard and lithium reagents as well as with compounds bearing activated methylene groups. Alternatively, the hydroxymethyl group can be oxidized directly to an acid functionality which can in turn be converted to ester and amide derivatives. The esters and amides can be prepared directly from the aldehydes by manganese dioxide oxidation in the presence of sodium cyanide and an alcohol or amine, J. Am. Chem, Sec., 90, 5616 (1968) and J. Chem. Soc. (C), 2355 (1971).

As shown in Scheme 33, the chlorine on compound (25) can be displaced by the anion of dialkyl malonate to give the corresponding malonate derivative (217). The saponification of (217) with NaOH (or KOH) gives the corresponding diacid which can be decarboxylated to give the corresponding propionic acid derivative (218) by heating to 120° C. Alternatively, (218) can be directly obtained by refluxing (217) with a mineral acid such as HCl or sulfuric acid. The free acid (218) can be esterified by heating in a medium of the various alcohols and a catalytic amount of mineral acids such as HCl or sulfuric acid to give the corresponding esters (219). Alternatively the esters can be obtained by reacting the free acid (218) and the corresponding alcohols in the presence of coupling reagents such as DDQ or EEDQ. A similar reaction with various mono-substituted and disubstituted amines produces the corresponding amides (220). A similar reaction with various mercaptans produces the corresponding thioesters.

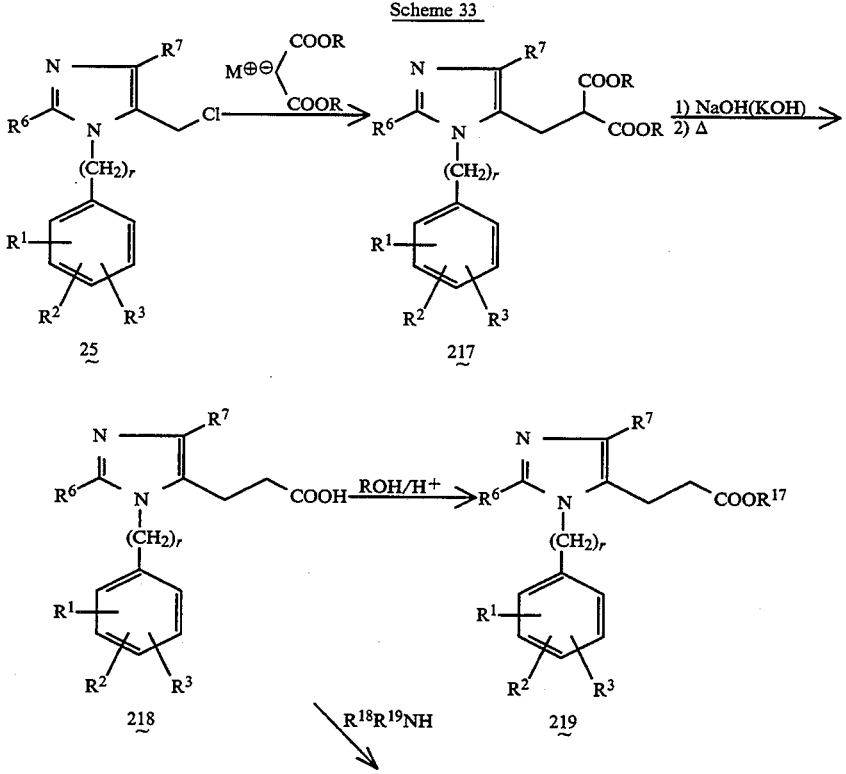

Scheme 33

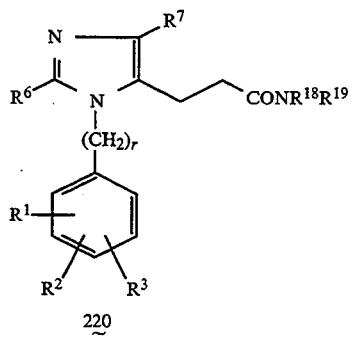

220

As shown in Scheme 34, the chloro group on (25) can be displaced by the sodium salt or potassium salt of the alkyl, aryl or arylalkyl mercaptans to give the corresponding sulfide derivatives (221). The amine derivative (222) can be obtained by treating (25) with ammonia or with the corresponding mono-substituted amines. Alternatively, the chloro group may be displaced by sodium azide to give an azide intermediate which upon reduction with $H_2$ over a noble metal catalyst or with a reducing agent such as chromous chloride (W. K. Warburton, *J. Chem. Soc.*, 2651 (1961)) yields (222) where $R^{10}$ and $R^{11}$ are hydrogen. This amine can be subsequently alkylated with alkyl halides, or reductively alkylated with aldehydes and ketones to give alkyl derivatives of (222). The amines (222) are converted to the corresponding carbamates (224), sulfonamides (225), amides (226) or ureas (227) by standard procedures illustrated in Scheme 34 and familiar to one skilled in the art.

Scheme 34

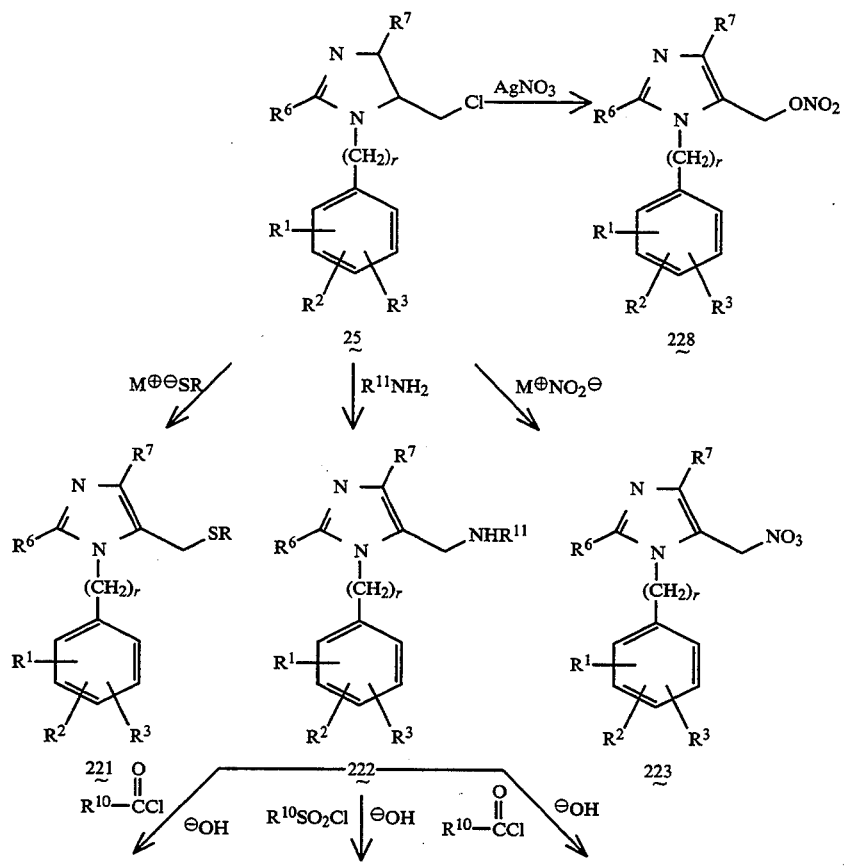

-continued
Scheme 34

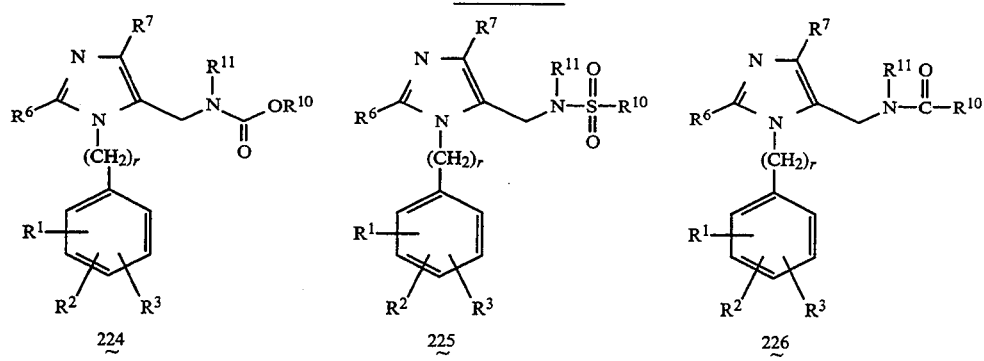

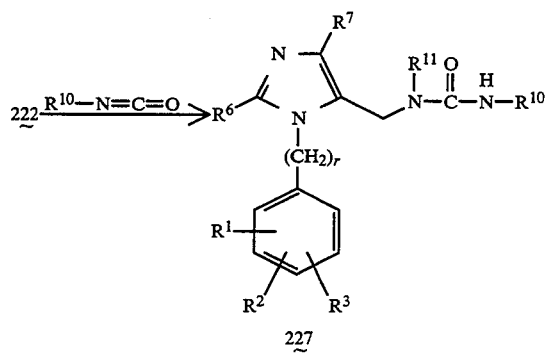

The reaction between the tiopyridyl ester (229) and a suitable Grignard reagent produces the ketones (230).

Scheme 35

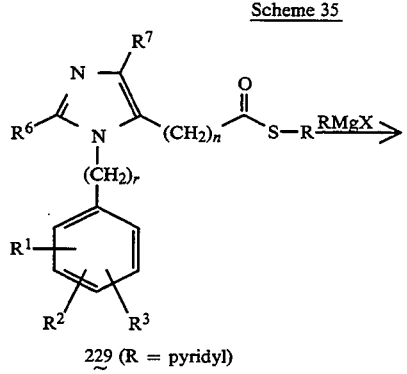

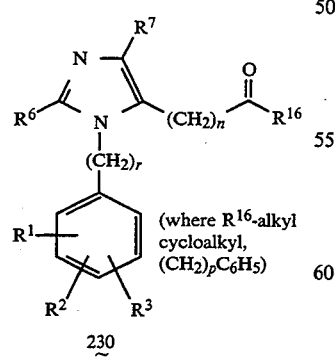

As shown in Scheme 36 when the imidazole 4- and-/or 5-position contains an aldehyde (231) then reaction with organometallic reagents such as Grignard or alkyl-/aryllithium reagents will yield alcohols (232) which in turn may be transformed into a variety of other functionality familiar to one skilled in the art.

Scheme 36

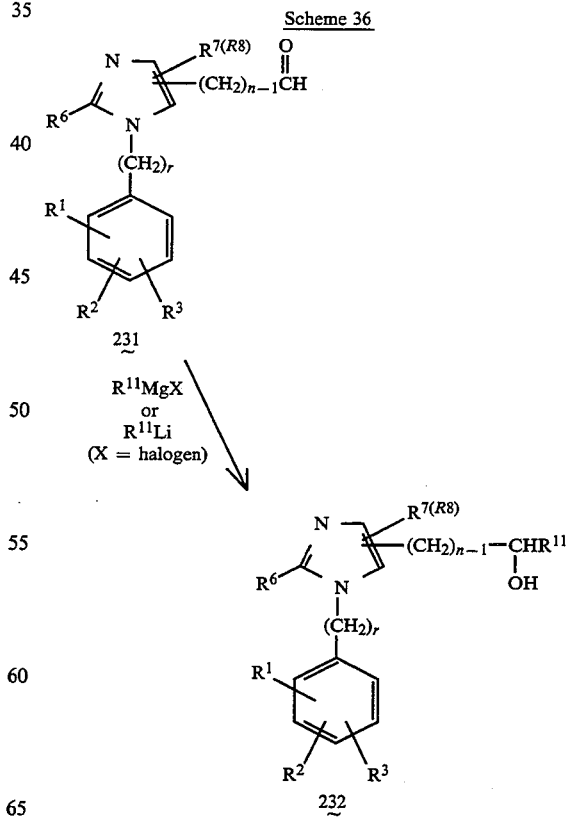

As shown in Scheme 37, ester 234 may be obtained by direct oxidation of aldehyde 233 with NaCN, MnO$_2$ in methanol (Corey, E. J., et al. *J. Am. Chem. Soc.* (1968) 90, 5616). Oxidation of 233 with NaCN, MnO$_2$, and an amine in 2-propanol leads to the corresponding amide 235 (Gilman, N. W. *Chem. Comm.* (1971) 733).

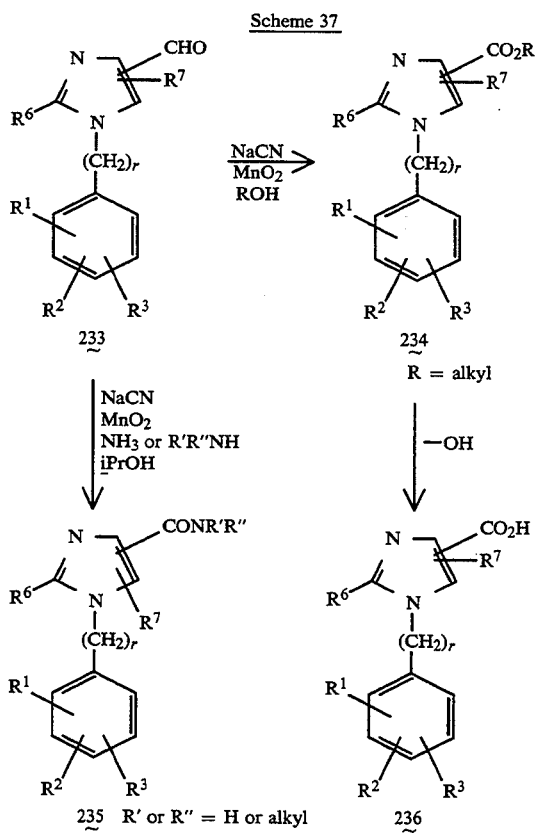

Saponification of ester 234 will lead to carboxylic acid 236.

Aldehyde 233, in turn, may be made from the corresponding alcohol 17 by a variety of methods familiar to one skilled in the art, including pyridium chlorochromate (PCC), Swern and ceric ammonium nitrate (CAN) oxidations.

Likewise, the unalkylated hydroxymethylimidazole derivative 1(R$^8$=CH$_2$OH) may undergo the transformations to the aldehyde, ester, carboxylic acid and carboxamide by the reactions mentioned above for the alkylated case.

Compounds 238 (where Ar=p-biphenylyl, p-phenoxyphenyl, or a heteroaryl group as described in the scope under the definition of R$^7$) can be prepared by the coupling of an arylmetal derivative (ArM, where M=ZnBr, Me$_3$Sn, B(OH)$_2$, etc.) with a haloimidazole 237 in the presence of a transition metal catalyst such as palladium, nickel, platinum, zirconium, etc. (Scheme 38a). Alternatively an imidazole metal derivative 239 can be coupled to an arylhalide to prepare 238 (Scheme 38b).

The arylmethyl derivatives 240 can be prepared employing the transition metal catalysed coupling of 237 and an arylmethylmetal (ArCH$_2$M', where M'=ZnBr, etc.), as shown in Scheme 38c.

Compounds 241 may be prepared, as described in Scheme 38d, by the coupling of an alkenyl- or alkylnyl-metal derivative (AM) or the corresponding alkene or alkyne (AH) with 237.

Likewise, the unalkylated imidazoles (1, where R$^7$=Br or I) may undergo the coupling reactions described in Scheme 38a–d [For references to transition metal catalysed coupling reactions, see: Richard C. Heck, Palladium Reagents in Organic Synthesis, Academic Press, New York, Chapters 6, 7, and 8; and references cited therein.]

The compounds of formula I where R$^7$ is an alkynyl group, a substituted alkynyl group, or a substituted alkenyl group and the carbon-carbon double or triple bond is not adjacent to the imidazole ring (e.g., R$^7$=(CH$_2$)$_4$CH=CH(CH$_2$)$_v$Ar, where v≠0) can be prepared by a variety of chain elongation methods and chain coupling reactions known to one skilled in the art including those described in Schemes 3, 28, 29, 33, 35, 36, and 38.

The compounds of formula I where R$^7$ is a substituted alkyl group (R$^7$=(CH$_2$)$_w$Ar, where w=2–10) can be prepared by reduction of the corresponding alkenes (241) by catalytic hydrogenation.

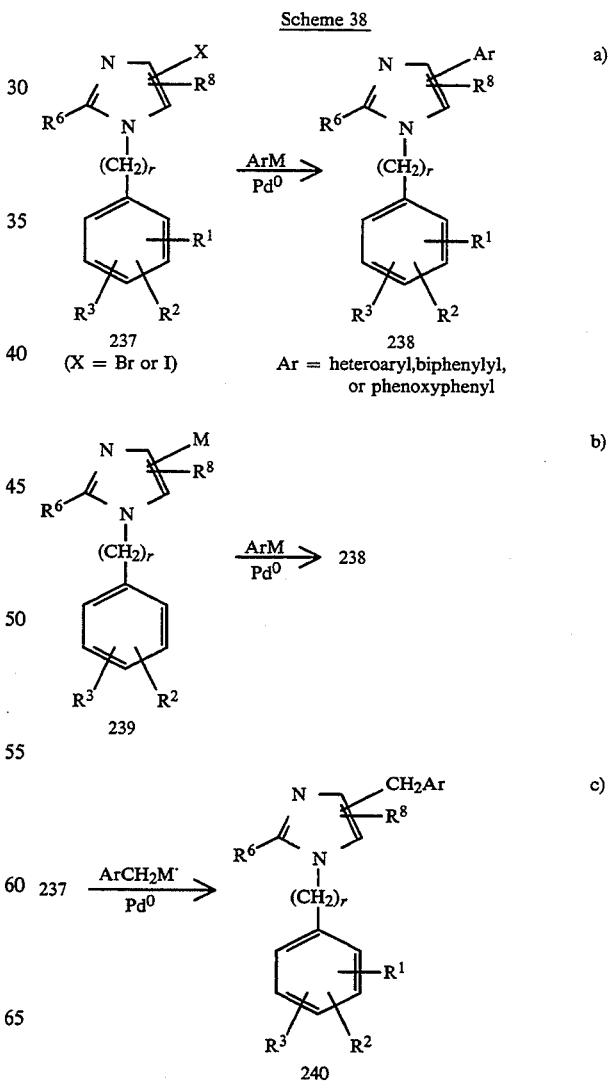

-continued
Scheme 38

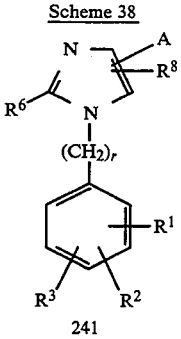

A = VINYL
CH=CH(CH₂)ₓAr
C≡C(CH₂)ᵧCH₃
C≡C(CH₂)ₓPh·
C≡C(CH₂)ₓAr

Ph = phenyl or
substituted phenyl
x = 0-8
y = 0-7
z = 0-4

Compounds of formula I where $R^7$=vinyl or arylalkenyl and $R^8$=CH₂OH, aldehyde, or COOH can be prepared as shown in Scheme 39.

2-Alkylimidazole-4,5-dicarboxylic acids (242), prepared by the method of R. G. Fargher and F. L. Pyman (J. Chem. Soc., (1919) 115, 217), can be converted into their corresponding diesters (243) by simply refluxing in an alcohol solvent in the presence of an acid such as HCl, or by many other methods familiar to one skilled in the art.

d) Diester (243) can then be converted into its metallic salt by reaction with sodium methoxide, sodium ethoxide, sodium hydride, potassium hydride or any other base in an appropriate solvent such as DMF. The resultant salt is then alkylated with the appropriately substituted benzyl derivative (2) to yield benzylimidazole (244). The above alkylation sequence may be also performed by heating or refluxing the benzyl halide (tosylate or mesylate) (2) with imidazole (243) in a solvent such as DMF in the presence of an acid scavenger such as potassium or sodium carbonate.

Diester (244) can be reduced with lithium aluminum hydride in an inert solvent such as THF to the corresponding dialcohol (245). Selective oxidation of dialcohol (245) with manganese dioxide in an inert solvent such as THF yields primarily aldehyde (247) with a minor product dialdehyde (246). Separation of (247) from (246) either by crystallization or chromatographically, followed by Wittig reaction of (247) with methylenetriphenylphosphorane or the appropriately substituted arylalkylidenetriphenylphosphorane in an inert solvent such as THF yields the 4-alkenyl-5-hydroxymethylimidazole (248). Further oxidation of (248) with the Dess-Martin periodinane (J. Org. Chem., (1983) 48, 4155), with manganese dioxide, with pyridinium chlorochromate, with barium manganate or with other oxidants familiar to one skilled in the art, in an inert solvent such as THF or methylene chloride followed by deprotection of either $R^1$, $R^2$, or $R^3$ if necessary yields the 4-alkenylimidazole-5-carboxaldehyde (249).

Oxidation of (249) with, for example, manganese dioxide/cyanide ion (Corey, E. J., et al. J. Am. Chem. Soc., (1968) 90, 5616) or with potassium permanganate (Sam, D. J. et al. J. Am. Chem, Soc., (1972) 94, 4024) yields 4-alkenylimidazole-5-carboxylic acid (250).

Scheme 39

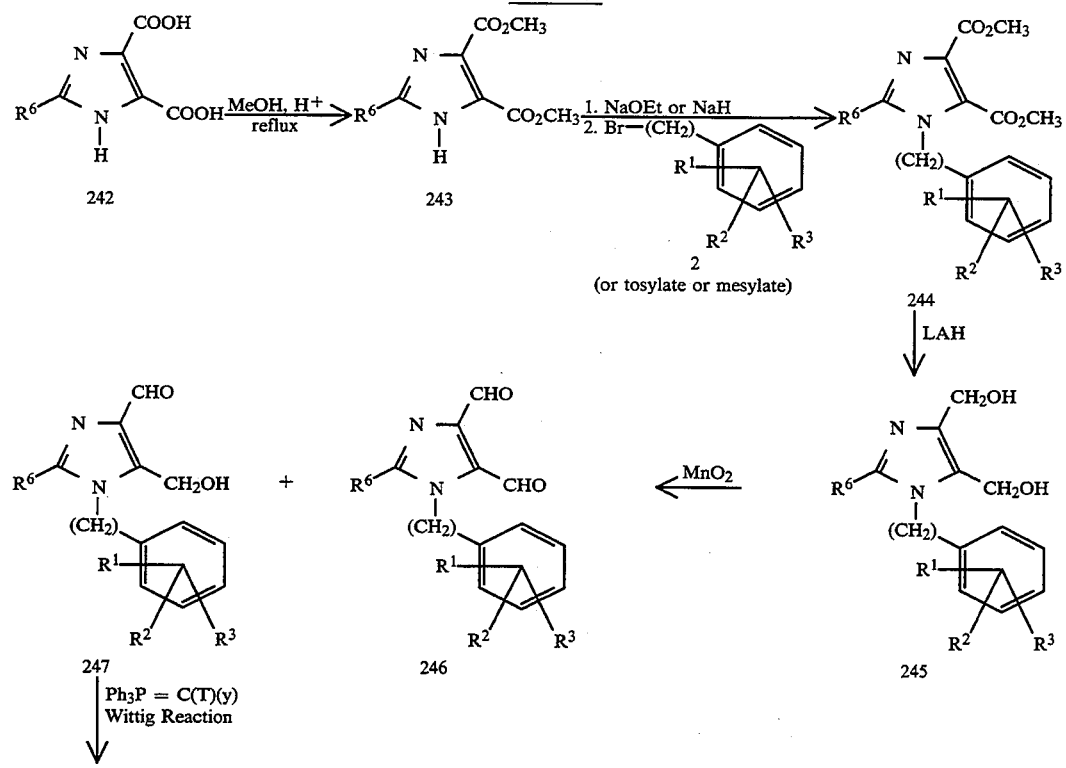

-continued
Scheme 39

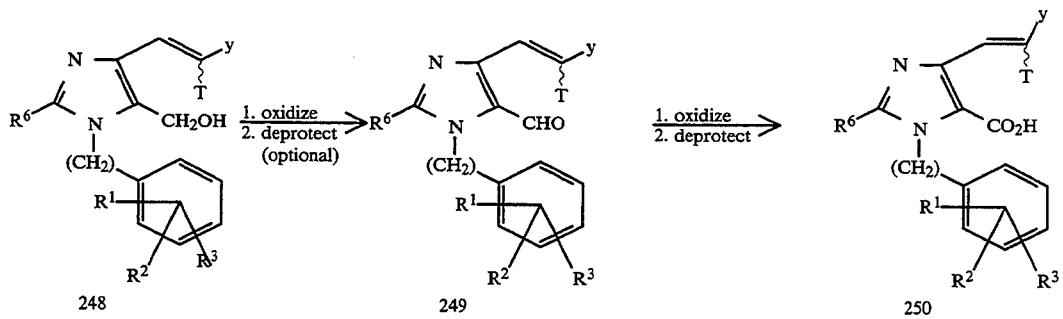

where T=H, y=H, (CH₂)ₓ-Aryl or T and y taken together form a cyclic ring of 3-8 carbons and the regiochemistry about the double bond in 248, 249 and 250 can be Z or E.

Imidazoles represented by structure (251) where X is Cl, Br, or I and E is an electron withdrawing group such as an ester, ketone, nitro, alkylsulfonyl, arylsulfonyl, etc., can undergo the nucleophilic aromatic substitution reaction (H. Schubert, H. Simon, A. Jumar, Z. Chem. (1968) 62–63) where the leaving group X is substituted by a nucleophile such as sulfur, carbon, or nitrogen to yield adducts (252) (Scheme 40). The reaction can be done in hydroxylic solvent such as methanol or non-hydroxylic solvent such as DMSO at room temperature to the reflux temperature of the solvent. The nucleophile sometimes must be converted into its anion to make it more nucleophilic. For example, thiophenol can be refluxed in methanol in the presence of sodium methoxide and the haloimidazole (251). Other nucleophiles include other alkyl and arylthiols, heteroarylthiols, thiolacetic acid, alkyl and arylsulfonamides, heteroarylsulfonamides, diacylamines, alkyl and arylamines, heteroarylamines, etc., familiar to one skilled in the art.

If a sulfur nucleophile is used, the resultant sulfides can be oxidized to the corresponding sulfoxides and sulfones by methods familiar to one skilled in the art.

Scheme 40

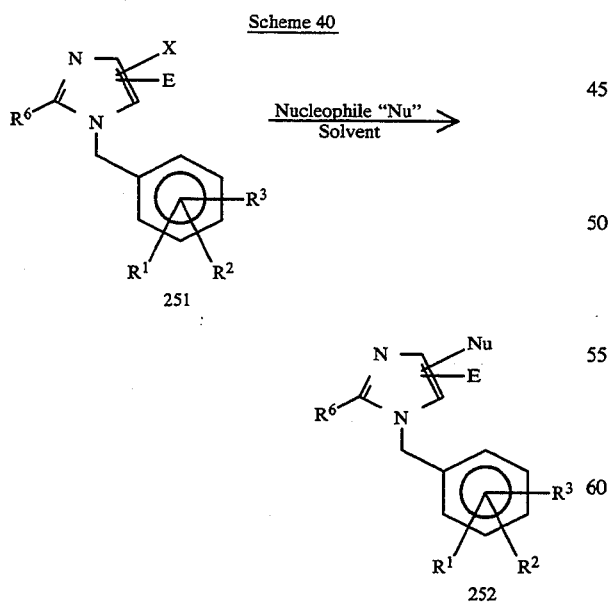

The compounds of this invention and their preparation can be understood further by the following examples, which do not constitute a limitation of the invention. In these examples, unless otherwise indicated, all temperatures are in degrees centigrade and parts and percentages are by weight.

EXAMPLE 1

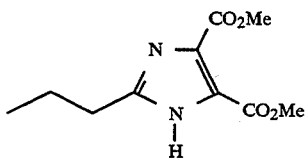

PART A: Preparation of
2-n-Propyl-4,5-dicarbomethoxyimidazole 2-n-Propylimidazole-4,5-dicarboxylic acid [prepared by the method of R. G. Fargher and F. L. Pyman (J. Chem. Soc., (1919) 115, 217), mp 257 (dec.) °C.] (17.14 g, 86.6 mmol, 1 eq), methanol (400 mL) and acetyl chloride (38.1 mL, 534 mmol, 6 eq) were cautiously mixed (acetyl chloride addition to methanol is very exothermic) and refluxed overnight. The solvent was removed in vacuo and water (100 mL) and 10N NaOH were added until pH=7. The aqueous mixture was extracted with ethyl acetate (3×), the organic layers combined, dried (MgSO₄) and the solvent removed in vacuo to yield 12.00 g of a white solid. Recrystallization from hexane/ethyl acetate yielded 11.41 g of a white solid (58%); mp: 162.0°–164.5° C. NMR (CDCl₃) δ 3.95 (s,6H); 2.78 (t,2H); 1.83 (t of t, 2H,J=7,7Hz); 0.97 (t3H,J=7Hz); IR (neat) 1735 cm−¹. Anal. calcd. for $C_{10}H_{14}N_2O_4 \cdot (H_2O)_{0.25}$: C, 52.06; H, 6.28; N, 12.14. Found: C, 52.06; H, 6.17; N, 12.49.

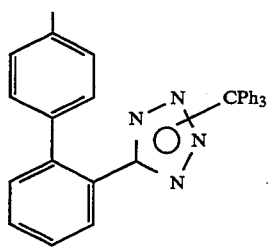

Part B: Preparation of 4-Methyl-2'-(N-triphenylmethyl-(1H-tetrazol-5-yl))biphenyl 4'-Methylbiphenyl-2-nitrile (preparation described in European patent application 0253310, published on 20.01.88) (10.00 g, 51.7 mmol, 1 eq), tri-n-butyltin chloride (14.0 mL, 51.7 mmol, 1 eq), sodium azide (3.4 g, 51.7 mmol, 1 eq), and xylene (50 mL) were mixed and refluxed for 64 h after which the reaction mixture was cooled to room temperature. 10.0N NaOH (6.10 mL, 0.061 mmol, 1.2 eq) and trityl chloride (14.99 g, 53.8 mmol, 1.04 eq) were then added and the mixture stirred for 24 h after which water (39 mL) and heptane (100 mL) were added. The resultant slurry was stirred at 0° C. for 1.5 h. The resultant solids thus obtained were filtered, washed with water (2×55 mL) washed once with 3:2 heptane/toluene (55 mL) and dried overnight under high vacuum to yield 19.97 g of a light yellow powder: mp 148.0°–155.0° C. (dec.). These solids were slurried in ethyl acetate (75 mL) and filtered to yield 15.0 g of a light yellow powder: mp 164.0°–165.5° C. (dec.). NMR (CDCl$_3$) δ 7.91 (d,1H,J=9Hz); 7.53–7.18 (m,13H); 7.02–6.84 (m,9H); 2.25 (s,3H).

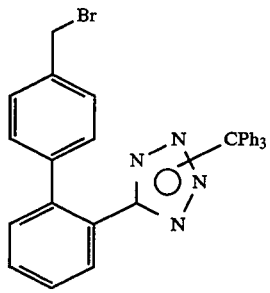

PART C: Preparation of 4-Bromomethyl-2'-(N-triphenylmethy-(1H-tetrazol-5-yl))biphenyl, a representative procedure 4-Methyl-2'-(N-triphenylmethyl-(1H-tetrazol-5-yl))biphenyl (52.07 g, 109 mmol, 1 eq), N-bromosuccinimide (19.4 g, 109 mmol, 1 eq), benzoyl peroxide (1.0 g) and carbon tetrachloride (300 mL) were mixed and refluxed for 2.5 h. The reaction was cooled to room temperature and the succinimide filtered. The filtrate was concentrated and the residue triturated with ether to yield a first crop of 36.0 g: mp 129.5°–133.0° C. (dec.). NMR (CDCl$_3$) δ 4.37 (CH$_2$Br). This material was suitable for further transformation.

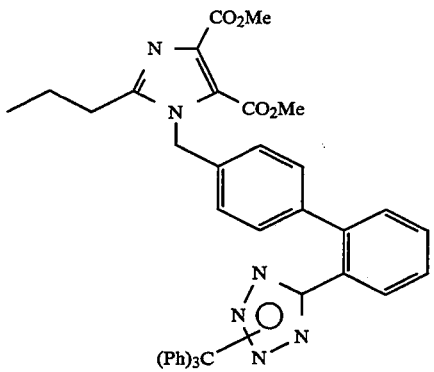

PART D: Preparation of 4,5-dicarbomethoxy-2-n-propyl-1-[(2'-(N-triphenylmethyl-(1H-tetrazol-5-yl))biphenyl-4-yl)methyl]imidazole Sodium hydride (1.06 g, 44.2 mmol, 1 eq) was added to a solution of 4,5-dicarbomethoxy-2-n-propylimidazole (10.00 g, 44.2 mmol, 1 eq) in DMF at room temperature. Foaming and gas evolution occurred. The temperature was increased to 60° C. for 15 minutes to dissolve all of the sodium hydride. Gas evolution ceased and the mixture was cooled to room temperature. To this mixture was added a DMF solution of 4-bromomethyl-2'-(N-triphenylmethyl-(1H-tetrazol-5-yl))biphenyl (24.64 g, 44.2 mmol, 1 eq). After 24 h, the solvent was removed in vacuo, and the residue was flash chromatographed in 75:25 hexane/ethyl acetate to 100% ethyl acetate over silica gel to yield 15.78 g (51%) of a white glass which was suitable for further transformation. Recrystallization from ethanol yielded an analytical sample (white crystals); top: 124.0°–125.5° C. NMR (CDCl$_3$) δ 7.91 (d of d,1H,J=3,9 Hz); 7.59–7.20 (m12H); 7.09 (d,2H,J=9Hz); 6.94 (m, 6H); 6.76 (d,2H,J=9Hz); 5.30 (s,2H); 3.89 (s,3H); 2.50 (t,2H,J=7Hz); 1.67 (t of t, 2H,J=7,7Hz); 0.85 (t,3H,J=7Hz). IR (neat) 1718 cm$^{-1}$. Anal. calcd. for C$_{43}$H$_{38}$N$_6$O$_4$: C, 73.49; H, 5.45; N, 11.96. Found: C, 73.23; H, 5.48; N, 12.22.

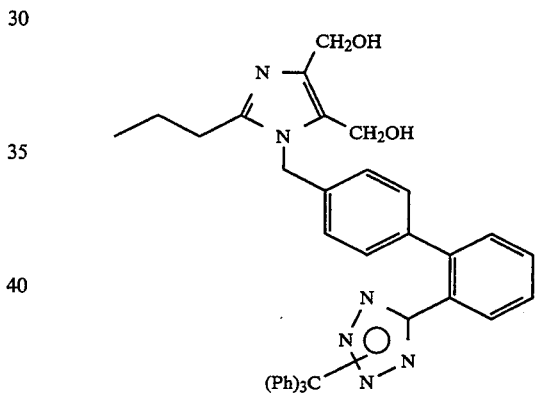

PART E: Preparation of 4,5-dihydroxymethyl-2-n-propyl-1-[(2'-(N-triphenylmethyl-(1H-tetrazol-5-yl))biphenyl-4-yl)methyl]imidazole 4,5-Dicarbomethoxy-2-n-propyl-1-[(2'-(N-triphenylmethyl-(1H-tetrazol-5-yl))biphenyl-4-yl)methyl]imidazole (9.88 g, 14.1 mmol, 1 eq) was dissolved in a minimum of THF and to this solution, lithium aluminum hydride (1.0M in THF) (15.48 mL, 15.48 mmol, 1.1 eq) was slowly added dropwise. The mixture was allowed to stir at room temperature overnight after which It was quenched by the Steinhardt procedure (Fieser & Fieser V.1, p.584) as follows: to the reaction mixture water (0.66 mL) was first carefully added followed by 15% NaOH (0.66 mL) followed by water (1.97 mL). After stirring for 72 h, a very fine suspension of particulate had formed which was slowly filtered through Celite ™. The filtrate was dried (MgSO$_4$) and the solvent removed in vacuo to yield 8.83 g of a yellow glass which could not be recrystallized. This Intermediate was suitable for further transformation. NMR (DMSO-d$_6$) δ 7.82 (d, 1H,J=9Hz); 7.68–7.28 (m,12H);

7.05 (d,2H,J=9Hz); 6.87 (d,6H,J=9Hz); 5.16 (s,2H); 4.94 (t,1H,J=7Hz); 4.66 (t,1H,J=7Hz); 4.37 (d,2H,J=7Hz); 4.32 (d,2H,J=7Hz); 2.34 (t,2H,J=7Hz); 1.52 (t of q,2H,J=7,7Hz); 0.77 (t,3H,J=7Hz). IR (neat) 3300 br; 3061; 1027; 1006; 909; 732; 699 cm$^{-1}$. Anal. calcd. for $C_{41}H_{38}N_6O_2 \cdot H_2O$: C, 74.07; H, 6.06; N, 12.64. Found: C, 74.06; H, 5.95; N, 11.86.

PART F: Preparation of 5-hydroxymethyl-2-n-propyl-1-[(2'-(N-triphenylmethyl-(1H-tetrazol-5-yl))biphenyl-4-yl)methyl]imidazole-4-carboxaldehyde and 2-n-propyl-1-[(2'-(N-triphenylmethyl-(1H-tetrazol-5-yl))biphenyl-4-yl)methyl]imidazole-4,5-dicarboxaldehyde 4,5-Dihydroxymethyl-2-n-propyl-1-[(2'-(N-triphenylmethyl(1H-tetrazol-5-yl))biphenyl-4-yl)methyl]imidazole (8.56 g, 13.2 mmol, 1 eq) was dissolved in a minimum of THF and added to a slurry of manganese dioxide (11.14 g, 128.1 mmol, 9.7 eq) in THF (100 mL) at room temperature. After 24 h, the contents were filtered through Celite ™, the cake washed with THF, and the solvent of the filtrate removed in vacuo. The residue was flash chromatographed in 1:1 hexane/ethyl acetate to 100% ethyl acetate over silica gel to yield the dialdehyde which eluted first; 1.25 g (15%) of a tan glass. NMR (DMSO-d$_6$) δ 10.27 (s,1H); 10.17 (s,1H); 7.81 (d,1H,J=7Hz); 7.68 (m,2H); 7.50–7.23 (m,10H); 7.09 (d,2H,J=9Hz); 6.96 (d,2H,J=9Hz); 6.86 (m,6H); 5.59 (s,2H); 2.52 (t,2H,J=7Hz); 1.58 (t of q, 2H,J=7,7Hz); 0.77 (t,3H,J=7Hz). IR (neat) 1697; 1672 cm$^{-1}$. Anal. calcd. for $C_{41}H_{34}N_6O_2$: C, 76.62; H, 5.33; N, 13.07. Found: C, 76.46; H, 5.54; N, 12.94.

Continued elution yielded the 4-hydroxymethylimidazole-5-carboxaldehyde product as a light yellow solid: mp 164.5°–166.0° C. NMR (DMSO-d$_6$) δ 9.86 (s,1H); 7.80 (d,1H,J=9Hz); 7.63 (t,1H,J=9Hz); 7.53 (t,1H,J=7Hz); 7.50–7.25 (m,10H); 7.07 (d,2H,J=9Hz); 6.97–6.80 (m,8H); 5.47 (t,1H,J=7Hz); 5.29 (s,2H); 4.63 (d,2H,J=7Hz); 2.37 (t,2H,J=7Hz); 1.49 (t of q,2H,J=7,7Hz); 0.73 (t,3H,J=7Hz). IR (NuJol) 1688 cm$^{-1}$. Anal. calcd. for $C_{41}H_{36}N_6O_2 \cdot (H_2O)_{0.1}$: C, 76.16; H, 5.64; N, 12.84. Found: C, 76.02; H, 5.36; N, 12.84.

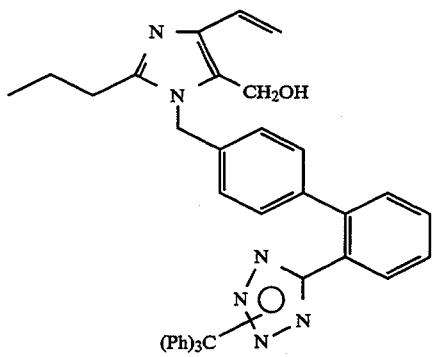

PART G: Preparation of 5-hydroxymethyl-2-n-propyl-1-[(2'-(N-triphenylmethyl-(1H-tetrazol-5-yl))biphenyl-4-yl)methyl]-4-vinylimidazole n-BuLi (2.5M in THF) (1.70 mL, 4.3 mmol, 2.1 eq) was added dropwise to a suspension of methyltriphenylphosphonium bromide (1.53 g, 4.3 mmol, 2.1 eq) in THF (50mL) at 0° C. under $N_2$.

The suspension became a dark yellow solution. Afterwards, a solution of 5-hydroxymethyl-2-n-propyl-1-[(2'-(N-triphenylmethyl-(1H-tetrazol-5-yl))biphenyl-4-yl)methyl]imidazole-4-carboxaldehyde (1.31 g, 2.0 mmol, 1.0 eq) in THF (minimum to dissolve) was added thereto and the resultant light milky yellow solution was stirred overnight at room temperature. The solution was diluted with ethyl acetate and washed with water (3×). The organic layer was dried (MgSO$_4$), the solvent removed in vacuo, and the residue flash chromatographed over silica gel in 1:1 hexane/ethyl acetate to yield 620 mg (48%) of a white glass: NMR (DMSO-d$_6$) δ 7.79 (d,1H,J=7Hz); 7.62 (t,1H,J=7Hz); 7.55 (t,1H,J=7Hz); 7.45 (d,1H,J=7Hz); 7.41–7.18 (m,9H); 7.06 (d,2H,J=9Hz); 6.95–6.80 (m,8H); 6.80–6.55 (m,1H); 5.73 (d of d,1H,J=17,3 Hz); 5.17 (s,2H); 5.10 (t,1H,J=7Hz); 5.05 (d of d,1H,J=12,3Hz); 4.28 (d,2H,J=7Hz); 2.37 (t,2H,J=7Hz); 1.50 (t of q,2H,J=7,7Hz); 0.78 (t,3H,J=7Hz). IR (neat) 1029; 1006; 909; 733; 698 cm$^{-1}$. Anal. calcd. for $C_{42}H_{38}N_6O \cdot H_2O$: C, 76.34; H, 6.10; N, 12.72. Found: C, 76.49; H, 5.88; N, 12.52.

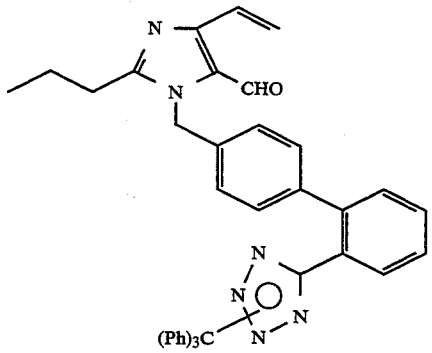

PART H: Preparation of 2-n-propyl-1-[(2'-(N-triphenylmethyl-(1H-tetrazol-5-yl))biphenyl-4-yl)methyl]-4-vinyl-imidazole-5-carboxaldehyde 5-hydroxymethyl-2-n-propyl-1-[(2'-(N-triphenylmethyl-(1H-tetrazol-5-yl))biphenyl-4-yl)methyl]-4-vinylimidazole (470 mg, 0.73 mmol, 1 eq), Dess-Martin periodinane (J. Org. Chem. (1983) 48, 4155) (341 mg, 0.80 mmol, 1.1 eq) and methylene chloride (10mL) were mixed and stirred under nitrogen overnight. The solvent was removed in vacuo and the residue flash chromatographed in 3:2 hexane ethyl acetate over silica gel to yield 310 mg (66%) of a white glass. NMR (DMSO-d$_6$) δ 9.91 (s,1H); 7.80 (d,1H,J=7Hz); 7.61 (t,1H, J=7Hz); 7.54 (t,1H,J=7Hz); 7.48–7.22(m,10H); 7.20 (d,1H,J=9Hz); 7.06 (d,2H,J=9Hz); 7.00–6.75 (m,8H); 6.15 (d of d,1H,J=17,3 Hz); 5.52 (s,2H); 5.47 (d of d,1H,J=12,3 Hz); 2.49 (t,2H,J=7Hz); 1.57 (t of q,2H,J=7,7Hz); 0.79 (t,3H,J=7Hz). IR (neat) 1658 cm$^{-1}$. Anal. calcd. for $C_{42}H_{36}N_6O \cdot (H_2O)_{0.5}$: C, 77.63; H, 5.74; N, 12.93. Found: C, 77.53; H, 5.73; N, 12.64.

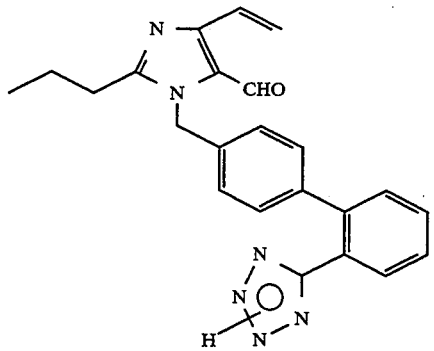

PART I: Preparation of 2-n-propyl-1-[(2'-(1H-tetrazol-5-yl)biphenyl-4-yl)methyl]-4-vinyl-imidazole-5-carboxaldehyde 2-n-propyl-1-[(2'-(N-triphenylmethyl-(1H-tetrazol-5-yl))biphenyl-4-yl)methyl]-4-vinyl-imidazole-5-carboxaldehyde (330 mg), trifluoroacetic acid (1.65 mL), water (1.65 mL), and THF (1.65 mL) were mixed and stirred at room temperature. After 8 h, the mixture was neutralized to pH=7 with 10N NaOH and the solvents removed in vacuo. The residue was flash chromatographed in 1:1 hexane/ethyl acetate to 100% ethanol to yield 270 mg of a white glass. NMR (DMSO-d6) δ 9.92 (s,1H); 7.65-7.50 (m,1H); 7.50-7.12 (m,3H); 7.09 (d,2H,J=9Hz); 6.89 (d,2H,J=9Hz); 6.11 (d of d1H,J=17,3Hz); 5.55 (s,2H); 5.45 (d of d, 1H,J=12,3 Hz); 2.63 (t,2H,J=7Hz); 1.64 (t of q,2H,J=7,7Hz); 0.90 (t,3H,J=7Hz). IR (Nujol) 1680 cm$^{-1}$.

EXAMPLE 2

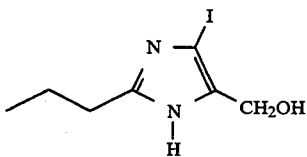

PART A: Preparation of 5-hydroxymethyl-4-iodo-2-n-propylimidazole

A solution of 31.5 g of 4(5)-hydroxymethyl-2-n-propylimidazole and 50.6 g of N-iodosuccinimide in 560 mL of 1,4-dioxane and 480 mL of 2-methoxyethanol was stirred at 45° C. for 2 h. The solvents then were removed under vacuum. The resulting solids were washed with distilled water and then were dried to afford 54.6 g of the product as a yellow solid; mp 169°-170° C. NMR (DMSO-d6) δ 12.06 (br s,1H); 5.08 (t,1H); 4.27 (d,2H); 2.50; (t,2H); 1.59 (sext.,2H); 0.84 (t,3H).

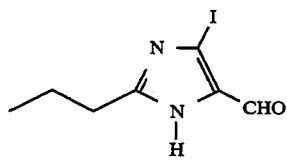

PART B: Preparation of 4-iodo-2-n-propylimidazole-5-carboxaldehyde

To a solution of 35.8 g of 5-hydroxymethyl-4-iodo-2-n-propylimidazole in 325 mL of glacial acetic acid at 20° C. was added dropwise over 1 h 290 mL of 1.0N aqueous ceric ammonium nitrate solution. The resulting mixture was stirred at 20° C. for 1 h. The reaction mixture then was diluted with water, adjusted to pH 5-6 employing aqueous sodium hydroxide solution, and extracted with chloroform. The combined organic phases were washed with water and brine, dried over anhydrous sodium sulfate, filtered, and concentrated. The resulting crude solid was recrystallized from 1-chlorobutane to furnish 29.9 g of product as a light yellow solid: mp 141°-142° C. NMR (CDCl3) δ 11.51 (br s,1H); 9.43 (s,1H); 2.81 (t,2H); 1.81 (sext., 2H); 0.97 (t,3H).

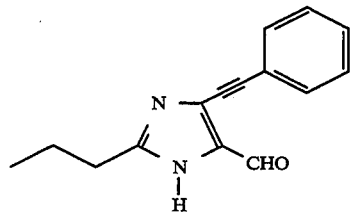

PART C: Preparation of 3-n-propyl-4-(phenylethynyl)imidazole-5-carboxaldehyde A solution of 2.64 g (0.01 mol) of 4-iodo-2-n-propylimidazole-5-carboxaldehyde, 25 mL of dry DMF, 2.5 mL of triethylamine, 1.00 g (0.001426 mol) of bis(triphenylphosphine)palladium chloride and 5.00 g (0.017 mol) of (phenylethynyl)tributyltin was heated to 70° C. under nitrogen. The reaction was stirred for 120 hours, then cooled. The precipitate was filtered and washed with methylene chloride, and the resulting filtrate was evaporated under reduced pressure. The residue was dissolved in 200 mL of methylene chloride and extracted three times with 100 mL of 10HCl. The aqueous layer pH was adjusted to 10 with 50% sodium hydroxide and extracted three times with 100 mL of methylene chloride. The organic phase was dried over sodium sulfate and evaporated under reduced pressure. Yield 0.56 g (0.0023 mol, 23%) of 3-n-propyl-4-(phenylethynyl)imidazole-5-carboxaldehyde. NMR (CDCl3) δ 9.89 (s,1H); 8.22 (s,1H); 7.93 (m,3H); 7.53 (m,2H); 2.87 (t,2H); 1.87 (m,2H); 1.03 (t,3H).

The following intermediates could be prepared by the procedure described in example 2, part C:

| $R^6$ | R | mp (°C.) |
|---|---|---|
| n-propyl | 4-CF3 | |
| n-propyl | 4-OMe | |

-continued

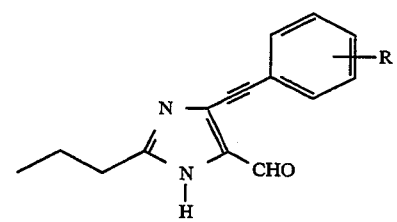

| R⁶ | R | mp (°C.) |
|---|---|---|
| n-propyl | 4-COOH | |
| n-propyl | 4-CON(Me)₂ | |
| n-propyl | 4-SO₂CH₃ | |
| n-propyl | 4-SO₂NMe₂ | |
| n-propyl | 3-CF₃ | |
| n-propyl | 3-OMe | |
| n-propyl | 3-COOH | |
| n-propyl | 3-CON(Me)₂ | |
| n-propyl | 3-SO₂CH₃ | |
| n-propyl | 3-SO₂NMe₂ | |
| n-butyl | 4-CF₃ | |
| n-butyl | 4-OMe | |
| n-butyl | 4-COOH | |
| n-butyl | 4-CON(Me)₂ | |
| n-butyl | 4-SO₂CH₃ | |
| n-butyl | 4-SO₂NMe₂ | |
| n-butyl | 3-CF₃ | |
| n-butyl | 3-OMe | |
| n-butyl | 3-COOH | |
| n-butyl | 3-CON(Me)₂ | |
| n-butyl | 3-SO₂CH₃ | |
| n-butyl | 3-SO₂NMe₂ | |

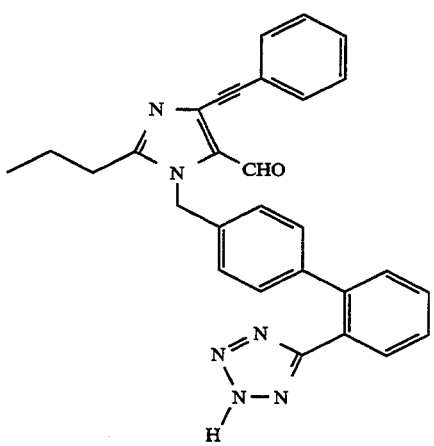

PART D. Preparation of 4-phenylethynyl-3-n-propyl-1-[(2'-(1H-tetrazol-5-yl)biphenyl-4-yl) methyl]imidazole-5-carboxaldehyde 3-n-Propyl-4-(phenylethynyl)imidazole-5-carboxaldehyde was alkylated with 4-bromomethyl-2'-(N-triphenylmethyl-(1H-tetrazol-5-yl))biphenyl by the procedure described in example 1, parts D and I, to yield the entitled product. NMR (CDCl₃) δ 9.88 (s,1H): 8.03 (m,1H); 7.57–7.27 (m,8H); 7.17 (m,2H); 7.01 (m,2H); 5.55 (s,2H); 2.61 (t,2H); 1.75 (m,2H); 0.99 (t,3H).

Examples 3–26 (Table 1) could be made by the procedures described in Example 2.

TABLE 1

[Structure shown above table]

| Example No. | R⁶ | R | mp (°C.) |
|---|---|---|---|
| 3 | n-propyl | 4-CF₃ | |
| 4 | n-propyl | 4-OMe | |
| 5 | n-propyl | 4-COOH | |
| 6 | n-propyl | 4-CON(Me)₂ | |
| 7 | n-propyl | 4-SO₂CH₃ | |
| 8 | n-propyl | 4-SO₂NMe₂ | |
| 9 | n-propyl | 3-CF₃ | |
| 10 | n-propyl | 3-OMe | |
| 11 | n-propyl | 3-COOH | |
| 12 | n-propyl | 3-CON(Me)₂ | |
| 13 | n-propyl | 3-SO₂CH₃ | |
| 14 | n-propyl | 3-SO₂NMe₂ | |
| 15 | n-butyl | 4-CF₃ | |
| 16 | n-butyl | 4-OMe | |
| 17 | n-butyl | 4-COOH | |
| 18 | n-butyl | 4-CON(Me)₂ | |
| 19 | n-butyl | 4-SO₂CH₃ | |
| 20 | n-butyl | 4-SO₂NMe₂ | |
| 21 | n-butyl | 3-CF₃ | |
| 22 | n-butyl | 3-OMe | |
| 23 | n-butyl | 3-COOH | |
| 24 | n-butyl | 3-CON(Me)₂ | |
| 25 | n-butyl | 3-SO₂CH₃ | |
| 26 | n-butyl | 3-SO₂NMe₂ | |

EXAMPLE 27

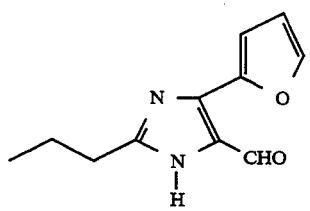

PART A: Preparation of 4-(furan-2-yl)-2-n-propylimidazole-5-carboxaldehyde

A solution of 2.64 g (0.01 mol) of 4-iodo-3-n-propylimidazole-5-carboxaldehyde, 60 mL of toluene, and 0.33 g (0.00029 mol) of tetrakistriphenylphosphine palladium (0) was stirred at room temperature under nitrogen, while a solution of 2.34 g (0.0174 mol) of furan-2-ylboronic acid in 50 mL of ethanol was slowly added. The reaction was stirred for 5 minutes, after which 12 mL of 2M sodium carbonate was slowly added. After the addition was completed, the reaction was refluxed for 8 h and cooled. The reaction was filtered, the filtrate was evaporated under reduced pressure, and the resulting residue was dissolved in 300 mL of methylene chloride, washed twice with 100 mL of saturated sodium chloride solution, washed twice with 100 mL of distilled water, and washed twice with 300 mL of 10% HCl. The HCl layer was made basic with 50% sodium hydroxide until the pH=10. At this point, the basic water layer was extracted three times with 300 mL of methylene chloride, the methylene chloride layer was dried over sodium sulfate and evaporated under reduced pressure. Yield: 0.34 g (0.00156 mol, 5-carboxaldehyde. NMR (CDCl$_3$) δ 10.14. (s,1H); 9.54 (s,1H); 7.00 (d,1H); 6.55 (m,1H); 2.79 (t,2H); 1.80 (m,2H); 1.02 (t,3H).

The following intermediates (Table 2) were or could be prepared by the procedure described in Example 27, part A:

TABLE 2

| R6 | R7 | mp (°C.) |
|---|---|---|
| n-propyl | 4-biphenyl | glass[a] |
| n-propyl | 2-thienyl | wax[b] |
| n-propyl | thiazolyl | |
| n-propyl | 1,3-thiazol-2-yl | |
| n-propyl | 1,3-selenazol-2-yl | |
| n-propyl | oxazol-2-yl | |
| n-propyl | furan-3-yl | |
| n-propyl | thien-3-yl | |
| n-propyl | thiazol-4-yl | |
| n-propyl | thiazol-5-yl | |

TABLE 2-continued

| R6 | R7 | mp (°C.) |
|---|---|---|
| n-propyl | selenazol-4-yl | |
| n-propyl | selenazol-5-yl | |
| n-propyl | oxazol-4-yl | |
| n-propyl | oxazol-5-yl | |
| n-propyl | pyrimidin-2-yl | |
| n-propyl | pyrimidin-4-yl | |
| n-propyl | pyrimidin-5-yl | |
| n-propyl | pyridazin-3-yl | |
| n-propyl | pyridazin-4-yl | |
| n-propyl | pyrazin-2-yl | |
| n-propyl | 4-phenoxyphenyl | wax[c] |

TABLE 2-continued
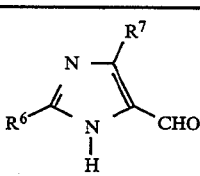
| R6 | R7 | mp (°C.) |
|---|---|---|
| n-propyl | 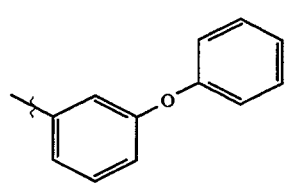 | |
| n-butyl | 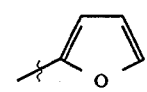 | |
| n-butyl | 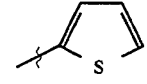 | |
| n-butyl | 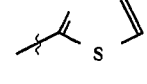 | |
| n-butyl | 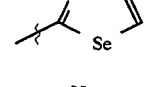 | |
| n-butyl | 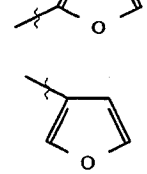 | |
| n-butyl | 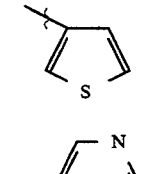 | |
| n-butyl | 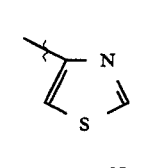 | |
| n-butyl | 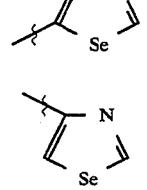 | |
| n-butyl |  | |
| n-butyl |  | |
TABLE 2-continued
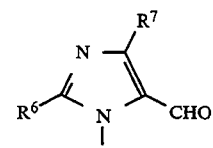
| R6 | R7 | mp (°C.) |
|---|---|---|
| n-butyl | 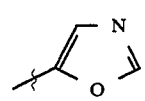 | |
| n-butyl |  | |
| n-butyl | 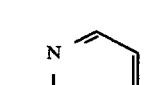 | |
| n-butyl | 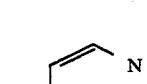 | |
| n-butyl | 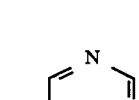 | |
| n-butyl | 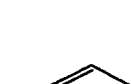 | |
| n-butyl | 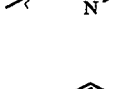 | |
| n-butyl | 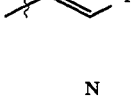 | |
| n-butyl | 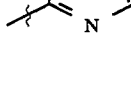 | |
| n-butyl | 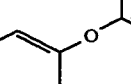 | |
| n-butyl |  | |

TABLE 2-continued

[Structure: imidazole with R6, R7, CHO, NH]

| R6 | R7 | mp (°C.) |
|---|---|---|
| n-butyl | 3-phenoxyphenyl | | a NMR(CDCl₃) δ 10.25(s, 1H); 9.85(s, 1H); 7.85(m, 2H); 7.65(m, 3H); 7.25(m, 4H); 2.83(t, 2H); 1.85(m, 2H); 1.05(t, 3H).
b NMR(CDCl₃) δ 11.45(bs, 1H); 9.88(s, 1H); 7.55(m, 1H); 7.37(m, 1H); 7.13(m, 1H); 2.73(t, 2H); 1.80(m, 2H); 0.91(t, 3H).
c NMR(DMSO-D₆) δ 9.66(s, 1H), 7.70(m, 1H), 7.38(m, 2H), 7.11(m, 2H), 7.04(m, 4H), 2.70(t, 2H), 1.80(m, 2H), 0.97(t, 3H).

PART B: Preparation of 4-(furan-2-yl)-2-n-propyl-1-[(2'-(1H-tetrazol-5-yl)biphenyl-4-yl)methyl]imidazole-5-carboxaldehyde 4-(furan-2-yl)-2-n-propylimidazole-5-carboxaldehyde was transformed into the entitled product by the procedures described in Example 1, parts D and I: mp 129 (dec.). NMR (CDCl₃) δ 10.15 (s,1H); 7.95 (d,1H); 7.55 (m,2H); 7.38 (m,2H); 7.10 (d,2H); 6.98 (d,2H); 6.85 (d,1H); 6.45 (m,1H); 5.55 (s,2H); 2.55 (t,2H); 1.70 (m,2H); 0.91 (t,3H).

The examples in Table 3 could be prepared by the procedures described in example 27 using the appropriate starting materials:

TABLE 3

[Structure: imidazole with R6, R7, CHO, CH2-biphenyl-tetrazole]

| Example No. | R⁶ | R⁷ | mp (°C.) |
|---|---|---|---|
| 28 | n-propyl | 4-biphenyl | glass a |
| 29 | n-propyl | 2-thienyl | |
| 30 | n-propyl | 2-thiazolyl | |
| 31 | n-propyl | 2-selenazolyl | |
| 32 | n-propyl | 2-oxazolyl | |
| 33 | n-propyl | 3-furyl | |
| 34 | n-propyl | 3-thienyl | |
| 35 | n-propyl | 3-thiazolyl | |
| 36 | n-propyl | 3-(N-linked)thiazolyl | |
| 37 | n-propyl | 3-selenazolyl | |
| 38 | n-propyl | 3-(N-linked)selenazolyl | |
| 39 | n-propyl | 3-oxazolyl | |

TABLE 3-continued

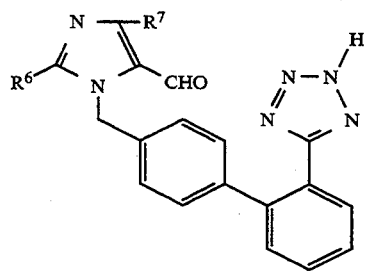

| Example No. | R⁶ | R⁷ | mp (°C.) |
|---|---|---|---|
| 40 | n-propyl | 4-oxazolyl | |
| 41 | n-propyl | 2-pyrimidinyl | |
| 42 | n-propyl | 4-pyrimidinyl | |
| 43 | n-propyl | 5-pyrimidinyl | |
| 44 | n-propyl | 3-pyridazinyl | |
| 45 | n-propyl | 4-pyridazinyl | |
| 46 | n-propyl | 2-pyrazinyl | |
| 47 | n-propyl | 4-phenoxyphenyl | glass[b] |
| 48 | n-propyl | 3-phenoxyphenyl | |
| 49 | n-butyl | 2-furyl | |
| 50 | n-butyl | 2-thienyl | |
| 51 | n-butyl | 2-thiazolyl | |
| 52 | n-butyl | 2-selenazolyl | |
| 53 | n-butyl | 2-oxazolyl | |
| 54 | n-butyl | 3-furyl | |
| 55 | n-butyl | 3-thienyl | |
| 56 | n-butyl | 5-thiazolyl | |
| 57 | n-butyl | 4-thiazolyl | |
| 58 | n-butyl | 5-selenazolyl | |
| 59 | n-butyl | 4-selenazolyl | |
| 60 | n-butyl | 5-oxazolyl | |

TABLE 3-continued

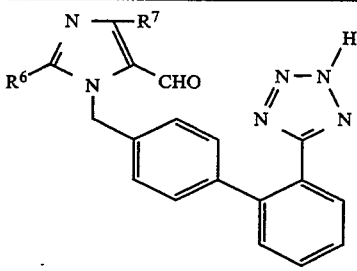

| Example No. | R⁶ | R⁷ | mp (°C.) |
|---|---|---|---|
| 61 | n-butyl | (4-methyloxazol-5-yl) | |
| 62 | n-butyl | (pyrimidin-2-yl) | |
| 63 | n-butyl | (pyrimidin-4-yl) | |
| 64 | n-butyl | (pyrimidin-5-yl) | |
| 65 | n-butyl | (pyridazin-3-yl) | |
| 66 | n-butyl | (pyridazin-4-yl) | |

TABLE 3-continued

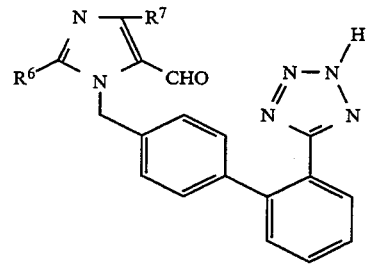

| Example No. | R⁶ | R⁷ | mp (°C.) |
|---|---|---|---|
| 67 | n-butyl | (pyrazin-2-yl) | |
| 68 | n-butyl | (4-phenoxyphenyl) | |
| 69 | n-butyl | (3-phenoxyphenyl) | |

ᵃNMR(CDCl3)∂9.81(s, 1H), 7.92(d, 2H), 7.53(m, 9H), 7.27(m, 4H), 7.11(d, 2H), 6.98(d, 2H), 5.60(s, 2H), 2.51(t, 2H), 1.73(m, 2H), 0.99(t, 3H).
ᵇNMR(CDCl3)∂9.69(s, 1H), 8.10(m, 1H), 7.58(m, 4H), 7.48(m, 3H), 7.18(d, 2H), 7.00(m, 7H), 5.62(s, 2H), 2.61(t, 2H), 1.79(m, 2H), 1.02(t, 3H).

The examples in Tables 4 and 5 can be made by procedures described in examples 1, 2, or 27 using the biphenyl starting materials disclosed in this patent or by other methods familiar to one skilled in the art.

TABLE 4

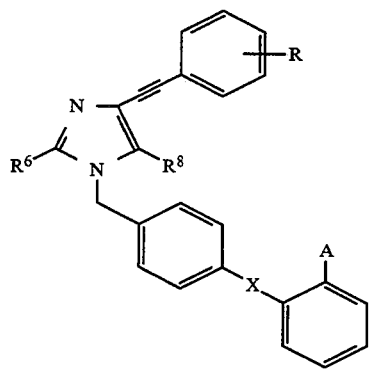

| Ex. No. | R⁶ | R | R8 | X | A | mp (°C.) |
|---|---|---|---|---|---|---|
| 70 | n-propyl | 4-CF₃ | CHO | single bond | COOH | |
| 71 | n-propyl | 4-OMe | CHO | single bond | COOH | |
| 72 | n-propyl | 4-COOH | CHO | single bond | COOH | |
| 73 | n-propyl | 4-CON(Me)₂ | CHO | single bond | COOH | |
| 74 | n-propyl | 4-SO₂CH₃ | CHO | single bond | COOH | |
| 75 | n-propyl | 4-SO₂NMe₂ | CHO | single bond | COOH | |
| 76 | n-propyl | 3-CF₃ | CHO | single bond | COOH | |

TABLE 4-continued

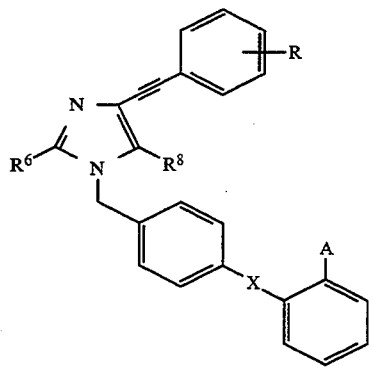

| Ex. No. | R6 | R | R8 | X | A | mp (°C.) |
|---|---|---|---|---|---|---|
| 77 | n-propyl | 3-OMe | CHO | single bond | COOH | |
| 78 | n-propyl | 3-COOH | CHO | single bond | COOH | |
| 79 | n-propyl | 3-CON(Me)$_2$ | CHO | single bond | COOH | |
| 80 | n-propyl | 3-SO$_2$CH$_3$ | CHO | single bond | COOH | |
| 81 | n-propyl | 3-SO$_2$NMe$_2$ | CHO | single bond | COOH | |
| 82 | n-butyl | 4-CF$_3$ | CHO | single bond | COOH | |
| 83 | n-butyl | 4-OMe | CHO | single bond | COOH | |
| 84 | n-butyl | 4-COOH | CHO | single bond | COOH | |
| 85 | n-butyl | 4-CON(Me)$_2$ | CHO | single bond | COOH | |
| 86 | n-butyl | 4-SO$_2$CH$_3$ | CHO | single bond | COOH | |
| 87 | n-butyl | 4-SO$_2$NMe$_2$ | CHO | single bond | COOH | |
| 88 | n-butyl | 3-CF$_3$ | CHO | single bond | COOH | |
| 89 | n-butyl | 3-OMe | CHO | single bond | COOH | |
| 90 | n-butyl | 3-COOH | CHO | single bond | COOH | |
| 91 | n-butyl | 3-SO$_2$CH$_3$ | CHO | single bond | COOH | |
| 92 | n-butyl | 3-SO$_2$NMe$_2$ | CHO | single bond | COOH | |
| 93 | n-propyl | 4-CF$_3$ | COOH | single bond | CN$_4$H | |
| 94 | n-propyl | 4-OMe | COOH | single bond | CN$_4$H | |
| 95 | n-propyl | 4-COOH | COOH | single bond | CN$_4$H | |
| 96 | n-propyl | 4-CON(Me)$_2$ | COOH | single bond | CN$_4$H | |
| 97 | n-propyl | 4-SO$_2$CH$_3$ | COOH | single bond | CN$_4$H | |
| 98 | n-propyl | 4-SO$_2$NMe$_2$ | COOH | single bond | CN$_4$H | |
| 99 | n-propyl | 3-CF$_3$ | COOH | single bond | CN$_4$H | |
| 100 | n-propyl | 3-OMe | COOH | single bond | CN$_4$H | |
| 101 | n-propyl | 3-COOH | COOH | single bond | CN$_4$H | |
| 102 | n-propyl | 3-CON(Me)$_2$ | COOH | single bond | CN$_4$H | |
| 103 | n-propyl | 3-SO$_2$CH$_3$ | COOH | single bond | CN$_4$H | |
| 104 | n-propyl | 3-SO$_2$NMe$_2$ | COOH | single bond | CN$_4$H | |
| 105 | n-butyl | 4-CF$_3$ | COOH | single bond | CN$_4$H | |
| 106 | n-butyl | 4-OMe | COOH | single bond | CN$_4$H | |
| 107 | n-butyl | 4-COOH | COOH | single bond | CN$_4$H | |
| 108 | n-butyl | 4-CON(Me)$_2$ | COOH | single bond | CN$_4$H | |
| 109 | n-butyl | 4-SO$_2$CH$_3$ | COOH | single bond | CN$_4$H | |
| 110 | n-butyl | 4-SO$_2$NMe$_2$ | COOH | single bond | CN$_4$H | |
| 111 | n-butyl | 3-CF$_3$ | COOH | single bond | CN$_4$H | |
| 112 | n-butyl | 3-OMe | COOH | single bond | CN$_4$H | |
| 113 | n-butyl | 3-COOH | COOH | single bond | CN$_4$H | |
| 114 | n-butyl | 3-SO$_2$NMe$_2$ | COOH | single bond | CN$_4$H | |
| 115 | n-propyl | 4-CF$_3$ | CHO | single bond | NHSO$_2$CF$_3$ | |
| 116 | n-propyl | 4-OMe | CHO | single bond | NHSO$_2$CF$_3$ | |
| 117 | n-propyl | 4-COOH | CHO | single bond | NHSO$_2$CF$_3$ | |
| 118 | n-propyl | 4-CON(Me)$_2$ | CHO | single bond | NHSO$_2$CF$_3$ | |
| 119 | n-propyl | 4-SO$_2$CH$_3$ | CHO | single bond | NHSO$_2$CF$_3$ | |
| 120 | n-propyl | 4-SO$_2$NMe$_2$ | CHO | single bond | NHSO$_2$CF$_3$ | |
| 121 | n-propyl | 3-CF$_3$ | CHO | single bond | NHSO$_2$CF$_3$ | |
| 122 | n-propyl | 3-OMe | CHO | single bond | NHSO$_2$CF$_3$ | |
| 123 | n-propyl | 3-COOH | CHO | single bond | NHSO$_2$CF$_3$ | |
| 124 | n-propyl | 3-CON(Me)$_2$ | CHO | single bond | NHSO$_2$CF$_3$ | |
| 125 | n-propyl | 3-SO$_2$CH$_3$ | CHO | single bond | NHSO$_2$CF$_3$ | |
| 126 | n-propyl | 3-SO$_2$NMe$_2$ | CHO | single bond | NHSO$_2$CF$_3$ | |
| 127 | n-butyl | 4-CF$_3$ | CHO | single bond | NHSO$_2$CF$_3$ | |
| 128 | n-butyl | 4-OMe | CHO | single bond | NHSO$_2$CF$_3$ | |
| 129 | n-butyl | 4-COOH | CHO | single bond | NHSO$_2$CF$_3$ | |
| 130 | n-butyl | 4-CON(Me)$_2$ | CHO | single bond | NHSO$_2$CF$_3$ | |
| 131 | n-butyl | 4-SO$_2$CH$_3$ | CHO | single bond | NHSO$_2$CF$_3$ | |
| 132 | n-butyl | 4-SO$_2$NMe$_2$ | CHO | single bond | NHSO$_2$CF$_3$ | |
| 133 | n-butyl | 3-CF$_3$ | CHO | single bond | NHSO$_2$CF$_3$ | |
| 134 | n-butyl | 3-OMe | CHO | single bond | NHSO$_2$CF$_3$ | |
| 135 | n-butyl | 3-COOH | CHO | single bond | NHSO$_2$CF$_3$ | |
| 136 | n-butyl | 3-SO$_2$NMe$_2$ | CHO | single bond | NHSO$_2$CF$_3$ | |
| 137 | n-propyl | 4-CF$_3$ | CHO | —NHCO— | CN$_4$H | |
| 138 | n-propyl | 4-OMe | CHO | —O— | CN$_4$H | |

TABLE 4-continued

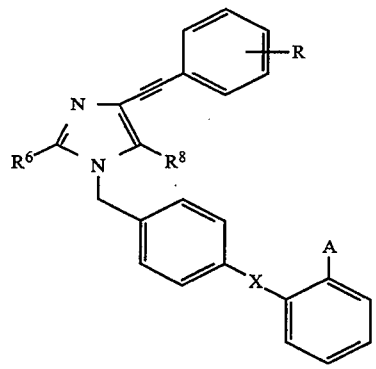

| Ex. No. | R6 | R | R8 | X | A | mp (°C.) |
|---|---|---|---|---|---|---|
| 139 | n-propyl | 4-COOH | CHO | —S— | CN4H | |
| 140 | n-propyl | 4-CON(Me)2 | CHO | —NH— | CN4H | |
| 141 | n-propyl | 4-SO2CH3 | CHO | —OCH2— | CN4H | |
| 142 | n-propyl | 4-SO2NMe2 | CHO | —SCH2— | CN4H | |
| 143 | n-propyl | 3-CF3 | CHO | —CH2O— | CN4H | |
| 144 | n-propyl | 3-OMe | CHO | —NHSO2— | CN4H | |
| 145 | n-propyl | 3-COOH | CHO | —SO2NH | CN4H | |
| 146 | n-propyl | 3-CON(Me)2 | CHO | —CH=CH— | CN4H | |
| 147 | n-propyl | 3-SO2CH3 | CHO | —CO— | CN4H | |
| 148 | n-propyl | 3-SO2NMe2 | CHO | —CH2— | CN4H | |
| 149 | n-butyl | 4-CF3 | CHO | —NHCO— | CN4H | |
| 150 | n-butyl | 4-OMe | CHO | —O— | CN4H | |
| 151 | n-butyl | 4-CON(Me)2 | CHO | —S— | CN4H | |
| 152 | n-butyl | 4-SO2CH3 | CHO | —NH— | CN4H | |
| 153 | n-butyl | 4-SO2NMe2 | CHO | —CH2S— | CN4H | |
| 154 | n-butyl | 3-CF3 | CHO | —SCH2— | CN4H | |
| 155 | n-butyl | 3-OMe | CHO | —SO2NH— | CN4H | |
| 156 | n-butyl | 3-COOH | CHO | —CO— | CN4H | |
| 157 | n-butyl | 3-SO2NMe2 | CHO | —CH2— | CN4H | |

TABLE 5

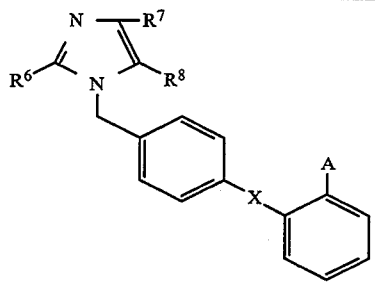

| Ex. No. | R6 | R7 | R8 | X | A | mp (°C.) |
|---|---|---|---|---|---|---|
| 158 | n-propyl | 2-furyl | COOH | single bond | CN4H | |
| 159 | n-propyl | 2-thienyl | COOH | single bond | CN4H | |
| 160 | n-propyl | 2-thiazolyl | COOH | single bond | CN4H | |
| 161 | n-propyl | 2-selenazolyl | COOH | single bond | CN4H | |

TABLE 5-continued

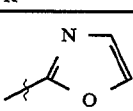

| Ex. No. | R⁶ | R⁷ | R⁸ | X | A | mp (°C.) |
|---|---|---|---|---|---|---|
| 162 | n-propyl |  | COOH | single bond | CN₄H | |
| 163 | n-propyl |  | COOH | single bond | CN₄H | |
| 164 | n-propyl | 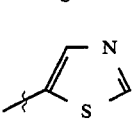 | COOH | single bond | CN₄H | |
| 165 | n-propyl | 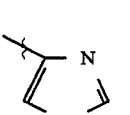 | CHO | single bond | COOH | |
| 166 | n-propyl | 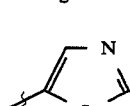 | CHO | single bond | COOH | |
| 167 | n-propyl | 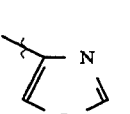 | CHO | single bond | COOH | |
| 168 | n-propyl | 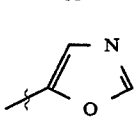 | CHO | single bond | COOH | |
| 169 | n-propyl | 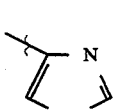 | CHO | single bond | COOH | |
| 170 | n-propyl | 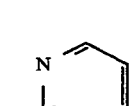 | CHO | single bond | COOH | |
| 171 | n-propyl | 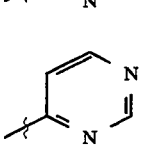 | CHO | single bond | NHSO₂CF₃ | |
| 172 | n-propyl |  | CHO | single bond | NHSO₂CF₃ | |

TABLE 5-continued

[Structure: imidazole with R6 on C2, R7 on C4, R8 on C5, N1 connected via CH2 to para-substituted phenyl, which connects via X to ortho-substituted phenyl bearing A]

| Ex. No. | R⁶ | R⁷ | R⁸ | X | A | mp (°C.) |
|---|---|---|---|---|---|---|
| 173 | n-propyl | pyrimidin-5-yl | CHO | single bond | NHSO₂CF₃ | |
| 174 | n-propyl | pyridazin-3-yl | CHO | single bond | NHSO₂CF₃ | |
| 175 | n-propyl | pyridazin-4-yl | CHO | single bond | NHSO₂CF₃ | |
| 176 | n-propyl | pyrazin-2-yl | CHO | —NHCO— | CN₄H | |
| 177 | n-propyl | 4-phenoxyphenyl | CHO | —O— | CN₄H | |
| 178 | n-propyl | 3-phenoxyphenyl | CHO | —S— | CN₄H | |
| 179 | n-propyl | furan-2-yl | CHO | —CO— | CN₄H | |
| 180 | n-propyl | thiophen-2-yl | CHO | —OCH₂— | CN₄H | |
| 181 | n-propyl | thiazol-2-yl | CHO | —CH=CH— | CN₄H | |
| 182 | n-propyl | 1-methylpyrazol-2-yl | CHO | single bond | CN₄H | |

TABLE 5-continued
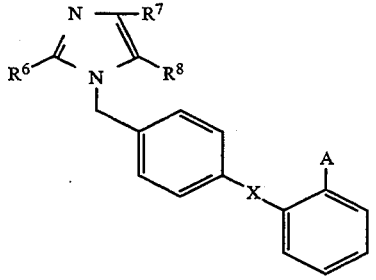
| Ex. No. | R⁶ | R⁷ | R⁸ | X | A | mp (°C.) |
|---|---|---|---|---|---|---|
| 183 | n-propyl | 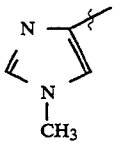 | CHO | single bond | CN₄H | |
| 184 | n-propyl | 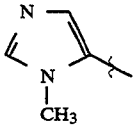 | CHO | single bond | CN₄H | |
| 185 | n-propyl | 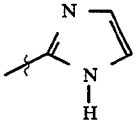 | CHO | single bond | CN₄H | |
| 186 | n-propyl | 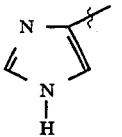 | CHO | single bond | CN₄H | |
| 187 | n-propyl | 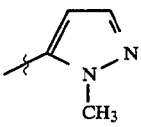 | CHO | single bond | CN₄H | |
| 188 | n-propyl | 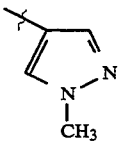 | CHO | single bond | CN₄H | |
| 189 | n-propyl | 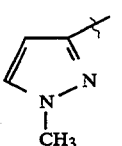 | CHO | single bond | CN₄H | |
| 190 | n-propyl | 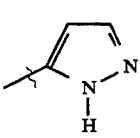 | CHO | single bond | CN₄H | |

TABLE 5-continued

[Structure: imidazole ring with R6, R7, R8 substituents, N-CH2-phenyl-X-phenyl(A)]

| Ex. No. | R6 | R7 | R8 | X | A | mp (°C.) |
|---------|------|------|------|------|------|------|
| 191 | n-propyl | 1H-pyrazol-4-yl | CHO | single bond | CN4H | |
| 192 | n-propyl | 1-methylpyrrol-2-yl | CHO | single bond | CN4H | |
| 193 | n-propyl | 1-methylpyrrol-3-yl | CHO | single bond | CN4H | |
| 194 | n-propyl | pyrrol-2-yl | CHO | single bond | CN4H | |
| 195 | n-propyl | pyrrol-3-yl | CHO | single bond | CN4H | |
| 196 | n-propyl | 1-methylimidazol-2-yl | COOH | single bond | CN4H | |
| 197 | n-propyl | 1-methylimidazol-4-yl | COOH | single bond | CN4H | |
| 198 | n-propyl | furan-2-yl | CH2OH | single bond | CN4H | |
| 199 | n-propyl | thiophen-2-yl | CH2OH | single bond | CN4H | |

TABLE 5-continued

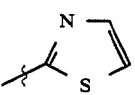

| Ex. No. | R6 | R7 | R8 | X | A | mp (°C.) |
|---|---|---|---|---|---|---|
| 200 | n-propyl | 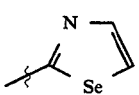 | CH2OH | single bond | CN4H | |
| 201 | n-propyl | 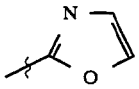 | CH2OH | single bond | CN4H | |
| 202 | n-propyl | 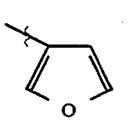 | CH2OH | single bond | CN4H | |
| 203 | n-propyl |  | CH2OH | single bond | CN4H | |
| 204 | n-propyl | 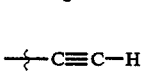 | CH2OH | single bond | CN4H | |
| 205 | n-propyl | —C≡C—H | CHO | single bond | CN4H | |
| 206 | n-propyl | —C≡C—CH3 | CHO | single bond | CN4H | |
| 207 | n-propyl | —C≡C—CH2—CH3 | CHO | single bond | CN4H | |
| 208 | n-propyl | —C≡C—CH2—Ph | CHO | single bond | CN4H | |
| 209 | n-propyl | 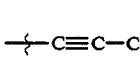 | CHO | single bond | CN4H | |
| 210 | n-propyl | 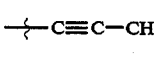 | CHO | single bond | CN4H | |
| 211 | n-propyl |  | CHO | single bond | CN4H | |
| 212 | n-propyl | 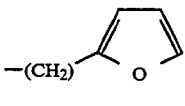 | CHO | single bond | CN4H | |

TABLE 5-continued

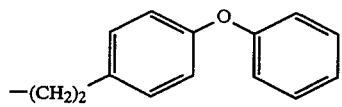

| Ex. No. | R⁶ | R⁷ | R⁸ | X | A | mp (°C.) |
|---|---|---|---|---|---|---|
| 213 | n-propyl | 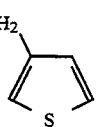 —(CH₂)₂— linked to phenyl-O-phenyl | CHO | single bond | CN₄H | |
| 214 | n-propyl | —CH=CH—CH₂— thienyl 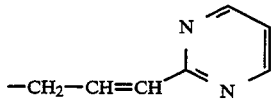 | CHO | single bond | CN₄H | |
| 215 | n-propyl | —CH₂—CH=CH— pyrimidinyl 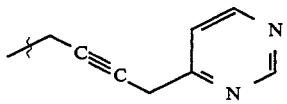 | CHO | single bond | CN₄H | |
| 216 | n-propyl | —C≡C—CH₂— pyrimidinyl 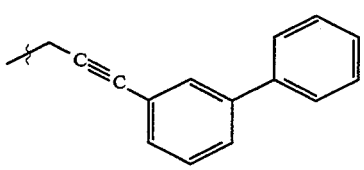 | CHO | single bond | CN₄H | |
| 217 | n-propyl | —C≡C—CH₂— biphenyl 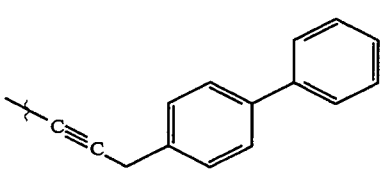 | CHO | single bond | CN₄H | |
| 218 | n-propyl | —C≡C—CH₂— biphenyl 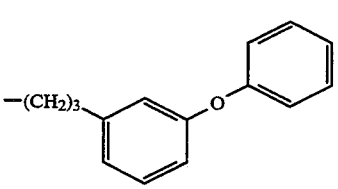 | CHO | single bond | CN₄H | |
| 219 | n-propyl | —(CH₂)₃— phenyl-O-phenyl 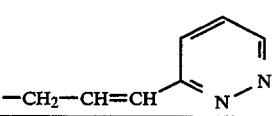 | CHO | single bond | CN₄H | |
| 220 | n-propyl | —CH₂—CH=CH— pyridazinyl | CHO | single bond | CN₄H | |

The following compounds in Table 6 were prepared or could be prepared by the procedure in example 1:

TABLE 6
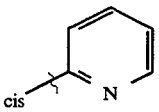
| Ex. No. | R6 | R7 | R8 | A | mp (°C.) |
|---|---|---|---|---|---|
| 221 | n-butyl | 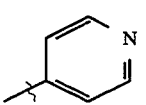 cis (2-pyridyl) | CHO | CN4H | |
| 222 | n-butyl | 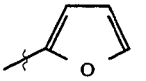 cis (3-pyridyl) | CHO | CN4H | |
| 223 | n-butyl | (4-pyridyl) | CHO | CN4H | |
| 224 | n-butyl | (2-furyl) | CHO | CN4H | |
| 225 | n-butyl | (2-thienyl) | CHO | CN4H | |
| 226 | n-butyl | (2-thiazolyl) | CHO | CN4H | |
| 227 | n-propyl | cis (2-pyridyl) | CHO | CN4H | |
| 228 | n-propyl | cis (3-pyridyl) | CHO | CN4H | |
| 229 | n-propyl | (4-pyridyl) | CHO | CN4H | |
| 230 | n-propyl | (2-furyl) | COOH | CN4H | |
| 231 | n-propyl | (2-thienyl) | CHO | CN4H | |

TABLE 6-continued

[Structure: imidazole with R6 at 2-position, R7-CH=CH- (propenyl) at 4-position, R8 at 5-position, N1 linked via CH2 to 4'-position of biphenyl bearing substituent A at 2'-position]

| Ex. No. | R$_6$ | R$_7$ | R$_8$ | A | mp (°C.) |
|---|---|---|---|---|---|
| 232 | n-propyl | 2-thiazolyl | COOH | CN$_4$H | |
| 233 | n-propyl | 2-selenazolyl | CH$_2$OH | CN$_4$H | |
| 234 | n-butyl | 2-oxazolyl | CH$_2$OH | CN$_4$H | |
| 235 | n-butyl | 2-pyrimidinyl | COOH | CN$_4$H | |
| 236 | n-propyl | 3-pyridazinyl | CHO | CN$_4$H | |
| 237 | n-propyl | 3-phenoxyphenyl | COOH | —NHSO$_2$CF$_3$ | |
| 238 | n-propyl | 5-thiazolyl | CHO | COOH | |
| 239 | n-propyl | 5-selenazolyl | CHO | CN$_4$H | |
| 240 | n-propyl | 5-oxazolyl | CHO | COOH | |
| 241 | n-butyl | 4-oxazolyl | CHO | CN$_4$H | |

EXAMPLE 242

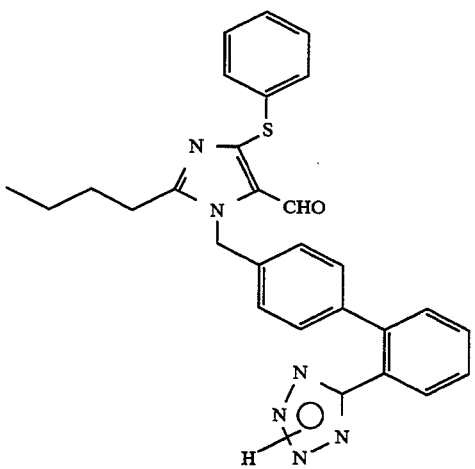

Preparation of
2-n-Butyl-4-phenylthio-1-[(2'-(1H-tetrazol-5-yl)biphenyl-4-yl)methyl]imidazole-5-carboxyaldehyde 2-n-Butyl-4-chloro-1-[(2'-N-triphenylmethyl(1H-tetrazol-5-yl)biphenyl-4-yl)methyl]imidazole-5-carboxyaldehyde (synthesized as described in European Patent Application Number 89100144.8, published 7.19.89) (590 mg, 0.89 mmol, 1 eq), and thiophenol (0.91 mL, 8.9 mmol, 10 eq) were added to a freshly prepared solution of sodium methoxide in methanol (sodium: 205 mg, 8.9 mmol, 10 eq; methanol, 40 mL) and the mixture refluxed overnight under $N_2$. The solvent was removed in vacuo and the residue dissolved in water (50 mL). The pH was adjusted to 10–12 with 10N NaOH. Gummy solids (trityl group-containing compound) formed which were dissolved by the addition of ethyl ether (50 mL). The layers were separated and the aqueous layer extracted with ethyl ether (2×50 mL). The aqueous layer was then extracted with ethyl acetate (6×50 mL). The ethyl acetate layers were collected, dried ($MgSO_4$), and the solvent removed in vacuo to yield a residue which was redissolved in water (50 mL). The pH was adjusted to 1 with conc. HCl. A gummy precipitate containing product formed which was dissolved in ethyl acetate (50 mL). The layers were separated and the aqueous layer was extracted with ethyl acetate (2×50 mL). The ethyl acetate layers were collected, dried ($MgSO_4$), and the solvent removed in vacuo to yield a white glass (200 mg). Crystallization from hot n-butylchloride yielded a white solid (142 mg): mp 1435°–145.5° C. NMR (DMSO-$d_6$) δ 9.82 (s, 1H); 7.80–761 (m, 2H); 7.58 (d, 1H, J=8Hz); 7.52 (d, 1H, J=8Hz); 7.45–7.20 (m, 5H); 7.09 (d, 1H, J=8Hz); 7.03 (d, 2H, J=8Hz); 5.62 (s, 2H); 2.64 (t, 2H, J=7Hz); 1.50 (t of t, 1H, J=7,7Hz); 1.25 (t of q, 2H, J=7,7Hz); 0.80(t, 3H, J=7Hz). Anal. calcd. for $CC_{28}H_{26}N_6OS.(H_2O)_{0.4}$: C, 67.02; H, 5.38; N, 16.75; S, 6.39. Found: C, 66.90; H, 5.20; N, 16.75; S, 6.00.

Examples 243–253 in Table 7 can be made by procedures described in example 242 and other examples in this patent application and in EP 89100144.8 (published 7.19.89) or by other methods familiar to one skilled in the art.

TABLE 7

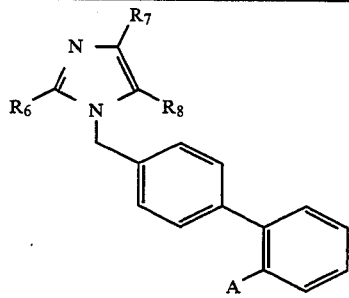

| Ex. No. | $R_6$ | $R_7$ | $R_8$ | A | mp (°C.) |
|---|---|---|---|---|---|
| 243 | n-butyl | –S–phenyl | CHO | COOH | 142.5–143.5 |
| 244 | n-butyl | CHO | –S–phenyl | COOH | a |
| 245 | n-butyl | –S–(2-pyridyl) | CHO | $CN_4H$ | b |
| 246 | n-butyl | SH (3-–S–phenyl) | CHO | COOH | c |

TABLE 7-continued

[Structure: imidazole ring with R6, R7, R8 substituents, N-CH2-biphenyl with A substituent at ortho position]

| Ex. No. | R6 | R7 | R8 | A | mp (°C.) |
|---|---|---|---|---|---|
| 247 | n-butyl | -S-(pyrimidin-2-yl) | CHO | $CN_4H$ | |
| 248 | n-butyl | -S-(pyridin-4-yl) | CHO | $CN_4H$ | |
| 249 | n-propyl | —NHCOCH$_3$ | CHO | $CN_4H$ | |
| 250 | n-propyl | CHO | NHSO2CF3 | $CN_4H$ | |
| 251 | n-propyl | -S-(3-hydroxypyridin-2-yl) | CHO | COOH | |
| 252 | n-propyl | -S-(4-methylpyrimidin-2-yl) | COOH | COOH | |
| 253 | n-propyl | -S-(4,5-dihydrothiazol-2-yl) | CH$_2$OH | COOH | |
| 254 | n-propyl | -S-(thiazol-2-yl) | CH$_2$OH | $CN_4H$ | |
| 255 | n-propyl | -S-(1-phenyltetrazol-5-yl) | CHO | COOH | |
| 256 | n-butyl | -S-(1-methyltetrazol-5-yl) | CHO | $CN_4H$ | |
| 257 | n-butyl | -S-(1-methylimidazol-2-yl) | CHO | $CN_4H$ | |

TABLE 7-continued
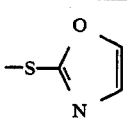
| Ex. No. | R$_6$ | R$_7$ | R$_8$ | A | mp (°C.) |
|---|---|---|---|---|---|
| 258 | n-butyl | 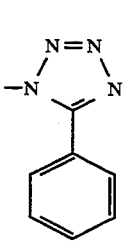 | CH$_2$OH | CN$_4$H | |
| 259 | n-propyl | 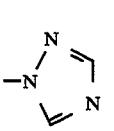 | CHO | COOH | |
| 260 | n-propyl | 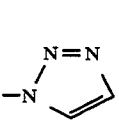 | CHO | CN$_4$H | |
| 261 | n-butyl | 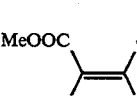 | CHO | CN$_4$H | |
| 262 | n-butyl | 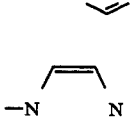 | CHO | CN$_4$H | |
| 263 | n-butyl | 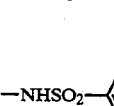 | CHO | CN$_4$H | |
| 264 | n-propyl | —NHSO$_2$— 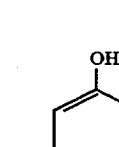 | CHO | CN$_4$H | |
| 265 | n-propyl | 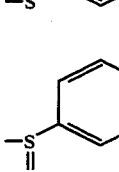 | CH$_2$OH | COOH | |
| 266 | n-butyl |  | CHO | COOH | |

TABLE 7-continued

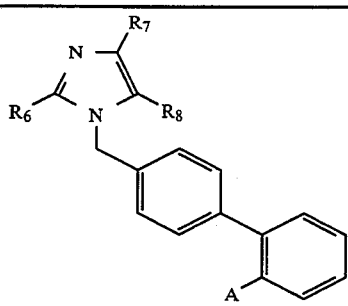

| Ex. No. | R6 | R7 | R8 | A | mp (°C.) |
|---|---|---|---|---|---|
| 267 | n-butyl | 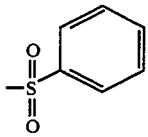 | CHO | CN4H | |

<sup>a</sup>NMR(DMSO-d<sub>6</sub>)∂9.97(s, 1H); 7.59(d, 1H, J=8Hz); &.50-7.10(m, 8H); 7.14(d, 2H, J=8H); 6.91(d, 2H, J=8Hz); 5.32(s, 2H); 2.66(t, 2H, J=7Hz); 1.58(t of t, 2H, J=7,7Hz); 1.28(t of q, 2H, J=7,7Hz); 0.82(t, 3H, J=7Hz).
<sup>b</sup>NMR(DMSO-d<sub>6</sub>)∂9.80(s, 1H); 8.41(d, 1H, J=7Hz); 7.72(d, 1H, J=7Hz); 7.55(d, 1H, J=7Hz); 7.49-7.25(m, 3H); 7.19(t, 2H, J=7Hz); 7.09(d, 2H, J=7Hz); 6.95(d, 2H, J=7Hz); 5.63(s, 2H); 2.70(t, 2H, J=7Hz); 1.57(t of t, 2H, J=7,7Hz); 1.29(t of q, 2H, J=7,7Hz); 0.81(t, 3H, J=7Hz).
<sup>c</sup>NMR(DMSO-d<sub>6</sub>)∂9.83(s, 1H); 7.72(d, 1H, J=8Hz); 7.65-7.15(m, 9H); 7.10(d, 2H, J=8Hz); 5.64(s, 2H); 2.64(t, 2H, J=7Hz); 1.50(t of t, 2H, J=7,7Hz); 1.23(t of q, 2H, J=7,7Hz); 0.78(t, 3H, J=7Hz).

EXAMPLE 268

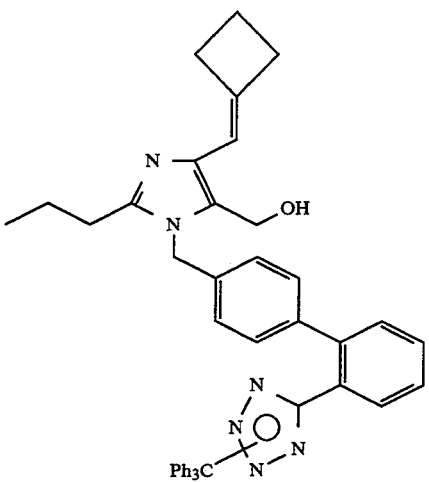

PART A: Preparation of 2-n-propyl-4-cyclobutylidenyl-5-hydroxymethyl-1-[(2'-(N-triphenylmethyl-(1H-tetrazol-5-yl))biphenyl-4-yl)methyl]imidazole (∂-Bromo-n-butyl)triphenylphosphonium bromide (7.42 g, 0.0155 mmol, 2 eq) was suspended in THF (125 mL) and 0.75M potassium hexamethyldisilazane (41.4 mL, 0.031 mmol, 4 eq) was added at room temperature. The mixture turned blood red. After 0.5 h, 2-n-propyl-5-hydroxymethyl-1-[(2'-(N-triphenylmethyl-(1H-tetrazol-5-yl))biphenyl-4-yl-methyl]imidazole-4-carboxaldehyde (5.00 g, 7.75 mmol, 1 eq) as a slurry in THF was added. The mixture eventually turned into a yellow-orange suspension. After 24 h, the reaction was worked up by adding a little methanol to quench, followed by ethyl acetate and water. The layers were separated and the organic layer was washed with water (2×) and brine (1×). The organic layer was dried (MgSO<sub>4</sub>), and solvent removed in vacuo, and the residue flash chromatographed in 60:40 pentane/ethyl acetate to 100% ethyl acetate to yield 4.12 g (78%) of a while solid: mp 181.5°-182.5° C. NMR (DMSO-d<sub>6</sub>) δ 7.78 (m, 1H); 7.61 (t,1H, J=7Hz); 7.54 (t,1H,J=7Hz); 7.48-7.20 (m,10H); 7.03 (d,2H,J=8Hz); 6.96-6.70 (m,8H); 5.99 (s,1H); 5.13 (s,2H); 4.97 (t,1H,J=7Hz); 4.21 (d,2H,J=7Hz); 3.05 (m,2H); 2.79 (m,2H); 2.31 (t,2H,J=7Hz); 1.98 (m,2H); 1.48 (t of q, 2H,J=7,7Hz); 0.77 (t,3H,J=7Hz). Anal. ((C<sub>45</sub>H<sub>42</sub>N<sub>6</sub>O.(H<sub>2</sub>O)<sub>0.75</sub>) C, H, N.

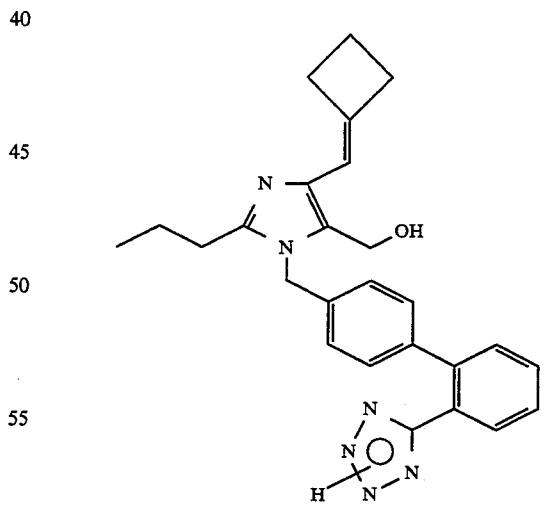

PART B: Preparation of 2-n-propyl-4-cyclobutylidenyl-5-hydroxymethyl-1-[(2'-(1H-tetrazol-5-yl)biphenyl-4-yl)methyl]imidazole 2-n-Propyl-4-cyclobutylidenyl-5-hydroxymethyl-1-[(2'-(N-triphenylmethyl-(1H-tetrazol-5-yl))biphenyl-4-yl)methyl]imidazole (1.00 g), methanol (25 mL) and THF (15 mL) were mixed and refluxed for 24 h. The solvents were removed in vacuo and the residue immediately flash chromatographed quickly in 1:1 pentane/ethyl acetate to 100% isopropanol and eventually to 100% ethanol to yield 320 mg of a light yellow glass: NMR (DMSO-d$_6$) δ 7.59 (d,1H,J=7Hz); 7.54 (t,1H,J=7Hz); 7.46 (t,1H,J=7Hz); 7.42 (d,1H,J=7Hz); 7.06 (d,2H,J=7Hz); 6.90 (d,2H,J=7Hz); 5.97 (s,1H); 5.17 (s,2H); 4.31 (s,2H); 3.04 (m,2H); 2.77 (m,2H); 2.42 (t,2H,J=7Hz); 1.97 (m,2H); 1.53 (t of q,2H,J=7,7Hz); 0.86 (t 3H, J=7Hz ). Anal. (C$_{26}$H$_{28}$N$_6$O) C, H, N.

Utility

The hormone angiotensin II (AII) produces numerous biological responses (e.g. vasoconstriction) through stimulation of its receptors on cell membranes. For the purpose of identifying compounds such as AII antagonists which are capable of interacting with the AII receptor, a ligand-receptor binding assay was utilized for the initial screen. The assay was carried out according to the method described by [Glossmann et al., *J. Biol. Chem.*, 249, 825 (1974)], but with some modifications. The reaction mixture contained rat adrenal cortical microsomes (source of AII receptor) in Tris buffer and 2 nM of $^3$H-AII with or without potential AII antagonist. This mixture was incubated for 1 hour at room temperature and the reaction was subsequently terminated by rapid filtration and rinsing through glass micro-fibre filter. Receptor-bound $^3$H-AII trapped in filter was quantitated by scintillation counting. The inhibitory concentration (IC$_{50}$) of potential AII antagonist which gives 50% displacement of the total specifically bound $^3$H-AII is a measure of the affinity of such compound for the AII receptor. Compounds of this invention which were tested in this binding assay exhibited IC$_{50}$ of 10$^{-5}$M or less (Table 8).

TABLE 8

| | Angiotensin II | Antihypertensive | |
|---|---|---|---|
| | Receptor Binding | Effects in renal Hypertensive Rats | |
| Ex. No. | IC$_{50}$ (μmolar) | Intravenous Activity[1] | Oral Activity[2] |
| 1 | 0.013 | + | + |
| 2 | 0.021 | + | NT[3] |
| 27 | 0.17 | + | NT[3] |
| 28 | 0.35 | NA | NT |
| 47 | 0.21 | NA | NT |
| 242 | 0.024 | + | + |
| 243 | 0.28 | NA | NT |
| 244 | 0.37 | NA | NT |
| 245 | 0.024 | + | + |
| 246 | 0.27 | + | NT |
| 268 | 0.044 | NT | NT |

[1]Significant decrease in blood pressure at 3.0 mg/kg or less
[2]Significant decrease in blood pressure at 30 mg/kg or less
N.A - Not active at 3 mg/kg or 30 mg/kg dosage tested. Although some of the compounds tested were not active orally, they were active intravenously.
NT Not tested.
NT[3] Not tested at 30 mg/kg p.o.

The potential antihypertensive effects of the compounds of this invention may be demonstrated by administering the compounds to awake rats made hypertensive by ligation of the left renal artery [Cangiano et al., *J. Pharmacol. Exp. Ther.*, 208, 310 (1979)]. This procedure increases blood pressure by increasing renin production with consequent elevation of AII levels. Compounds are administered orally at 30 mg/kg and/or intravenously via a cannula in the jugular vein at 3 mg/kg. Arterial blood pressure is continuously measured directly through a carotid artery cannula and recorded using a pressure transducer and a polygraph. Blood pressure levels after treatment are compared to pretreatment levels to determine the antihypertensive effects of the compounds which were tested. Some compounds of this invention exhibited intravenous activity at 3 mg/kg and some exhibited oral activity at 30 mg/kg (Table 8).

Dosage Forms

The compounds of this invention can be administered for the treatment of hypertension according to the invention by any means that effects contact of the active ingredient compound with the site of action in the body of a warm-blooded animal. For example, administration can be parenteral, i.e., subcutaneous, intravenous, intramuscular, or intra peritoneal. Alternatively, or concurrently, in some cases administration can be by the oral route.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

For the purpose of this disclosure, a warm-blooded animal is a member of the animal kingdom possessed of a homeostatic mechanism and includes mammals and birds.

The dosage administered will be dependent on the age, health and weight of the recipient, the extent of disease, kind of concurrent treatment, if any, frequency of treatment and the nature of the effect desired. Usually, a daily dosage of active ingredient compound will be from about 1–500 milligrams per day. Ordinarily, from 10 to 100 milligrams per day in one or more applications is effective to obtain desired results. These dosages are the effective amounts both for treatment of hypertension and for treatment of congestive heart failure, i.e., for lowering blood pressure and for correcting the hemodynamic burden on the heart to relieve the congestion.

The active ingredient can be administered orally in solid dosage forms, such as capsules, tablets, and powders, or in liquid dosage forms, such as elixirs syrups, and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in Remington's Pharmaceutical Sciences, A. Osol, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol. The solution is made to volume with water for injection and sterilized.

Suspension

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise in conjunction with another therapeutic agent. When the drugs are administered in physical combination, the dosage form and administration route should be selected for compatibility with both drugs. Suitable dosages, dosage forms and administration routes are illustrated in the following tables.

| Examples of NSAID's that can be combined with AII blockers of this invention: | | | |
|---|---|---|---|
| Drug | Dose (mg) | Formulation | Route |
| Indomethacin | 25 (2/3 times daily) | Tablet | Oral |
| Meclofenamate | 50-100 (2/3 times daily) | Tablet | Oral |
| Ibuprofen | 300-400 | Tablet | Oral |

| Examples of NSAID's that can be combined with AII blockers of this invention: -continued | | | |
|---|---|---|---|
| Drug | Dose (mg) | Formulation | Route |
| Piroxicam | (3/4 times daily) 10-20 | Tablet | Oral |
| Sulindac | (1/2 times daily) 150-200 | Tablet | Oral |
| Azapropazone | (2 times daily) 200-500 (3/4 times daily) | Tablet | Oral |

| Examples of diuretics that can be combined with AII blockers of this invention: | | | |
|---|---|---|---|
| Drug | Dose (mg) | Formulation | Route |
| Benzothiadizides (e.g. hydrochlorothiazide) | 25-100 (daily) | Tablet | Oral |
| Loop diuretics (e.g. furosemide) | 50-80 (daily) | Tablet | Oral |

When used with an NSAID, the dosage of AII blockers will generally be the same as when the AII blocker is used alone, i.e., 1-500 milligrams per day, ordinarily from 10 to 100 milligrams per day in one or more applications. When used with diuretics, the initial dose of AII blocker can be less, e.g., 1-100 milligrams per day and for the more active compounds 1-10 milligrams per day.

It is expected that the compounds of this invention will also be useful in the treatment of chronic renal failure.

We claim:

1. An antihypertensive compound of the formula

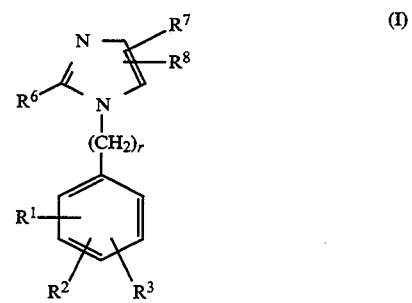

wherein
$R^1$ is

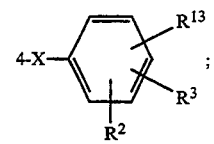

$R^2$ is H; Cl; Br; I; F; $NO_2$; CN; alkyl of 1 to 4 carbon atoms; acyloxy of 1 to 4 carbon atoms; alkoxy of 1 to 4 carbon atoms; $CO_2H$; $CO_2R^9$; $NHSO_2CH_3$; $NHSO_2CF_3$; $CONHOR^{12}$; $SO_2NH_2$;

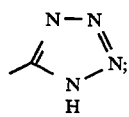

aryl; or furyl;

$R^3$ is H; Cl, Br; I; or F; alkyl of 1 to 4 carbon atoms or alkoxy of 1 to 4 carbon atoms;

$R^6$ is alkyl of 2 to 10 carbon atoms, alkenyl or alkynyl of 3 to 10 carbon atoms $R^7$ is vinyl; cycloalkylidenyl; alkynyl of 2–10 carbon atoms; phenylalkynyl where the alkynyl portion is 2–6 carbon atoms; heteroaryl selected from 2- and 3-thienyl, 2- and 3-furyl, 2-, 3-, and 4-pyridyl, 2-, 4- or 5-imidazolyl; o-, m- or p-biphenylyl; o-, m- or p-phenoxyphenyl; substituted phenylalkynyl where the alkynyl portion is 2–6 carbon atoms, heteroaryl selected from 2- and 3-thienyl, 2- and 3-furyl, 2-, 3- and 4-pyridyl, 2-, 4- or 5-imidazolyl, o-, m- or p-biphenylyl or o-, m- or p-phenoxyphenyl substituted with 1or 2 substituents selected from halogen, hydroxy, mercapto, alkoxy of 1–5 carbon atoms, alkyl of 1–5 carbon atoms, —NO$_2$—, —CN, —CF$_3$, —COR$^{16}$, —CH$_2$OR$^{17}$, —NHCOR$^{17}$, —CONR$^{18}$R$^{19}$, S(O)$_r$R$^{17}$, and SO$_2$NR$^{18}$R$^{19}$; 2-, 4- or 5-imidazolyl substituted on ring nitrogen with alkyl of 1–5 carbon atoms, phenyl or benzyl; or substituted alkyl, alkenyl, or alkynyl of 1 to 10 carbon atoms substituted with an unsubstituted heteroaryl selected from 2- and 3-thienyl, 2- and 3-furyl, 2-, 3- and 4-pyridyl, 2-, 4- or 5-imidazolyl, o-, m- or p-biphenylyl or o-, m- or p-phenoxyphenyl or a heteroaryl selected from 2- and 3-thienyl, 2- and 3-furyl, 2-, 3- and 4-pyridyl, 2-, 4- or 5-imidazolyl, o-, m- or p-biphenylyl or o-, m- or p-phenoxylphenyl substituted with 1 or 2substituents selected from halogen, hydroxy, mercapto, alkoxy of 1–5 carbon atoms, alkyl of 1–5 carbon atoms, —NO$_2$, —CN, —CF$_3$, —COR$^{16}$, —CH$_2$OR$^{17}$, —NHCOR$^{17}$, —CONR$^{18}$R$^{19}$, S(O)$_r$R$^{17}$, and SO$_2$NR$^{18}$R$^{19}$; —S—(O)$_r$-heteroaryl, —S—(O)$_r$-biphenylyl, —S(O)$_r$-phenoxyphenyl, —S(O)$_r$R$^{17}$, —NR$^{18}$R$^{19}$, N-imidazolyl, where heteroaryl is a heterocycle defined in the scope of $R^7$ and where the phenyl group in $R^{17}$ of —S—(O)$_r$R$^{17}$, the N-imidazolyl, is unsubstituted or substituted with one or two substituents selected from halogen, hydroxy, mercapto, alkoxy of 1–5 carbon atoms, alkyl of 1–5 carbon atoms, —NO$_2$, —CN, —CF$_3$, —COR$^{16}$, —CH$_2$OR$^{17}$, —NHCOR$^{17}$, —CONR$^{18}$R$^{19}$, S(O)$_r$R$^{17}$, and SO$_2$NR$^{18}$R$^{19}$;

$R^8$ is

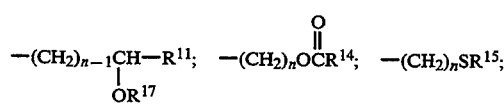

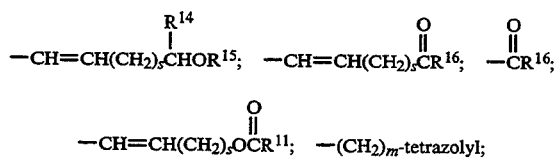

-continued

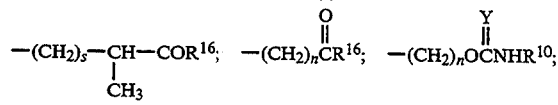

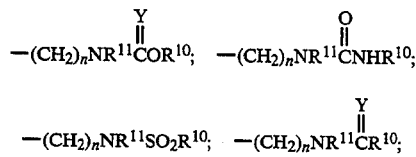

$R^9$ is

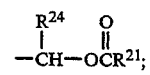

$R^{10}$ is alkyl of 1 to 6 carbon atoms or perfluoroalkyl of 1 to 6 carbon atoms, 1-adamantyl, 1-naphthyl, 1-(1-naphthyl)ethyl, or (CH$_2$)$_p$C$_6$H$_5$;

$R^{11}$ is H, alkyl of 1 to 6 carbon atoms, cycloalkyl of 3 to 6 carbon atoms, phenyl or benzyl;

$R^{12}$ is H, methyl or benzyl;

$R^{13}$ is —CO$_2$H; —NHSO$_2$CH$_3$; —NHSO$_2$CF$_3$;

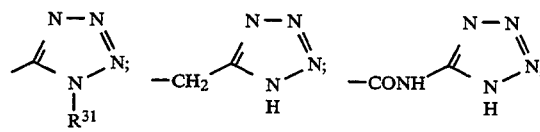

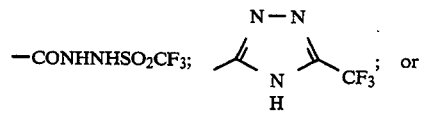

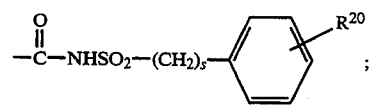

$R^{14}$ is H, alkyl or perfluoroalkyl of 1 to 8 carbon atoms, cycloalkyl of 3 to 6 carbon atoms, phenyl or benzyl;

$R^{15}$ is H, alkyl of 1 to 6 carbon atoms, cycloalkyl of 3 to 6 carbon atoms, phenyl, benzyl, acyl of 1 to 4 carbon atoms, phenacyl;

$R^{16}$ is H, alkyl of 1 to 6 carbon atoms, cycloalkyl of 3 to 6 carbon atoms, (CH$_2$)$_p$C$_6$H$_5$, OR$^{17}$, or NR$^{18}$R$^{19}$;

$R^{17}$ is H, alkyl of 1 to 6 carbon atoms, cycloalkyl of 3 to 6 carbon atoms, phenyl or benzyl;

$R^{18}$ and $R^{19}$ independently are H, alkyl of 1 to 4 carbon atoms, phenyl, benzyl, a-methylbenzyl, or taken together with the nitrogen form a ring of the formula

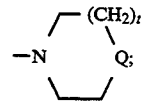

Q is NR$^{20}$, 0 or CH$_2$;

$R^{20}$ is H, alkyl of 1–4 carbon atoms, or phenyl;

$R^{21}$ is alkyl of 1 to 6 carbon atoms, —NR$^{22}$R$^{23}$, or

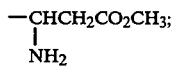

R²² and R²³ independently are H, alkyl of 1 to 6 carbon atoms, benzyl, or are taken together as $(CH_2)_u$ where u is 3–6;
R²⁴ is H, $CH_3$ or $-C_6H_5$;
R³¹ is H, alkyl of 1 to 4 carbon atoms, $-CH_2CH=CH_2$ or $-CH_2C_6H_4R^{32}$;
R³² is H, $NO_2$, $NH_2$, OH or $OCH_3$;
X is a carbon-carbon single bond;
Y is O or S;
m is 1 to 5;
n is 1 to 10;
p is 0 to 3;
r is 0 to 2;
s is 0 to 5;
t is 0 or 1;
or a pharmaceutically acceptable salt thereof; provided that:
(1) the R¹ group is not in the ortho position;
(2) when R¹³ is $CO_2H$, or

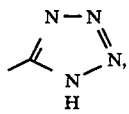

then R¹³ must be in the ortho or meta position; or when R¹³ is $NHSO_2CF_3$ or $NHSO_2CH_3$, R¹³ must be ortho.

2. A compound of claim 1 having the formula:

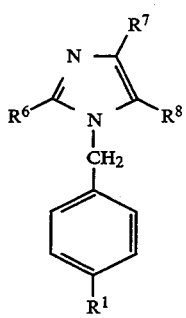

(II)

wherein
R¹ is

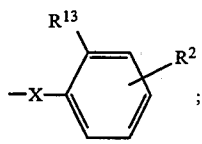

R⁸ is $-(CH_2)_m$-tetrazolyl, $-(CH_2)_nOR^{11}$;

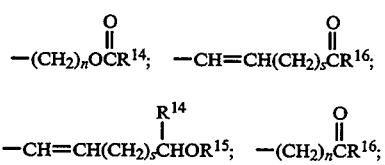

-continued
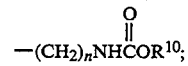

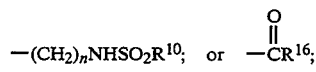

R¹⁶ is H, alkyl of 1 to 5 carbon atoms, $OR^{17}$, or $NR^{18}R^{19}$.

3. A compound of claim 2 wherein:
R² is H, alkyl of 1 to 4 carbon atoms, halogen, or alkoxy of 1 to 4 carbon atoms;
R⁶ is alkyl, alkenyl or alkynyl of 3 to 7 carbon atoms;
R⁷ is heteroaryl selected from 2- and 3-thienyl, 2- and 3-furyl, 2-, 3- and 4-pyridyl, or p-biphenylyl;

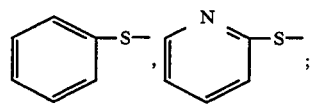

R⁸ is $-(CH_2)_mOR^{11}$;

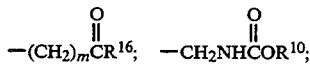

$-(CH_2)_mNHSO_2R^{10}$; or $-COR^{16}$;
R¹⁰ is $CF_3$, alkyl of 1 to 6 carbon atoms or phenyl;
R¹¹ is H, or alkyl of 1 to 4 carbon atoms;
R¹³ is $CO_2H$; $NHSO_2CF_3$ or

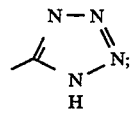

R¹⁴ is H, or alkyl of 1 to 4 carbon atoms;
R¹⁵ is H, alkyl of 1 to 4 carbon atoms, or acyl of 1 to 4 carbon atoms;
R¹⁶ is H, alkyl of 1 to 5 carbon atoms; $OR^{17}$; or

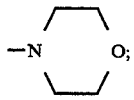

m is 1 to 5;
or a pharmaceutically acceptable salt thereof.

4. A compound of claim 1 wherein R¹ is

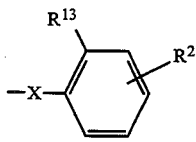

and X is a single bond, or a pharmaceutically suitable salt thereof.

5. A pharmaceutical composition comprising a pharmaceutically suitable carrier and a compound of any one of claims 4 and 1–3.

* * * * *